(12) United States Patent
Yantz et al.

(10) Patent No.: US 11,583,853 B2
(45) Date of Patent: Feb. 21, 2023

(54) KITS AND DEVICES FOR DETECTING ANALYTES

(71) Applicant: First Light Diagnostics, Inc., Chelmsford, MA (US)

(72) Inventors: Greg Yantz, Somerville, MA (US); Don Straus, Cambridge, MA (US); Gordon Siek, Somerville, MA (US); Damon Dehart, Bedford, MA (US)

(73) Assignee: FIRST LIGHT DIAGNOSTICS, INC., Chelmsford, MA (US)

( * ) Notice: Subject to any disclaimer, the term of this patent is extended or adjusted under 35 U.S.C. 154(b) by 21 days.

(21) Appl. No.: 16/543,028

(22) Filed: Aug. 16, 2019

(65) Prior Publication Data

US 2019/0366338 A1    Dec. 5, 2019

Related U.S. Application Data

(63) Continuation of application No. 13/120,504, filed as application No. PCT/US2009/058237 on Sep. 24, 2009, now Pat. No. 10,384,203.
(Continued)

(51) Int. Cl.
*B01L 3/00*      (2006.01)
*A61B 5/157*     (2006.01)
(Continued)

(52) U.S. Cl.
CPC ........ *B01L 3/502715* (2013.01); *A61B 5/157* (2013.01); *A61B 5/150022* (2013.01);
(Continued)

(58) Field of Classification Search
CPC .... G01N 21/75; G01N 33/543; G01N 27/745; B01J 2219/00328; B01J 2219/00324; B01J 2219/00315
See application file for complete search history.

(56) References Cited

U.S. PATENT DOCUMENTS

| 2,672,431 A | 3/1954 | Goetz |
| 2,761,813 A | 9/1956 | Goetz |

(Continued)

FOREIGN PATENT DOCUMENTS

| AU | 760425 B2 | 5/2003 |
| CN | 2486557 Y | 4/2002 |

(Continued)

OTHER PUBLICATIONS

Al-Hakiem, 1982, Development of Fluoroimmunoassays for the Determination of Individual or Combined Levels of Procainamide and N-Acetylprocainamide in Serum, J Immunoassay 3(1):91-110.
(Continued)

*Primary Examiner* — Jonathan M Hurst
(74) *Attorney, Agent, or Firm* — Ballard Spahr LLP

(57) ABSTRACT

The invention provides devices that improve tests for detecting specific cellular, viral, and molecular targets in clinical, industrial, or environmental samples. The invention permits efficient detection of individual microscopic targets at low magnification for highly sensitive testing. The invention does not require washing steps and thus allows sensitive and specific detection while simplifying manual operation and lowering costs and complexity in automated operation. In short, the invention provides devices that can deliver rapid, accurate, and quantitative, easy-to-use, and cost-effective tests.

12 Claims, 25 Drawing Sheets

A device with intermediate processing growth modules.
(Example 6)

Related U.S. Application Data

(60) Provisional application No. 61/099,830, filed on Sep. 24, 2008.

(51) Int. Cl.
| | |
|---|---|
| *G01N 21/03* | (2006.01) |
| *G01N 21/25* | (2006.01) |
| *G01N 21/64* | (2006.01) |
| *G01N 33/543* | (2006.01) |
| *A61B 5/15* | (2006.01) |
| *A61B 5/151* | (2006.01) |
| *B01L 7/00* | (2006.01) |
| *B01L 9/00* | (2006.01) |
| *A61B 5/117* | (2016.01) |

(52) U.S. Cl.
CPC ...... *A61B 5/15113* (2013.01); *A61B 5/15186* (2013.01); *A61B 5/150213* (2013.01); *A61B 5/150221* (2013.01); *A61B 5/150274* (2013.01); *A61B 5/150305* (2013.01); *A61B 5/150343* (2013.01); *A61B 5/150351* (2013.01); *A61B 5/150412* (2013.01); *A61B 5/150503* (2013.01); *A61B 5/150786* (2013.01); *B01L 3/5029* (2013.01); *B01L 3/5082* (2013.01); *B01L 3/502761* (2013.01); *G01N 21/03* (2013.01); *G01N 21/253* (2013.01); *G01N 21/6452* (2013.01); *G01N 21/6458* (2013.01); *G01N 33/54373* (2013.01); *A61B 5/117* (2013.01); *A61B 5/151* (2013.01); *B01L 7/00* (2013.01); *B01L 9/52* (2013.01); *B01L 2200/025* (2013.01); *B01L 2200/026* (2013.01); *B01L 2200/027* (2013.01); *B01L 2200/0605* (2013.01); *B01L 2200/10* (2013.01); *B01L 2300/022* (2013.01); *B01L 2300/042* (2013.01); *B01L 2300/043* (2013.01); *B01L 2300/046* (2013.01); *B01L 2300/048* (2013.01); *B01L 2300/0654* (2013.01); *B01L 2300/0681* (2013.01); *B01L 2300/0864* (2013.01); *B01L 2400/043* (2013.01); *B01L 2400/0406* (2013.01); *B01L 2400/0409* (2013.01); *B01L 2400/0415* (2013.01); *B01L 2400/0457* (2013.01); *B01L 2400/0472* (2013.01); *B01L 2400/0481* (2013.01); *B01L 2400/0677* (2013.01); *B01L 2400/0683* (2013.01); *G01N 21/6428* (2013.01); *G01N 2021/0325* (2013.01); *G01N 2021/0346* (2013.01)

(56) References Cited

U.S. PATENT DOCUMENTS

| | | |
|---|---|---|
| 3,694,317 A | 9/1972 | Scher |
| 3,981,776 A | 9/1976 | Saxholm |
| 4,097,586 A | 6/1978 | Gross |
| 4,098,876 A | 7/1978 | Piasio et al. |
| 4,115,535 A | 9/1978 | Giaever |
| 4,125,375 A | 11/1978 | Hunter |
| 4,129,419 A | 12/1978 | Hermann, Jr. |
| 4,141,687 A | 2/1979 | Forrest et al. |
| 4,157,323 A | 6/1979 | Yen et al. |
| 4,177,253 A | 12/1979 | Davies et al. |
| 4,222,744 A | 9/1980 | McConnell |
| 4,436,826 A | 3/1984 | Wang |
| 4,438,068 A | 3/1984 | Forrest |
| 4,454,233 A | 6/1984 | Wang |
| 4,455,370 A | 6/1984 | Bartelsman et al. |
| 4,477,578 A | 10/1984 | Miles et al. |
| 4,537,861 A | 8/1985 | Elings et al. |
| 4,562,157 A | 12/1985 | Lowe et al. |
| 4,565,783 A | 1/1986 | Hansen et al. |
| 4,582,810 A | 4/1986 | Rosenstein |
| 4,587,213 A | 5/1986 | Malecki |
| 4,614,585 A | 9/1986 | Mehra et al. |
| 4,693,972 A | 9/1987 | Mansour et al. |
| 4,731,337 A | 3/1988 | Luotola et al. |
| 4,745,077 A | 5/1988 | Holian et al. |
| 4,750,820 A | 6/1988 | Pareigat |
| 4,777,137 A | 10/1988 | Lemonnier |
| 4,777,145 A | 10/1988 | Luotola et al. |
| 4,912,037 A | 3/1990 | Lemonnier |
| 4,922,092 A | 5/1990 | Rushbrooke et al. |
| 4,959,301 A | 9/1990 | Weaver et al. |
| 4,981,783 A | 1/1991 | Augenlicht |
| 4,988,302 A | 1/1991 | Smith et al. |
| 4,988,618 A | 1/1991 | Li et al. |
| 5,073,497 A | 12/1991 | Schwartz |
| 5,089,413 A | 2/1992 | Nelson et al. |
| 5,130,733 A | 7/1992 | Taniguchi et al. |
| 5,137,812 A | 8/1992 | Matner |
| 5,190,666 A | 3/1993 | Bisconte |
| 5,232,838 A | 8/1993 | Nelson et al. |
| 5,238,810 A | 8/1993 | Fujiwara et al. |
| 5,258,284 A | 11/1993 | Morris, Jr. et al. |
| 5,262,526 A | 11/1993 | Sasamoto et al. |
| 5,292,644 A | 3/1994 | Berg |
| 5,306,420 A | 4/1994 | Bisconte |
| 5,321,545 A | 6/1994 | Bisconte |
| 5,348,885 A | 9/1994 | Labarthe |
| 5,355,215 A | 10/1994 | Schroeder et al. |
| 5,366,867 A | 11/1994 | Kawakami et al. |
| 5,464,749 A | 11/1995 | Schwarzberg et al. |
| 5,474,910 A | 12/1995 | Alfano |
| 5,510,246 A | 4/1996 | Morgan |
| 5,538,857 A | 7/1996 | Rosenthal et al. |
| 5,541,069 A | 7/1996 | Mortensen et al. |
| 5,552,272 A | 9/1996 | Bogart |
| 5,558,839 A | 9/1996 | Matte et al. |
| 5,582,982 A | 12/1996 | Cubbage et al. |
| 5,585,241 A | 12/1996 | Lindmo |
| 5,604,351 A | 2/1997 | Bisconte |
| 5,606,413 A | 2/1997 | Bellus et al. |
| 5,624,850 A | 4/1997 | Kumar et al. |
| 5,652,939 A | 7/1997 | Verlinden et al. |
| 5,653,939 A | 8/1997 | Hollis et al. |
| 5,663,057 A | 9/1997 | Drocourt et al. |
| 5,672,880 A | 9/1997 | Kain |
| 5,681,530 A | 10/1997 | Kuster et al. |
| 5,681,712 A | 10/1997 | Nelson |
| 5,694,478 A | 12/1997 | Braier et al. |
| 5,705,402 A | 1/1998 | Leland et al. |
| 5,736,405 A | 4/1998 | Mfano et al. |
| 5,744,322 A | 4/1998 | Krejcarek et al. |
| 5,766,868 A | 6/1998 | Seto |
| 5,792,617 A | 8/1998 | Rotman |
| 5,814,454 A | 9/1998 | Ju |
| 5,821,066 A | 10/1998 | Pyle et al. |
| 5,828,716 A | 10/1998 | Bisconte de Saint Julien |
| 5,852,498 A | 12/1998 | Youvan et al. |
| 5,861,251 A | 1/1999 | Park et al. |
| 5,861,270 A | 1/1999 | Nelis |
| 5,861,306 A | 1/1999 | Pugh et al. |
| 5,891,394 A | 4/1999 | Drocourt et al. |
| 5,914,245 A | 6/1999 | Bylina et al. |
| 5,958,790 A | 9/1999 | Cerny |
| 5,968,766 A | 10/1999 | Powers |
| 5,976,892 A | 11/1999 | Bisconte |
| 5,981,180 A | 11/1999 | Chandler et al. |
| 5,985,675 A | 11/1999 | Charm et al. |
| 5,989,835 A | 11/1999 | Dunlay et al. |
| 5,993,740 A | 11/1999 | Niiyama et al. |
| 6,048,723 A | 4/2000 | Banes |
| 6,051,393 A | 4/2000 | Jones et al. |
| 6,051,395 A | 4/2000 | Rocco |
| 6,121,055 A | 9/2000 | Hargreaves |
| 6,122,396 A | 9/2000 | King et al. |
| 6,130,931 A | 10/2000 | Laurila et al. |
| 6,140,653 A | 10/2000 | Che |

(56) References Cited

U.S. PATENT DOCUMENTS

| | | |
|---|---|---|
| 6,165,742 A | 12/2000 | .O slashed.fjord et al. |
| 6,171,780 B1 | 1/2001 | Pham et al. |
| 6,200,762 B1 | 3/2001 | Zlokarnik et al. |
| 6,214,560 B1 | 4/2001 | Yguerabide et al. |
| 6,258,326 B1 | 7/2001 | Modlin |
| 6,259,807 B1 | 7/2001 | Ravkin |
| 6,268,222 B1 | 7/2001 | Chandler et al. |
| 6,274,384 B1 | 8/2001 | Starzl et al. |
| 6,287,849 B1 | 9/2001 | McNerney et al. |
| 6,306,589 B1 | 10/2001 | Muller et al. |
| 6,309,822 B1 | 10/2001 | Fodor et al. |
| 6,345,115 B1 | 2/2002 | Ramm et al. |
| 6,358,730 B1 | 3/2002 | Kane |
| 6,472,166 B1 | 10/2002 | Wardlaw et al. |
| 6,582,912 B1 | 6/2003 | Rousseau et al. |
| 6,602,704 B1 | 8/2003 | Maxwell et al. |
| 6,623,983 B1 | 9/2003 | Terstappen et al. |
| 6,664,528 B1 | 12/2003 | Cartlidge et al. |
| 6,710,879 B1 | 3/2004 | Hansen et al. |
| 6,727,071 B1 | 4/2004 | Dunlay et al. |
| 6,764,648 B1 | 7/2004 | Roach et al. |
| 6,790,655 B2 | 9/2004 | Lyman et al. |
| 6,792,132 B1 | 9/2004 | Hara et al. |
| 6,852,527 B2 | 2/2005 | Chan et al. |
| 6,919,960 B2 | 7/2005 | Hansen et al. |
| 6,969,607 B2 | 11/2005 | Minton |
| 7,068,365 B2 | 6/2006 | Hansen et al. |
| 7,110,585 B2 | 9/2006 | Cork et al. |
| 7,160,687 B1 | 1/2007 | Kapur et al. |
| 7,582,415 B2 | 9/2009 | Straus |
| 7,763,405 B2 | 7/2010 | Wu et al. |
| 7,763,455 B2 | 7/2010 | Cima et al. |
| 7,820,430 B2 | 10/2010 | Weng et al. |
| 3,021,848 A1 | 9/2011 | Straus |
| 9,090,462 B2 | 7/2015 | Straus |
| 9,290,382 B2 | 3/2016 | Straus |
| 2001/0039060 A1 | 11/2001 | Siiman et al. |
| 2002/0028471 A1 | 3/2002 | Oberhardt |
| 2002/0055092 A1 | 5/2002 | Hochman |
| 2002/0137106 A1 | 9/2002 | Leung et al. |
| 2003/0068072 A1 | 4/2003 | Cork et al. |
| 2003/0082516 A1 | 5/2003 | Straus |
| 2003/0143580 A1 | 7/2003 | Straus |
| 2003/0170613 A1 | 9/2003 | Straus |
| 2004/0048395 A1 | 3/2004 | Lee et al. |
| 2004/0171121 A1 | 9/2004 | Leppla et al. |
| 2004/0172000 A1 | 9/2004 | Roe et al. |
| 2004/0246483 A1 | 12/2004 | Hansen et al. |
| 2005/0013737 A1 | 1/2005 | Chow et al. |
| 2005/0148085 A1 | 7/2005 | Larsen |
| 2005/0153430 A1 | 7/2005 | Ohtaka |
| 2005/0191687 A1 | 9/2005 | Wang et al. |
| 2005/0220670 A1 | 10/2005 | Palmieri et al. |
| 2005/0221403 A1 | 10/2005 | Gazenko |
| 2005/0225766 A1 | 10/2005 | Hansen et al. |
| 2005/0226779 A1 | 10/2005 | Oldham et al. |
| 2006/0006067 A1 | 1/2006 | Unger |
| 2006/0051816 A1 | 3/2006 | Hsieh et al. |
| 2006/0121055 A1 | 6/2006 | Campbell et al. |
| 2006/0129327 A1 | 6/2006 | Kim et al. |
| 2006/0188967 A1 | 8/2006 | Nalin et al. |
| 2006/0210435 A1 | 9/2006 | Alavie et al. |
| 2006/0216696 A1 | 9/2006 | Goguen |
| 2006/0256340 A1 | 11/2006 | Hansen et al. |
| 2006/0292552 A1 | 12/2006 | Haquette et al. |
| 2007/0014695 A1 | 1/2007 | Yue et al. |
| 2007/0172899 A1 | 7/2007 | Graham et al. |
| 2007/0184546 A1 | 8/2007 | Farrelly et al. |
| 2007/0212681 A1 | 9/2007 | Shapiro et al. |
| 2007/0212747 A1 | 9/2007 | Browne et al. |
| 2008/0003571 A1 | 1/2008 | McKernan et al. |
| 2008/0014576 A1 | 1/2008 | Jovanovich et al. |
| 2008/0032328 A1 | 2/2008 | Cline et al. |
| 2008/0038738 A1 | 2/2008 | Weigum et al. |
| 2008/0200343 A1 | 8/2008 | Clemens et al. |
| 2008/0206099 A1 | 8/2008 | Aruga et al. |
| 2009/0137029 A1 | 5/2009 | Breidenthal et al. |
| 2009/0315987 A1 | 12/2009 | Straus |
| 2010/0028986 A1 | 2/2010 | Hanafusa |
| 2010/0248281 A1 | 9/2010 | Straus |
| 2012/0046203 A1 | 2/2012 | Walsh et al. |
| 2012/0149007 A1 | 6/2012 | Abrams et al. |
| 2013/0011566 A1 | 1/2013 | Colin et al. |
| 2017/0029864 A1 | 2/2017 | Straus |

FOREIGN PATENT DOCUMENTS

| | | |
|---|---|---|
| CN | 101254482 A | 9/2008 |
| DE | 19608320 A1 | 8/1997 |
| DE | 19631997 A1 | 2/1998 |
| DE | 19940810 A1 | 5/2000 |
| EP | 0171174 A2 | 2/1986 |
| EP | 0574977 A1 | 12/1993 |
| EP | 0753732 A2 | 1/1997 |
| EP | 1207394 A2 | 5/2002 |
| EP | 1508374 A2 | 2/2005 |
| JP | S62-501647 A | 7/1987 |
| JP | H02-502405 A | 8/1990 |
| JP | H02-278155 A | 11/1990 |
| JP | H3-83598 | 4/1991 |
| JP | 08-201391 A | 8/1996 |
| JP | 10295362 | 11/1998 |
| JP | H11-148901 A | 6/1999 |
| JP | H11-346795 A | 12/1999 |
| JP | 2000-508778 A | 7/2000 |
| JP | 2000-509827 A | 8/2000 |
| JP | 2000-275258 A | 10/2000 |
| JP | 3102240 B2 | 10/2000 |
| JP | 2001-224355 A | 8/2001 |
| JP | 2001-512875 A | 8/2001 |
| JP | 2002-125656 A | 5/2002 |
| JP | 2003-294596 A | 10/2003 |
| JP | 2004-070039 A | 3/2004 |
| JP | 2004-125799 A | 4/2004 |
| JP | 2005-502354 A | 1/2005 |
| JP | 2006-087336 A | 4/2006 |
| JP | 2006-162466 A | 6/2006 |
| JP | 2007-526807 A | 9/2007 |
| JP | 2008-96223 A | 4/2008 |
| JP | 2008-513022 A | 5/2008 |
| JP | 2009-513111 A | 4/2009 |
| WO | 83/01581 A1 | 5/1983 |
| WO | 86/04684 A1 | 8/1986 |
| WO | 89/05456 A1 | 6/1989 |
| WO | 92/05448 A2 | 4/1992 |
| WO | 97/40181 A1 | 10/1997 |
| WO | 97/44664 A1 | 11/1997 |
| WO | 98/38490 A1 | 9/1998 |
| WO | 98/50577 A1 | 11/1998 |
| WO | 99/08233 A1 | 2/1999 |
| WO | 99/20789 A1 | 4/1999 |
| WO | 99/35483 A1 | 7/1999 |
| WO | 99/36577 A1 | 7/1999 |
| WO | 99/40176 A1 | 8/1999 |
| WO | 99/58948 A2 | 11/1999 |
| WO | 00/04382 A1 | 1/2000 |
| WO | 00/47766 A1 | 8/2000 |
| WO | 01/57522 A2 | 8/2001 |
| WO | 01/61348 A1 | 8/2001 |
| WO | 03/022999 A2 | 3/2003 |
| WO | 03/036290 A1 | 5/2003 |
| WO | 03/073817 A2 | 9/2003 |
| WO | 2005/082254 A2 | 9/2005 |
| WO | 2006/032044 A2 | 3/2006 |
| WO | 2006/106962 A1 | 10/2006 |
| WO | 2007/038478 A2 | 4/2007 |
| WO | 2007/145091 A1 | 12/2007 |
| WO | 2008/005998 A2 | 1/2008 |
| WO | 2008108027 A1 | 9/2008 |
| WO | 2010/036827 A1 | 4/2010 |
| WO | 2010/036829 A1 | 4/2010 |
| WO | 2011/117545 A1 | 9/2011 |

(56) References Cited

FOREIGN PATENT DOCUMENTS

WO  2013/070730 A2  5/2013
WO  2013/158666 A1  10/2013

OTHER PUBLICATIONS

Allman, 1981, Fluoroimmunoassay of Progesterone in Human Serum of Plasma, Clin Chem 27:1176-1176.
Batchelor, 2012, Light and Optics, Machine Vision Handbook, Springer-Verlag, 157-258.
Catalogue of Becton, 2003, Dickinson and Company, p. 28, 29, 32-35, 150 and 151, Japan.
CCD detectors (http://www.astrosurf.com/re/chip.html) published online Feb. 22, 2001, from web archive http://web.archive.org/web/20010222014106/http://astrosurf.com/re/chip.html, retrieved Apr. 12, 2012, 5 pages.
Clean Technology, 1995, 5(8):60-61 (no english translation provided).
Colony Counter (http://www.topac.com/acolyte.html), retrieved Apr. 12, 2005, 3 pages.
Colony Counter Models and Specifications (http://biologics-inc.com/cc-models.htm), retrieved Apr. 15, 2005, 3 pages.
Corkidi, 1998, COVASIAM: An Image Analysis Method That Allows Detection of Confluent Microbial Colonies and Colonies of Various Sizes for Automated Counting, Appl Environ Microbiol 64(4):1400-1404.
Crowther, 2000, Methods in Molecular Biology, The ELISA Guidebook, Humana Press, 425 pages.
Definition and Procedure for the Determination of the Method Detection Limit, Appendix B to 40 C.F.R. § 136, available at http://access.gpo.gov, retrieved Nov. 20, 2007, pp. 343-346.
Digital Multi-Purpose High Resolution Colony and Plaque Counter, http://www.loats.com/mla.html, retreived Apr. 12, 2005, 3 pages.
Esteban, 1992, Improved Direct Epifluorescent Filter Technique for Rapid Bioburden Control in Intravenous Solutions, J. Parenter. Sci. Technol. 46146-149.
Findlay, 1993, Automated closed-vessel sstem for in vitro diagnostics based on polymerase chain reation, Clin Chem, 39(9):1927-1933.
Freydiere, 1991, Detection of *Salmonellae* by using Rambach agar and by a C8 esterase spot test, J. Clin Microbiol. 29(10):2357-2360.
Frost, 1921, Improved Technic for the Micro or Little Plate Method of Counting Bacteria in Milk, J. Infect. Dis. 28 (2):176-187.
Gray, 2011, Identification of micro-organisms after milliflex rapid detection—a possibility to Identify nonsterile findings in the milliflex rapid sterility test, PDA J Pharm Sci Technol 65(1):42-54.
Graziani-Bowering, 1997, A quick and inexpensive method of the isolate of human peripheral blood monocytes, J. Immunol Methods, 207(2):157-168.
Innovative Plate Holder for ProtoCOL, http://www.synbiosis.com retrieved Oct. 16, 2002, 2 pages.
International Search Report and Written Opinion for International Application No. PCT/US2009/58237, dated Jan. 13, 2010, 10 pages.
Kamentsky, 2001, Laser Scanning Cytometry, Methods Cell Biol. 63:51-87.
Kepner, 1994, Use of fluorochromes fo direct enumeration of total bacteria in environmental samples: past and present, Microbiol Rev. 58(4):603-615.
Kroll, 1989, A Laser-Light Pulse Counting Method for Automatic and Sensitive Counting Of Bacteria Stained with Acridine Orange, J. Appl. Bacteriol. 66:161-167.
Lamture, 1994, Direct Detection of Nucleic Acid Hybridization on the Surface of a Charge Coupled Device, Nucleic Acids Res. 22(11):2121-2125.
Loates Associates Inc., 1999, System Specifications http://www.loats.com/order_info.html, retrieved Apr. 12, 2005, 7 pages.
Loats, 1990, LAI High-Resolution Automated Colony Counting System-Mouse Lymphoma Assay: Performance Analysis, http://loats.com/docs/HRCCval/HRCCval.htm, pp. 1-11.
Logtenberg, 1985, Enumeration of (Auto) Antibody Producing Cells in Human Using the "Spot-ELISA," Immunol. Lett. 9:343-347.
London, 2010, An Automated System for Rapid Non-Destructive Enumeration of Growing Microbes, PLoS One 5(1): e8609, 16 pages.
Masuko, 1991, A Novel Method for Detection and Counting of Single Bacteria in a Wide Field Using an Ultra-High-Sensitivity TV Camera Without a Microscope, FEMS Microbiol. Lett. 81:287-290.
Masuko, 1991, Rapid Detection and Counting of Single Bacteria in a Wide Field Using a Photon-Counting TV Camera, FEMS Microbiol. Lett. 83:231-238.
Mignon-Godefroy, 1997, Solid Phase Cytometry for Detection of Rare Events, Cytometry 27, pp. 336-344.
Miraglia, 1999, Homogeneous Cell-and Bead-Based Assays for High Throughput Screening Using Fluorometric Microvolume Assay Technology, J. Biomol. Screen. 4:193-204.
Moore, 1998, Lymphocyte fraction using immunomagnetic colloid and a dipole magnet flow cell sorter, J. Biochem. Biophys. Methods 37:11-33.
Margessi, 1980, Magnetizable Sold-Phase Fluoroimmunoassay of Thyroxines by a Sequential Addition Technique. Clin Chem 26(12):1701-1703.
Nargessi, 1984, Immunoassays for Serum C-Reactive Protein Employing Fluorophore-Labelled Reactants, J. Immunol. Methods 71:17-24.
Nealson, 1978, Isolation, identification, and manipulation of luminous bacteria, Methods Enzymol. 57:153-166.
Nebe-von-Caron, 2000, Analysis of bacterial function by multicolour fluorescence flow cytometry and single cell sorting, J. Microbiol Methods, 42(1):97-114.
Nelis, 2000, Enzymatic Detection of Coliforms and *Escherichia coli* Within 4 Hours, Water Air and Soil Pollut. 123:43-52.
Patterson, 1966, A wide angle camera for photographic search of the ocean bottom, SPIE, C-XII-1-8.
Perkinelmer, Inc., 2007, GeneScreenTM Hybridization Transfer Membranes: transfer and detection protocols, Application Notes, available at http://lasperkinelmer.com, retrieved Feb. 27, 2007.
Porter, 1980, The use of DAPI for identifying and counting aqquatic microflora, Limnol Oceanogr. 25(5):943-948.
Rousseau, 1999, New Miniaturized Highly Sensitive Immunassay Device for Quantitative Measurement of Soluble or Particular Antigen or Antibodies in a Liquid Sample, Clin. Chem. 45(9):1685-1687.
Schultz, 2000, Single Target Molecule Detection with Nonbleaching Multicolor Optical Immunolabels, Proc. Natl. Acad. Sci. USA 97(3):996-1001.
Sorcerer Automated Colony Counting, 2002, Perceptive Instruments, 2 pages.
Supplementary European Search Report and Written Opinion for European Application No. EP 09816857, dated Mar. 20, 2012, 8 pages.
Susa, 1998, Legionella Pneumophila Infection in Intratracheally Inoculated T Cell-Depleted or – Nondepleted A/J Mice, J. Immunol. 160:316-321.
Technical Specification http://www.perceptive.co.uk/products/_scc/techspec.html, retrieved Apr. 12, 2005, 2 pages.
Texas Instruments TC211 192x165 Pixel CCD Image Sensor description dated Jan. 1990, 13 pages.
Thomas, 2000, Making Gold Nanoparticles Glow: Enhanced Emission from a Surface-Bound Fluoroprobe, J. Am. Chem. Soc 122:2655-2656.
Tibbe, 1999, Optical Tracking and Detection of Immunomagnetically Selected and Aligned Cells, Nature Biotechnol. 17:1210-1213.
Van Pouche, 2000, A210-min Solid Phase Cytometry Test for the Enumeration of *Escherichia coli* in Drinking Water, J. Appl. Microbiol. 89:390-396.
Van Poucke, 1999, Solid Phase Cytometry-Based Enzymatic Detection of Coliforms in Drinking Water Within 4 h, Water Supply 17:67-72.
Van Poucke, 2000, Rapid Detection of Fluorescent and Chemiluminescent Total Coliforms and *Escherichia coli* on Membrane Filters J. Microbiol. Methods 42:233-214.

(56) References Cited

OTHER PUBLICATIONS

Vidon, 2001, A Simple Chemiluminescence-Based Method for Rapid Enumeration of *Listeria* spp. Microcolonies, J. Appl. Microbiol. 90:988-993.

Viinikka, 1981, A Two-Site Immunofluorometric Assay for Human Placental Lactogen, Clin. Chim. Acta. 114:1-9.

Waggoner, 1990, Fluorescent Probes for Cytometry, Flow Cytometry and Sorting, Wiley-Liss, 209-225.

Wellman, 2006, Magenetically-Assisted Transport Evanescent Field Fluoroimmunoassay, Anal, Chem. 78:4450-4456.

Wilson, 1995, Use of the IUL Countermat Automatic Colony Counter for Spiral Plated Total Viable Counts, Appl. Environ. Microbiol. 61:3158-3160.

Wolniak, 2004, BSCI 427 Principles of Microscopy Fall 2004 Syllabus, http://www.life.umd.edu/cbmg/faculty/wolniak/wolniakmicro.html, retrieved Nov. 8, 2007, 8 pages.

Yasui, 1997, Imaging of Lactobacillus brevis Single Cells and Microcolonies Without a Microscope by an Ultrasensitive Chemiluminescent Enzyme Immunoassay with a Photon-counting Television Camera, Appl. Environ. Microbiol. 63:4528-4533.

Zhao, 2004, Competitive Immunoassay for Microliter Protein Samples with Magnetic Beads and Near-infared Fluorescence Detection, Anal Chem. 76:1871-1876.

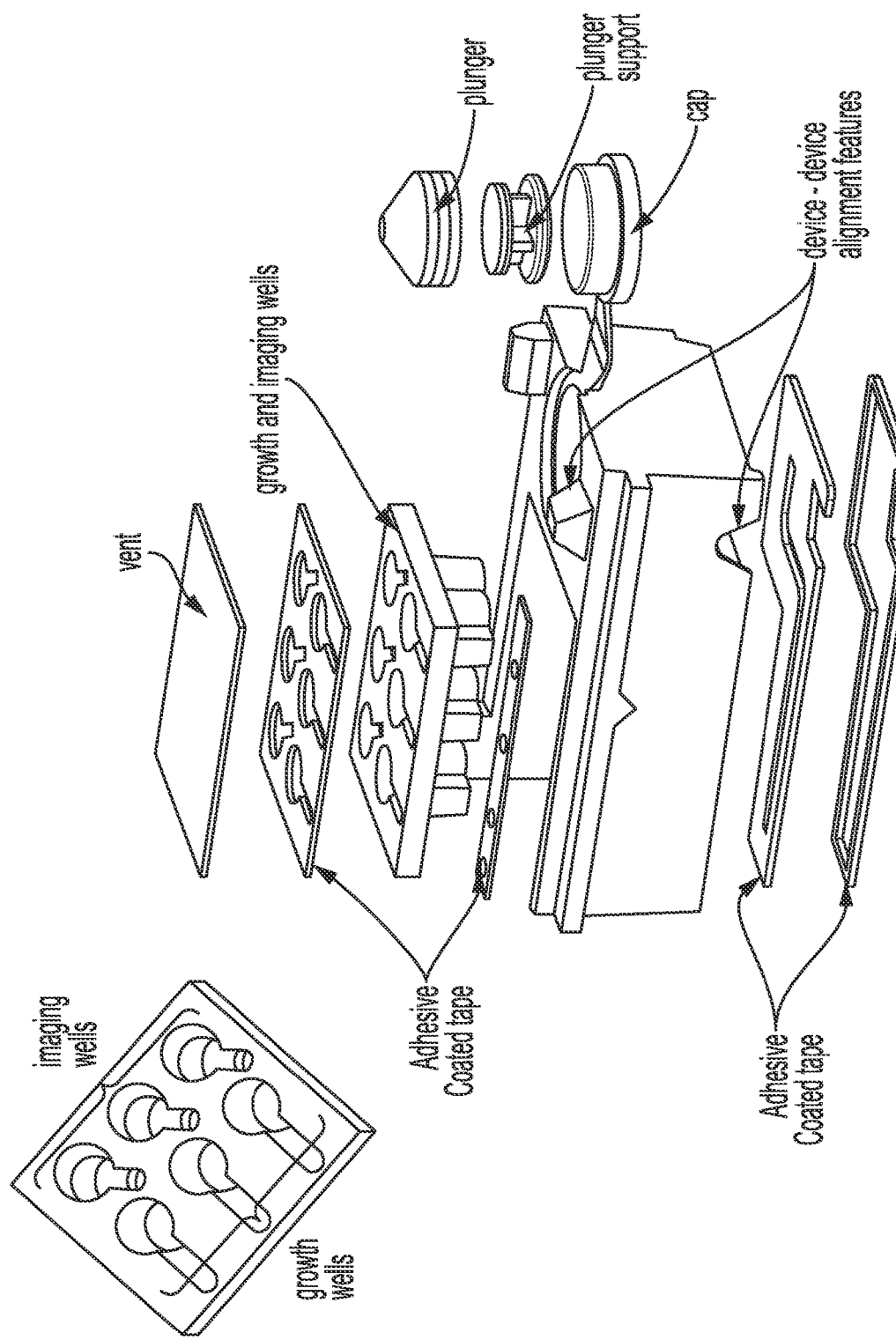
Fig. 1 Modular assembly of a device where sample is metered by actuation of a plunger integrated into the cap. (Example 6)

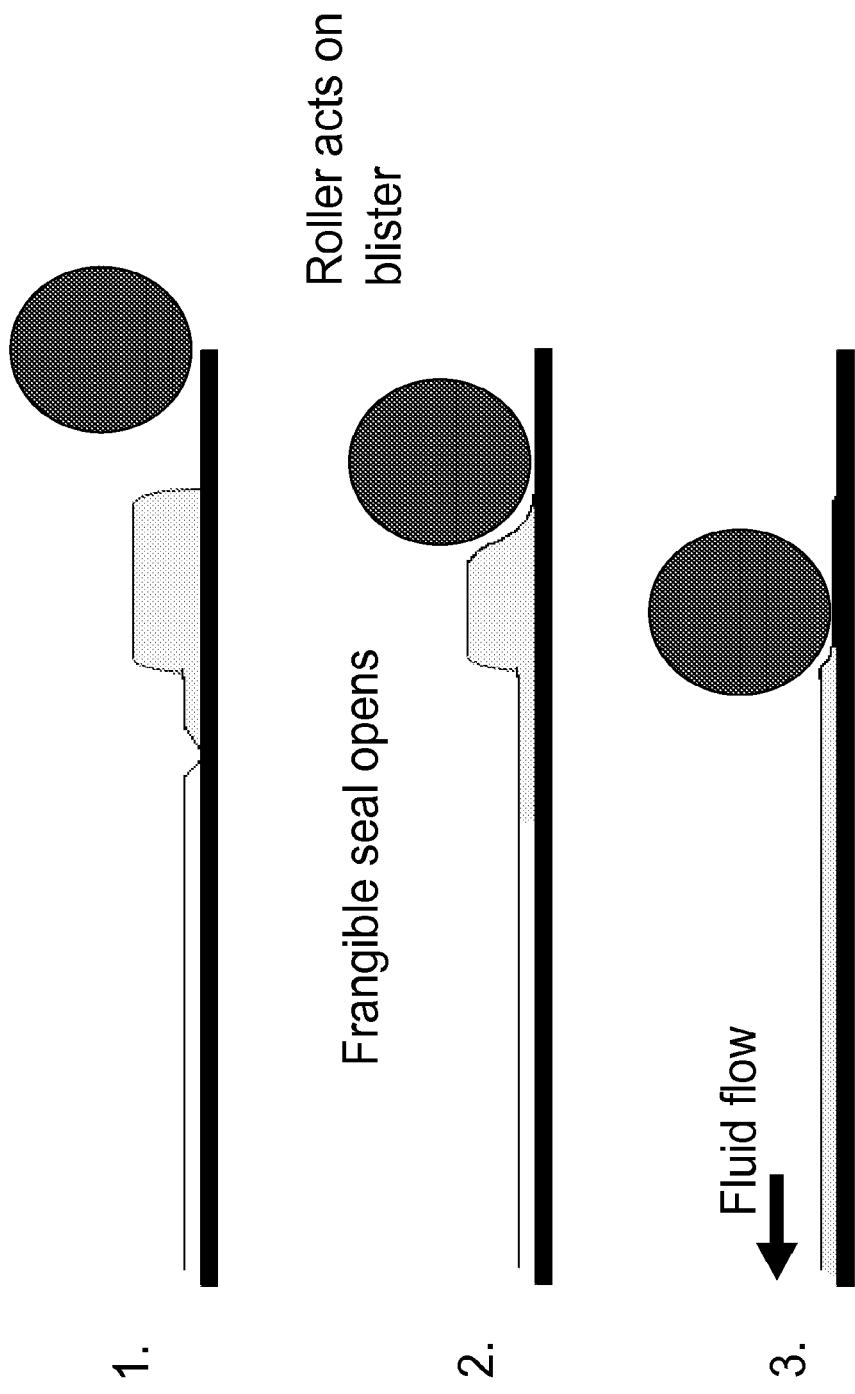
Fig. 2 Example of a deformable pouch with a frangible seal acted upon by a roller mechanism (Example 13).

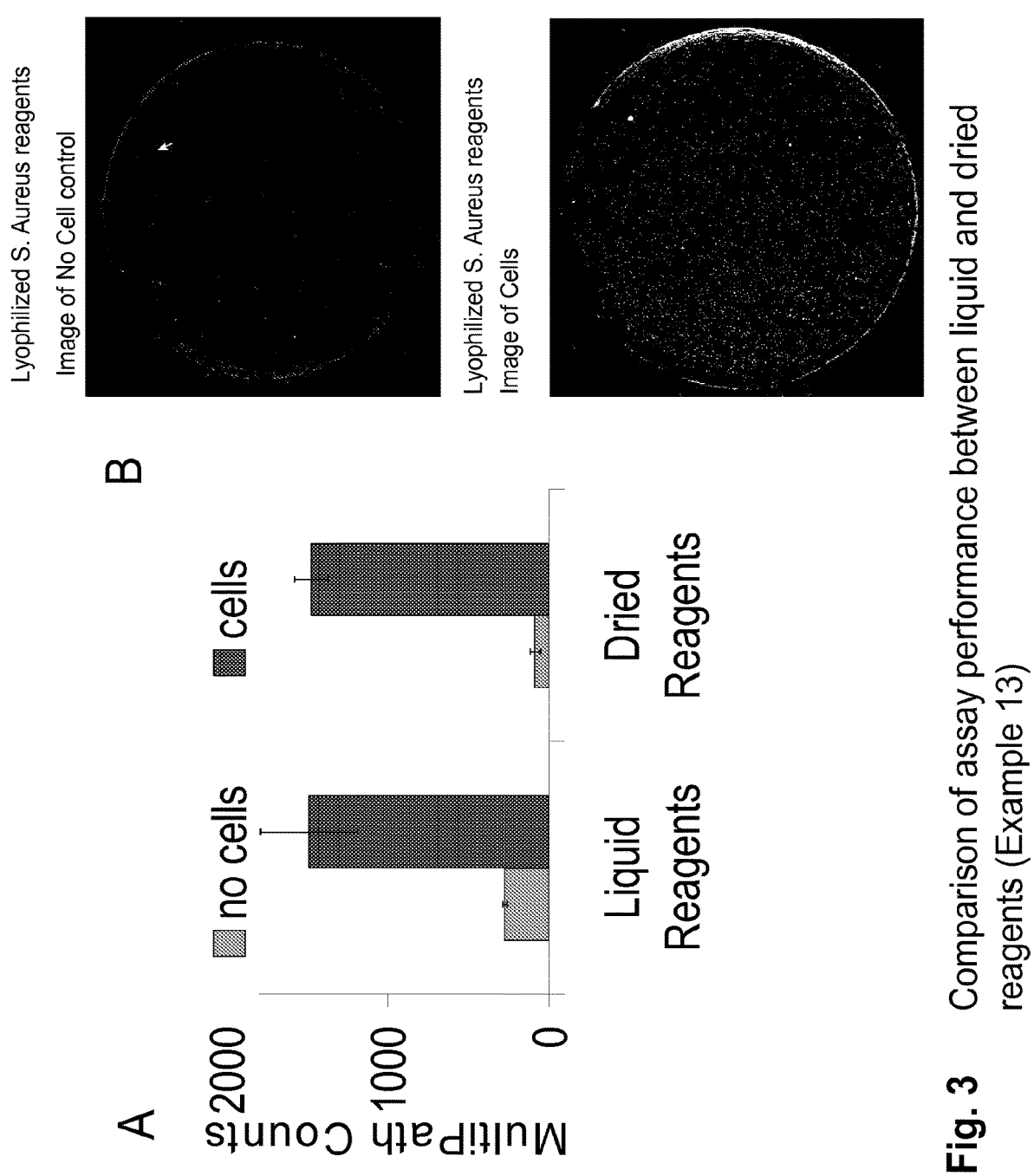
Fig. 3 Comparison of assay performance between liquid and dried reagents (Example 13)

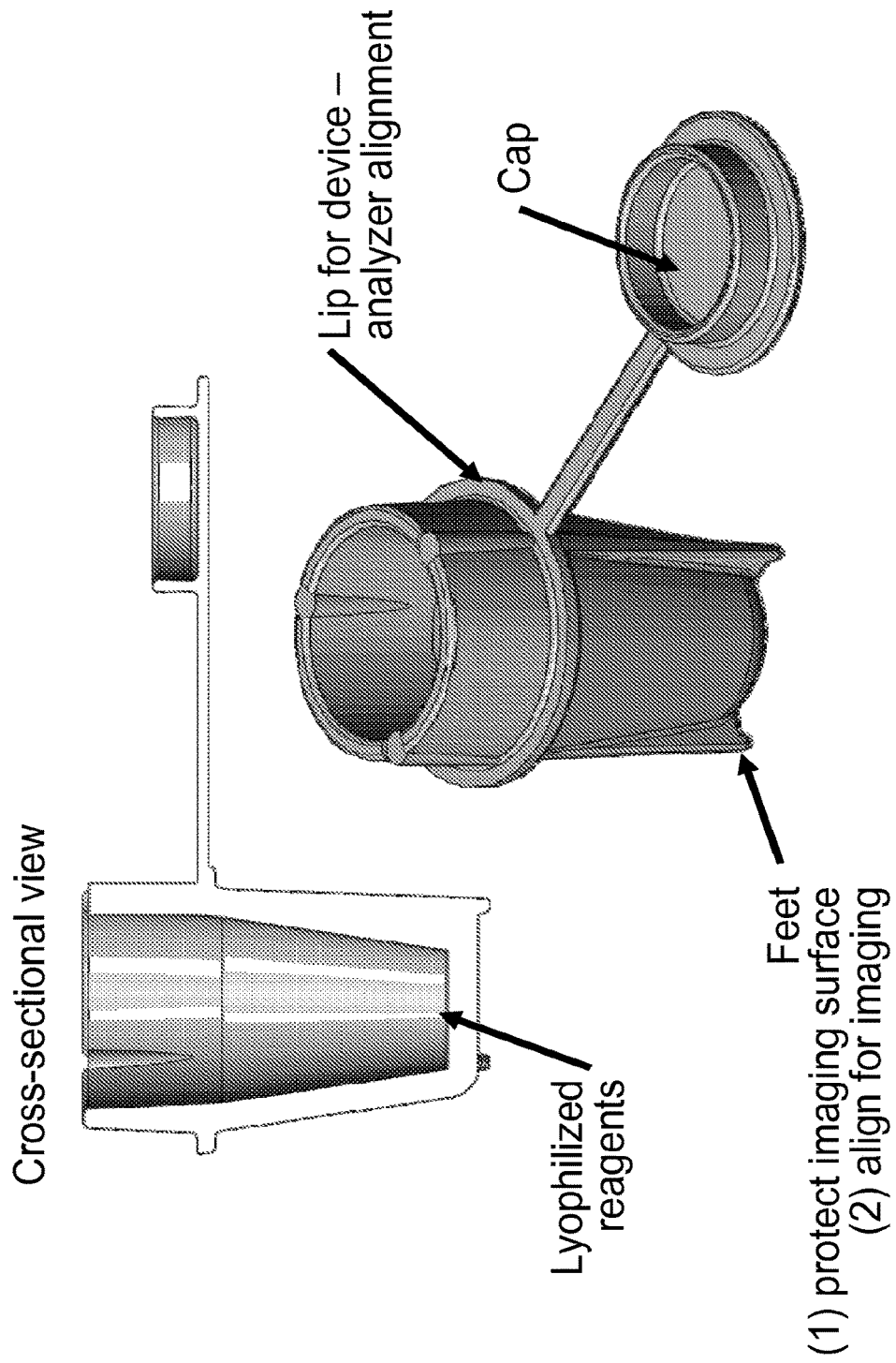
Fig. 4 A simple device that consists of a single vessel with dried reagents, a cap, and an imaging module. (Example 3)

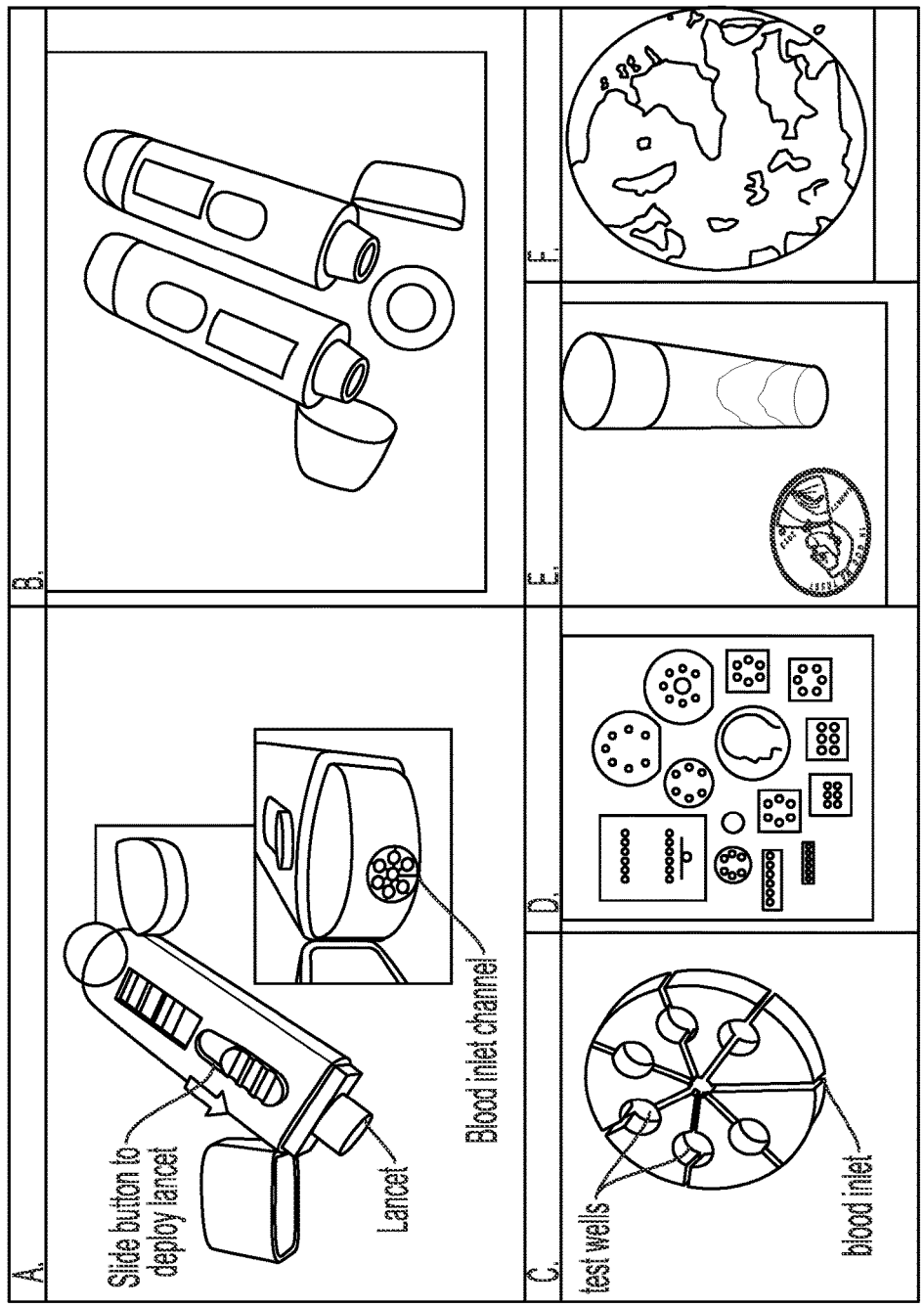
Fig. 5  A device that autonomously processes a single sample comprising an integrated sample collection function. (Examples 8, 9)

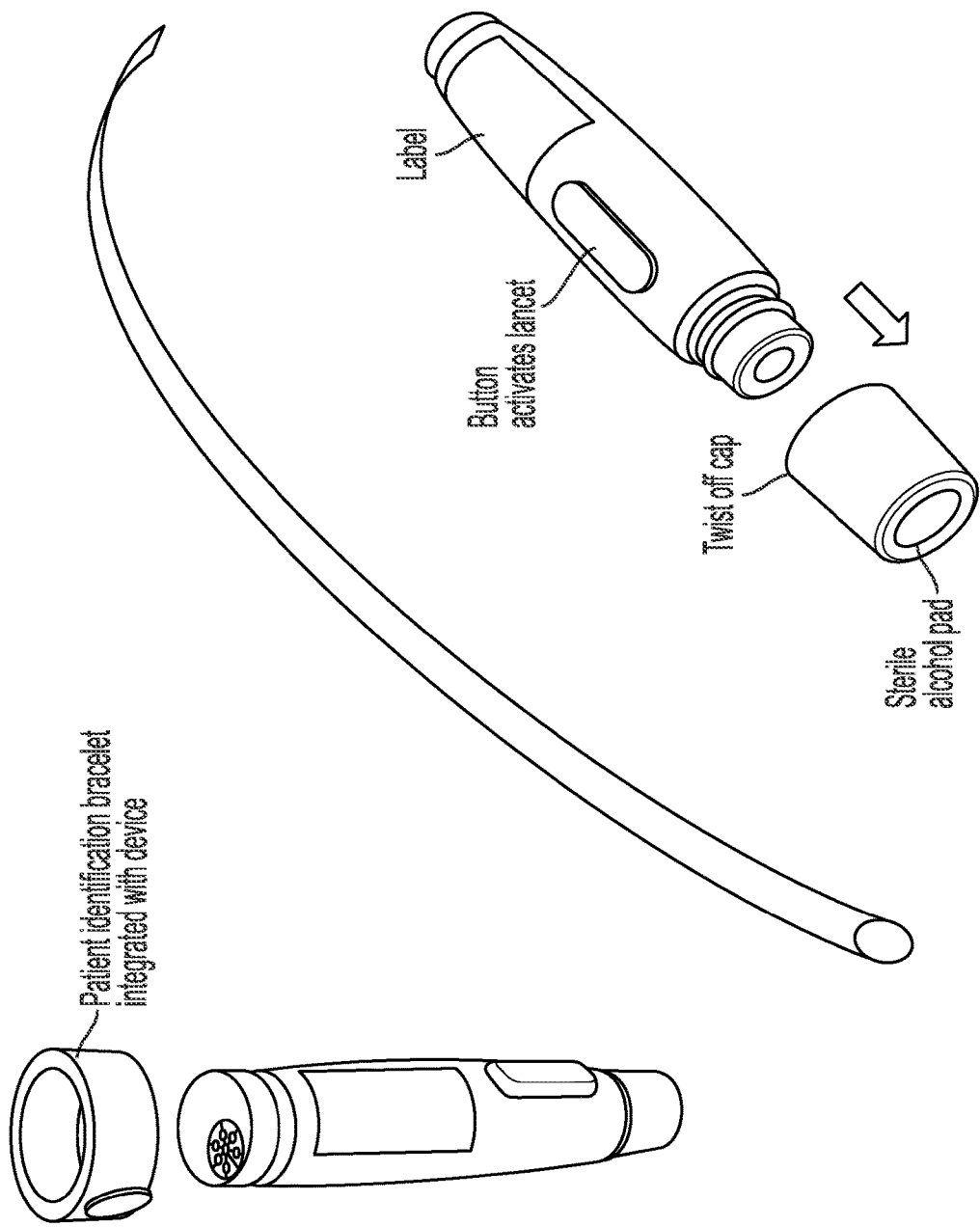
Fig. 6  Device with integrated sample collection modules (lancet and sterile alcohol pad in cap). (Example 9)

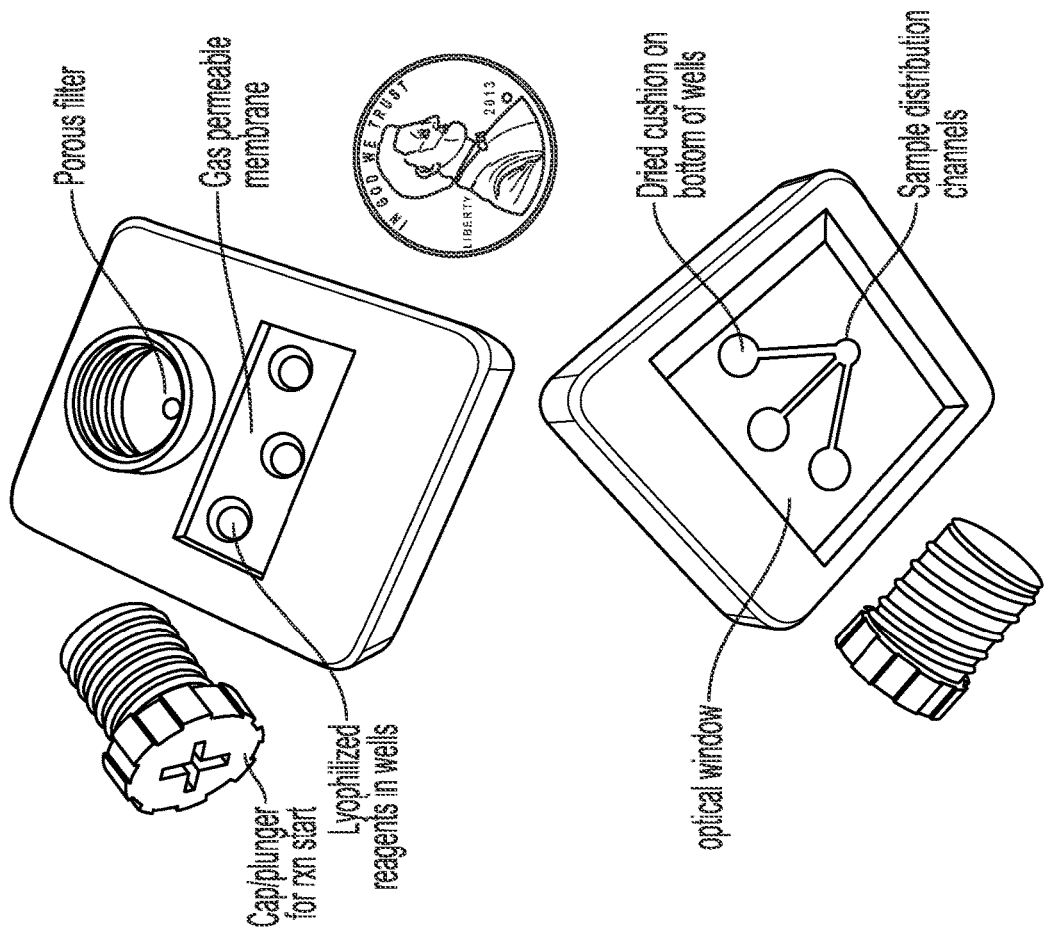
Fig. 7  A device with multiple reaction vessels where sample is metered by actuation of a screw cap. (Example 4)

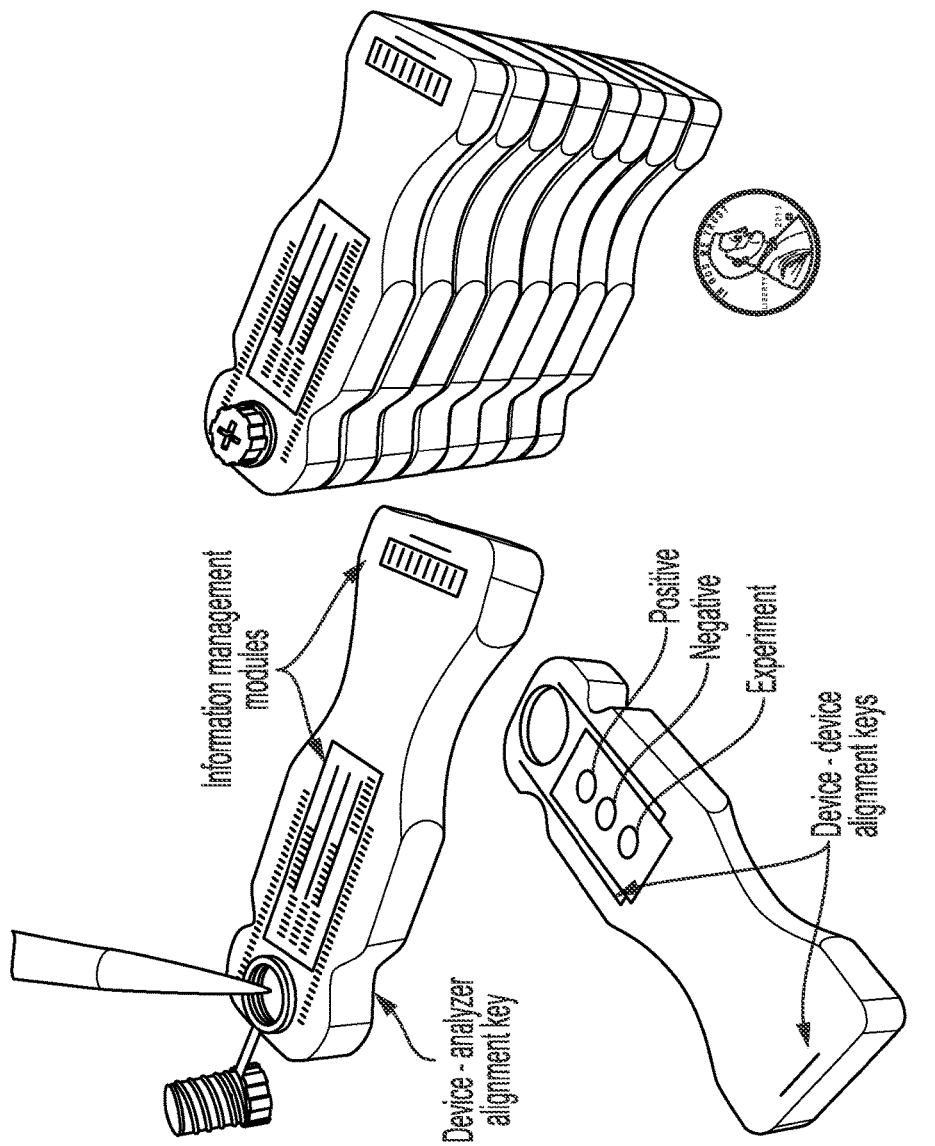
Fig. 8 A fully integrated device with multiple reaction vessels and alignment features for stacking and registration in an analyzer. (Example 5)

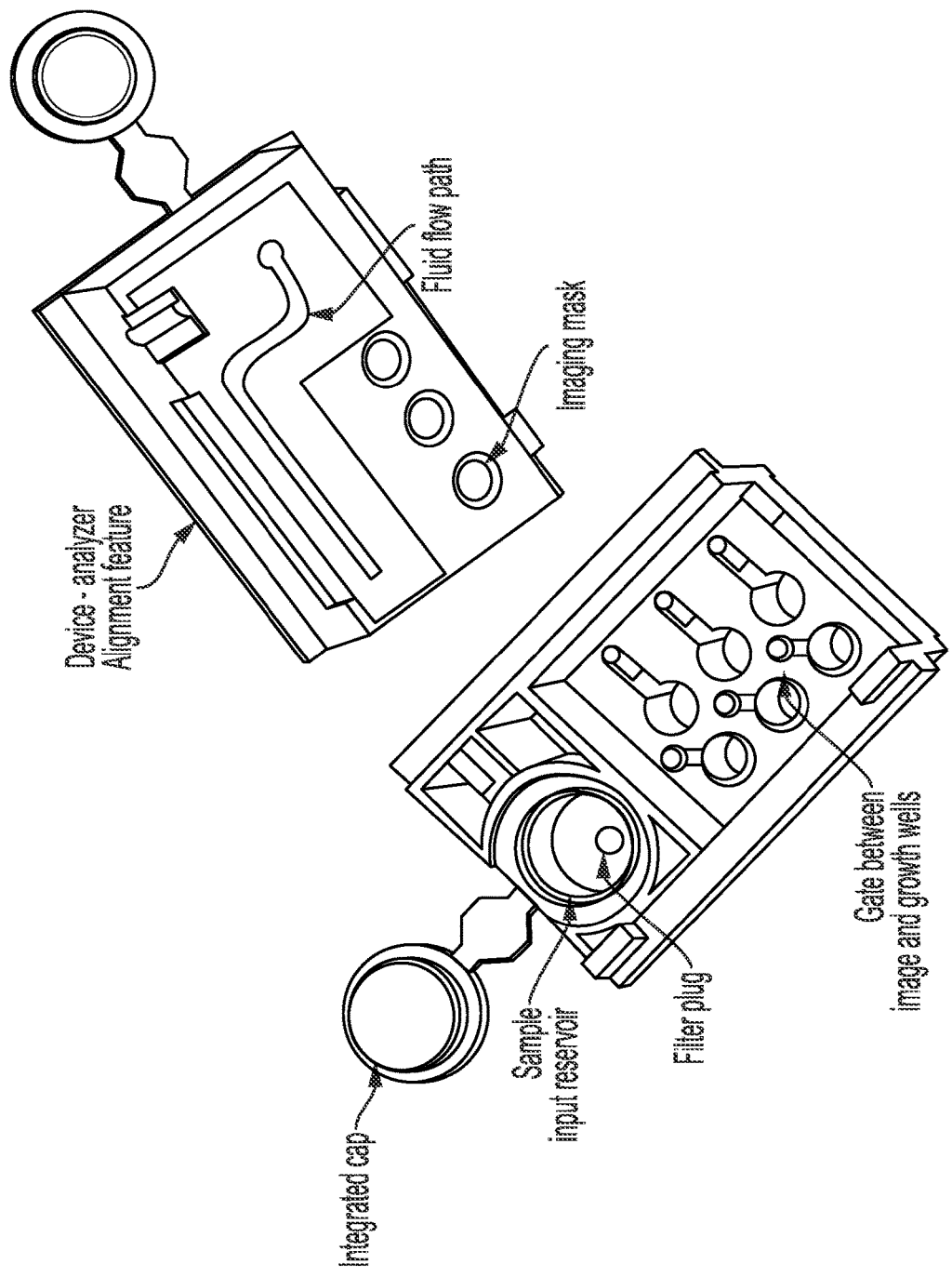
Fig. 9 A device with intermediate processing growth modules. (Example 6)

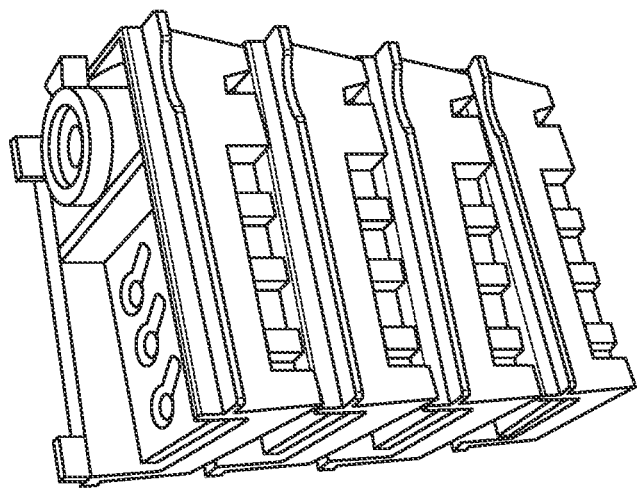
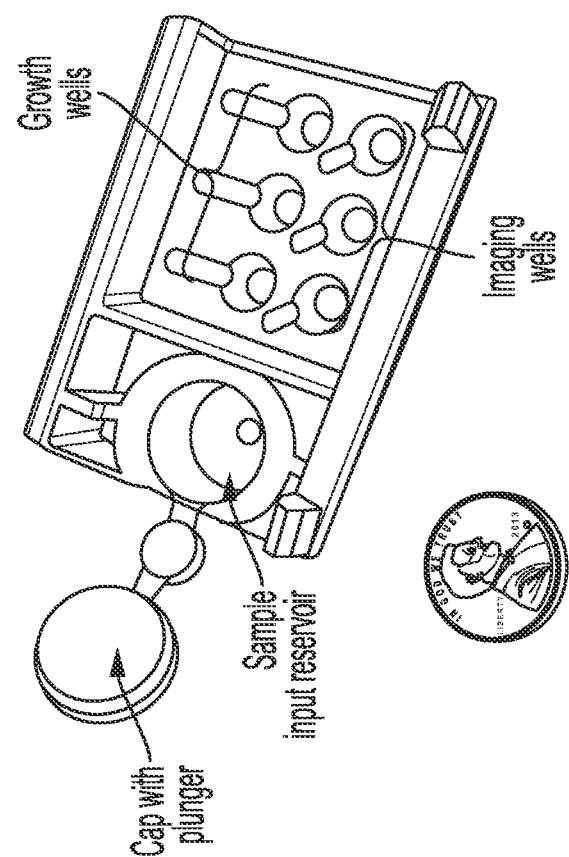
Fig. 10 Photograph of a stackable device with intermediate processing growth modules. (Example 6)

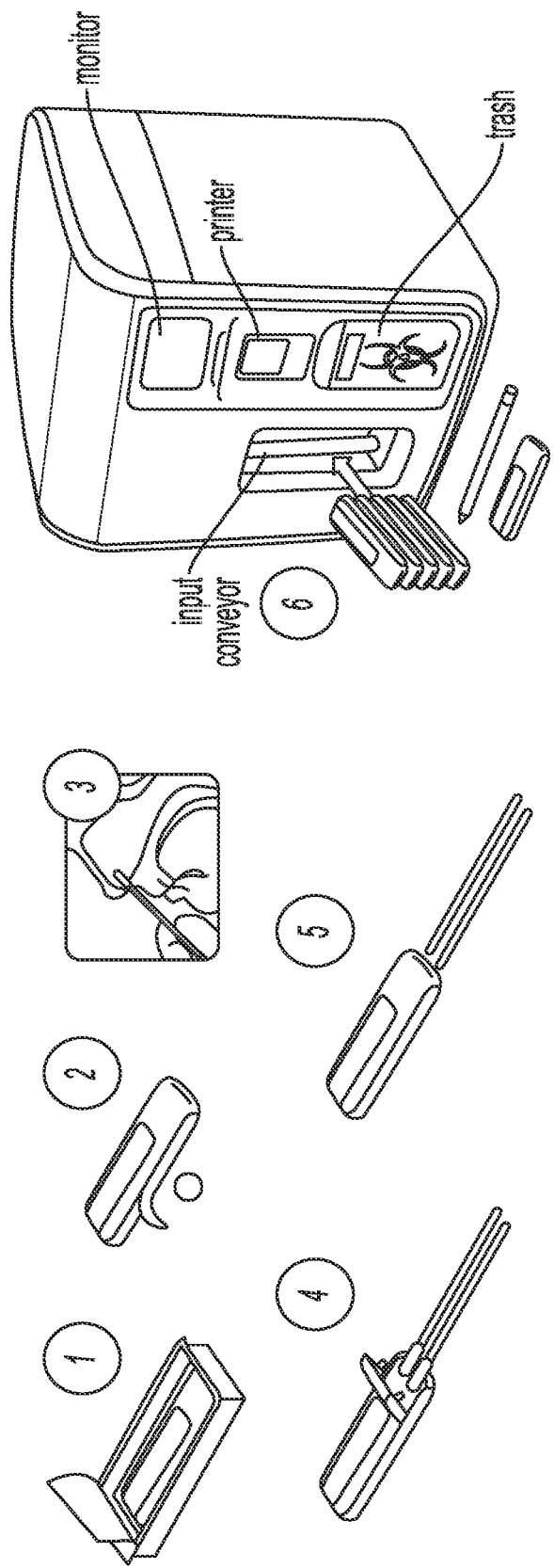
Fig. 11  Work flow of a fully integrated device that accepts direct insertion of sample swabs MRSA testing. (Example 7)

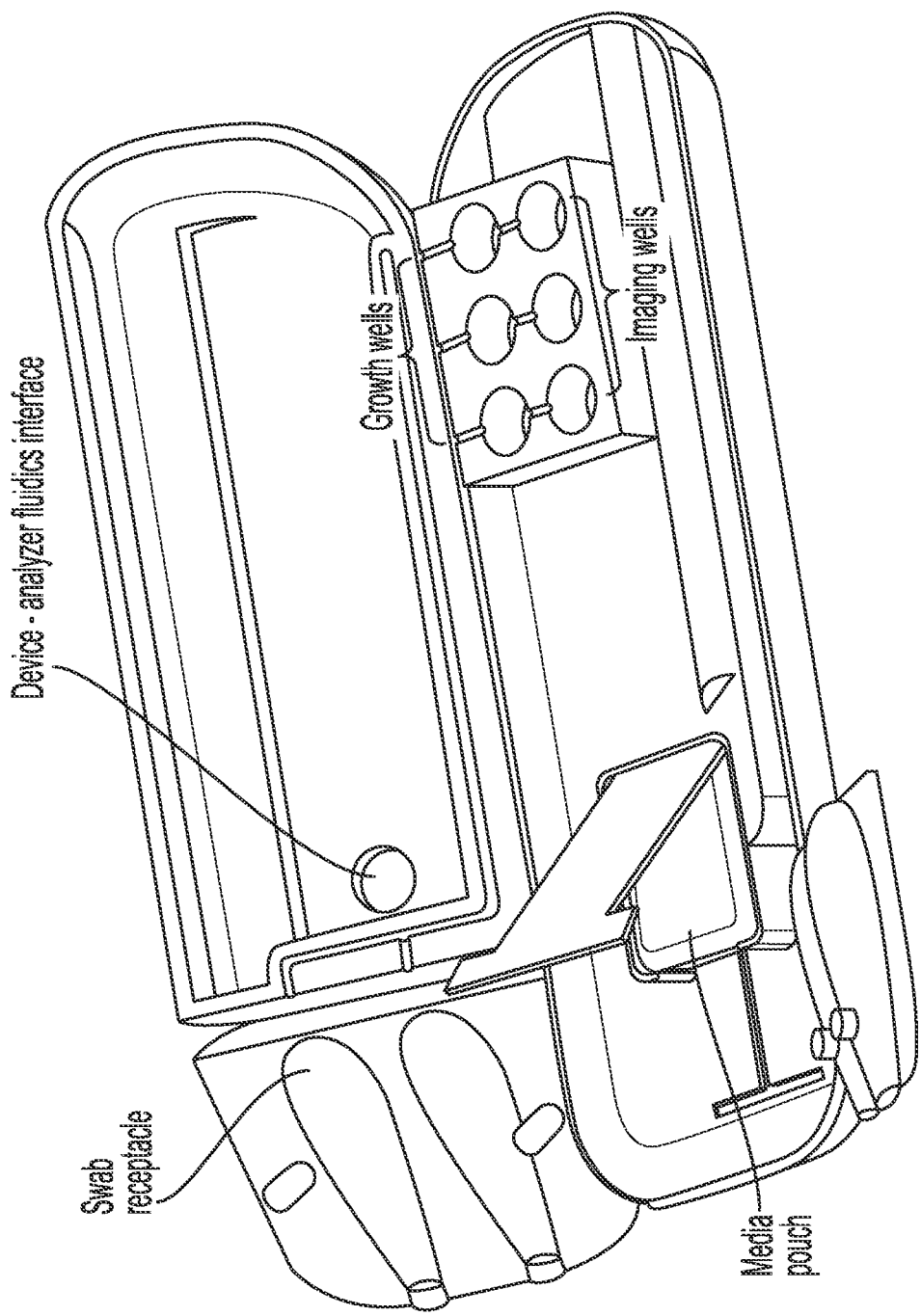
Fig. 12  Internal view of modules that comprise a fully integrated device that accepts direct insertion of sample swabs. (Example 7)

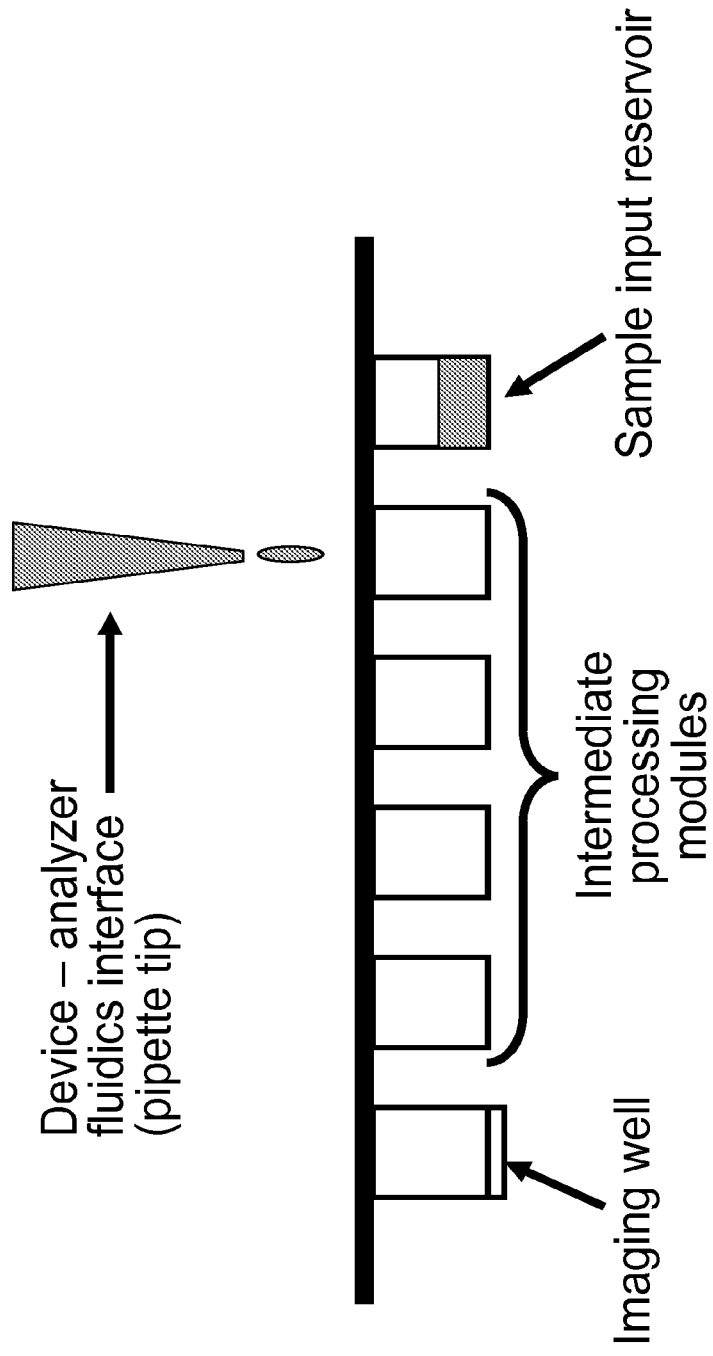
Fig. 13  Multiple self-contained vessels with integrated disposable pipette tips. (Examples 10, 11)

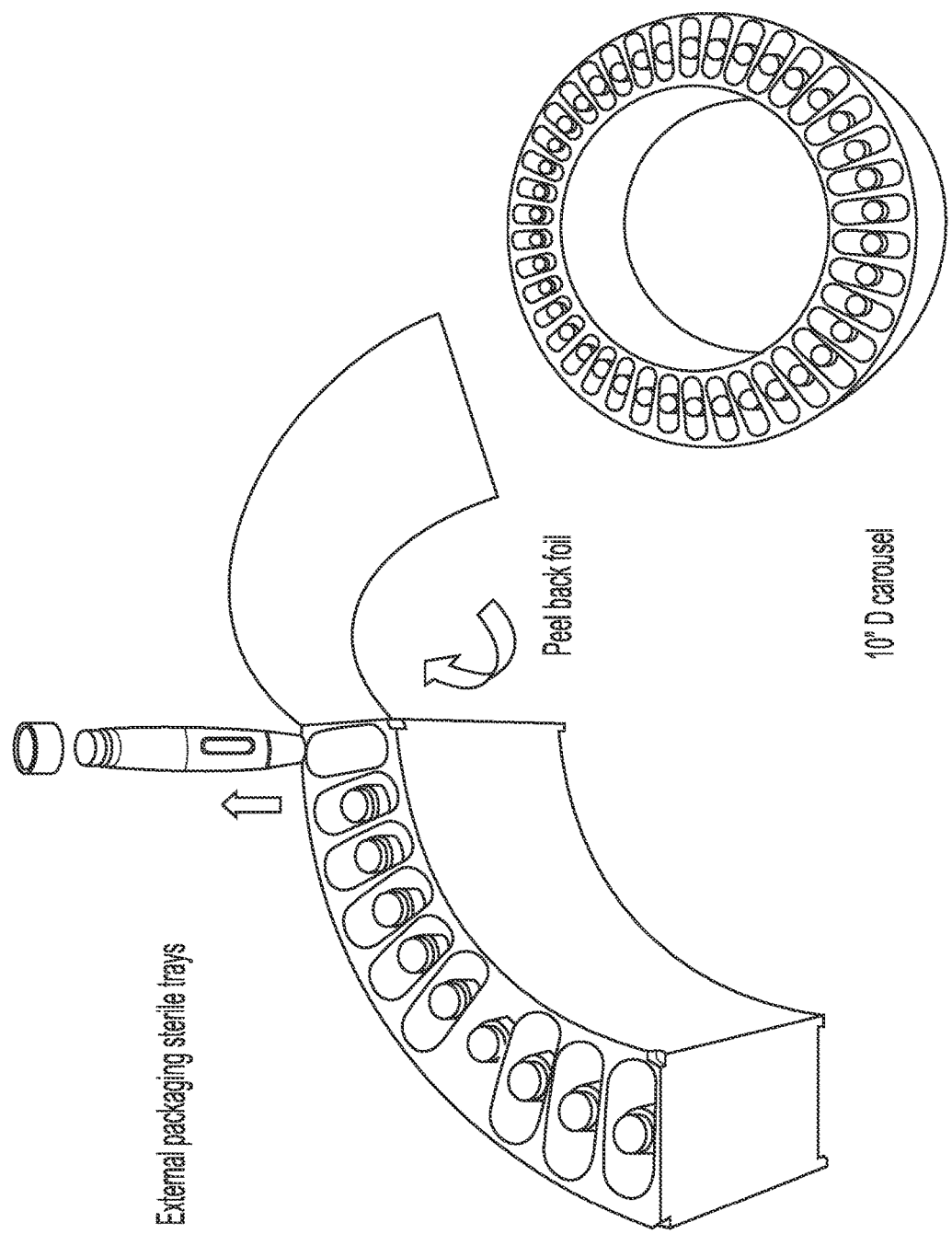
Fig. 14  External packaging of multiple devices with intergrated lancet and sterile alcohol pad. (Example 9)

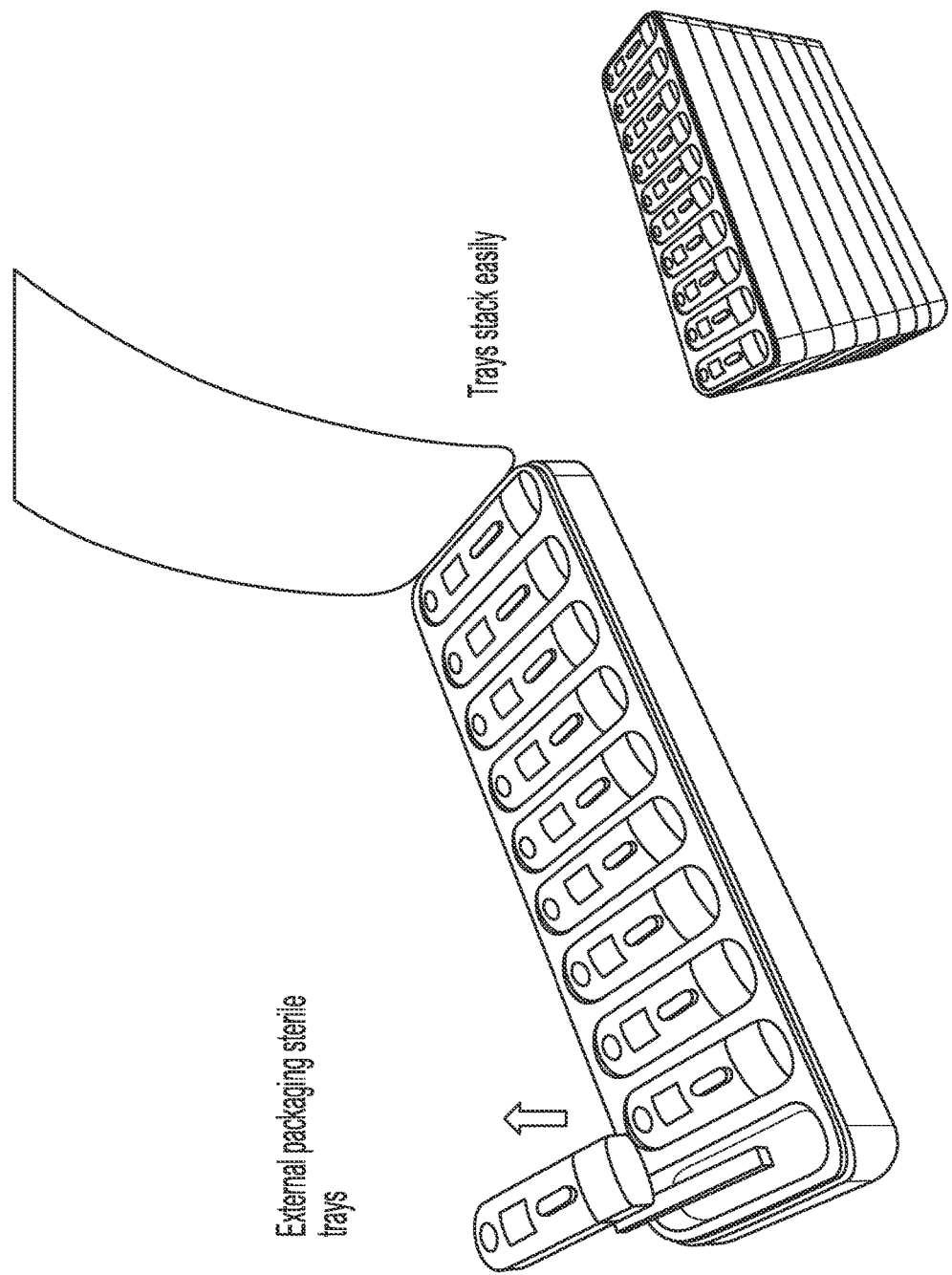
Fig. 15  External packaging of multiple devices with integrated lancet. (Example 9)

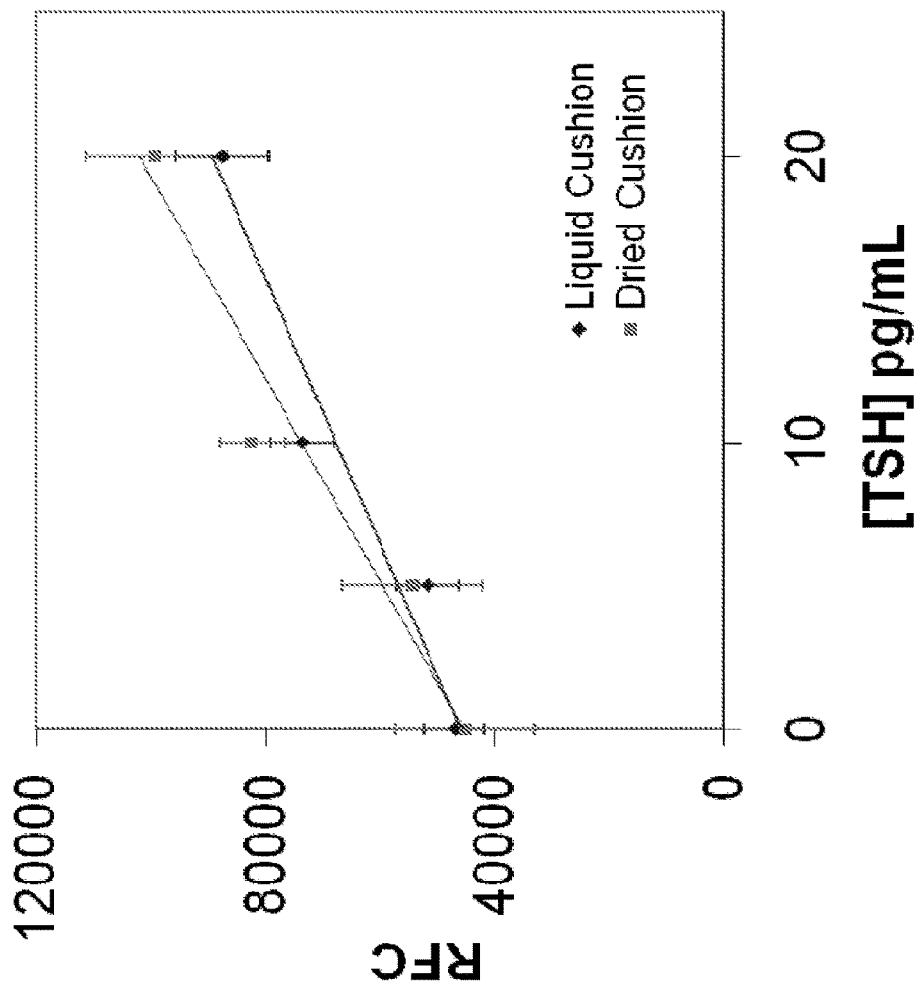
Fig. 16 Comparison of assay using air dried and liquid cushion reagents. (Example 2)

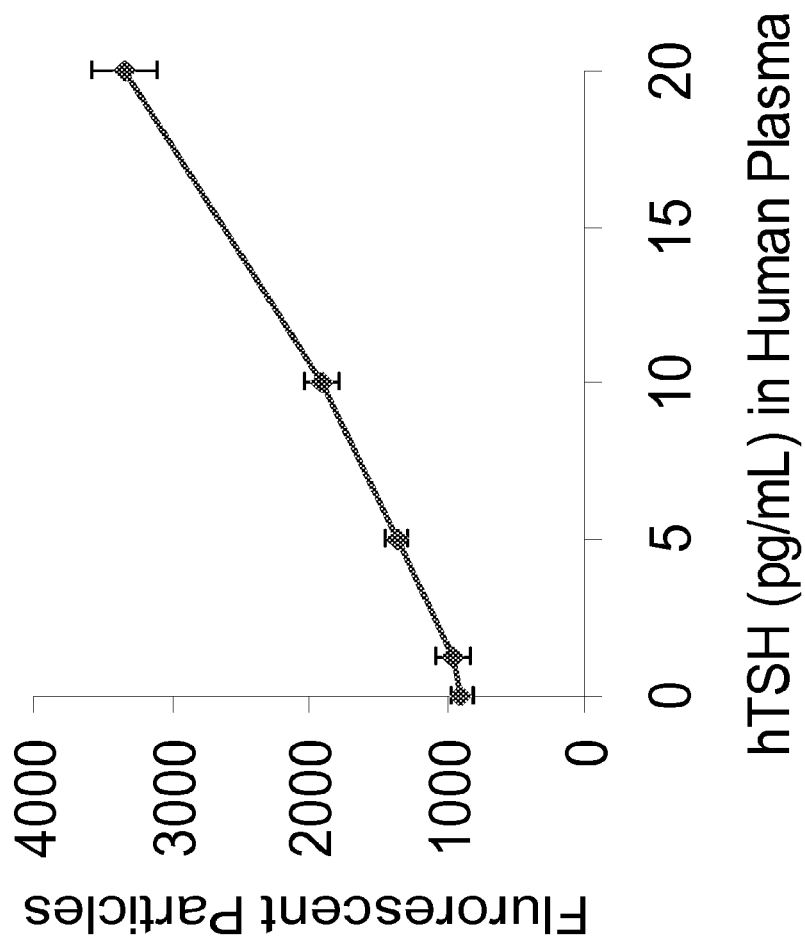
Fig. 17   Assay of Human Thyroid Stimulating Hormone (hTSH) in human plasma using liquid reagents. (Example 1)

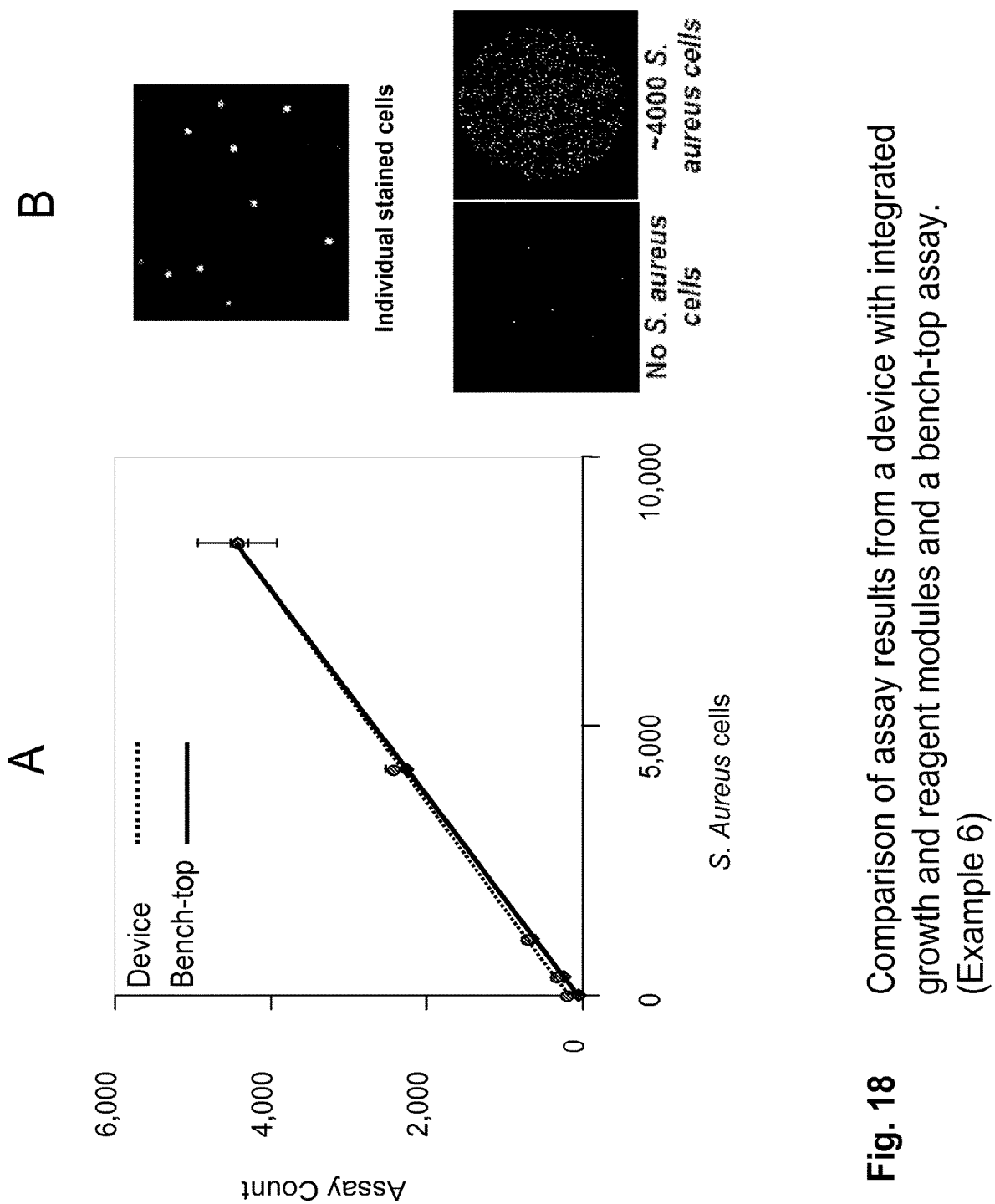
Fig. 18 Comparison of assay results from a device with integrated growth and reagent modules and a bench-top assay. (Example 6)

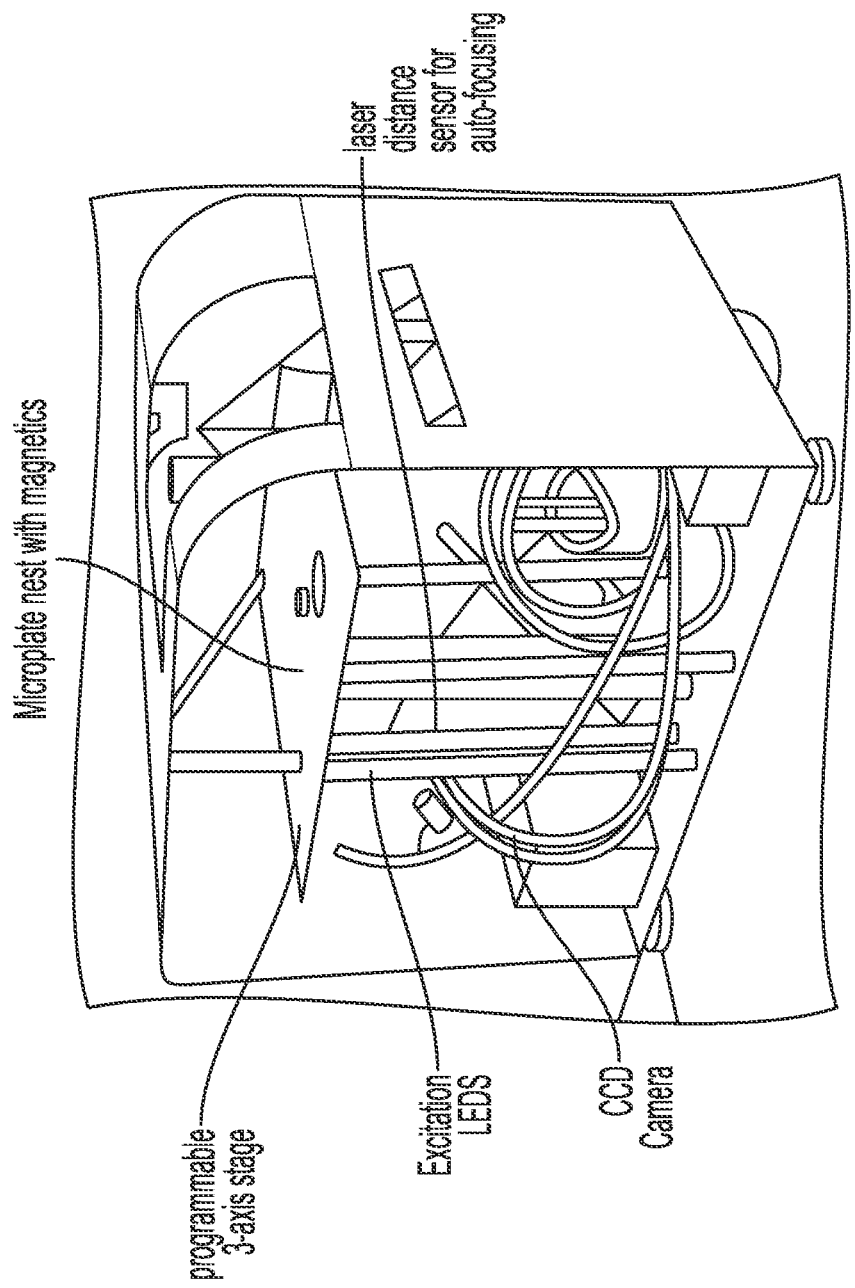
Fig. 19  High throughput automated analyzer (Example 1)

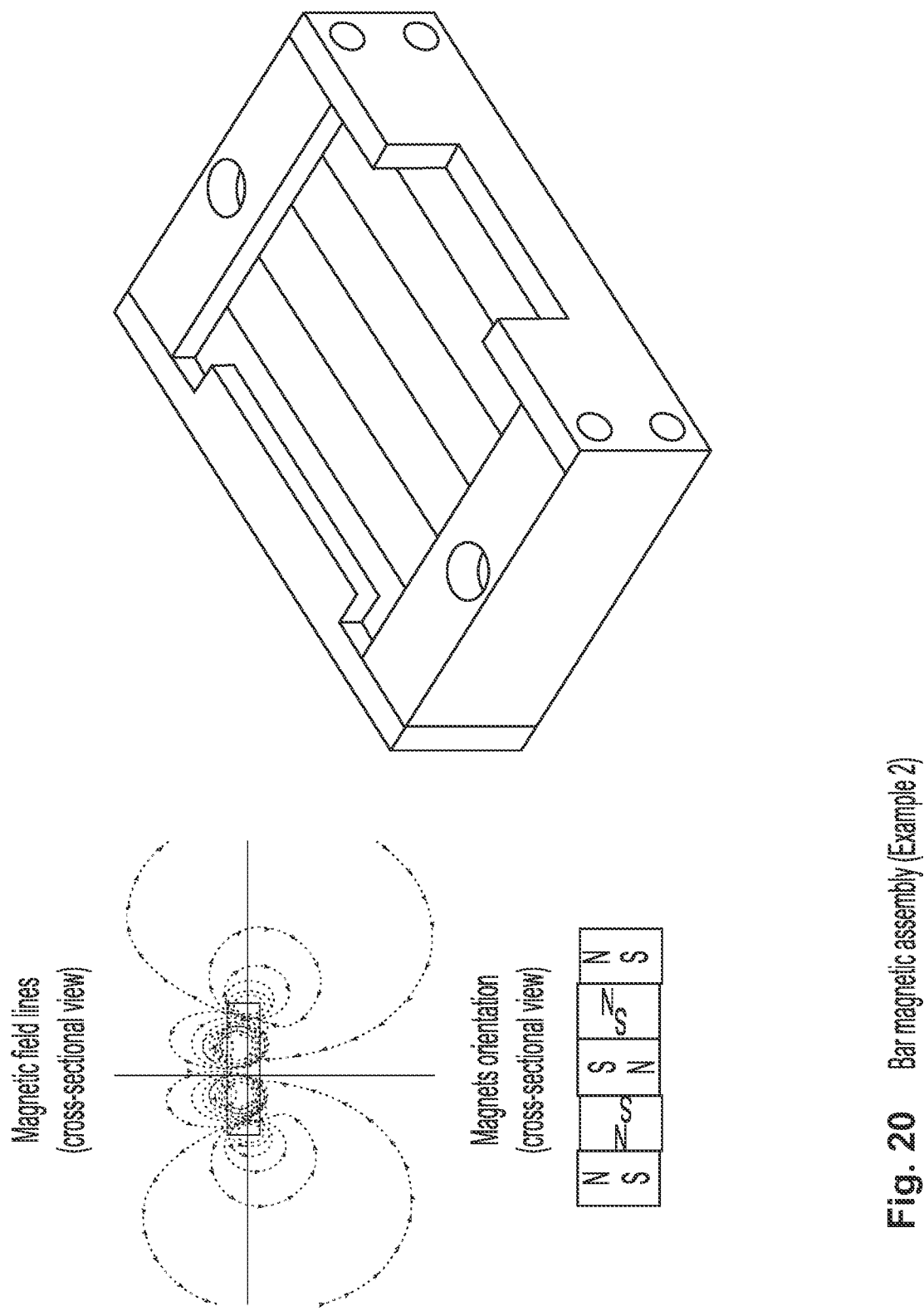
Fig. 20  Bar magnetic assembly (Example 2)

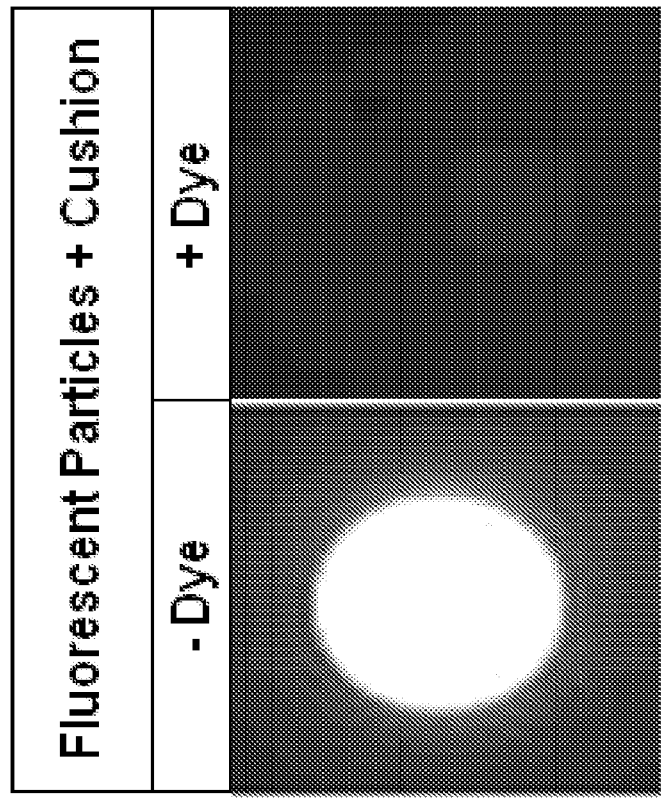
Fig. 21  Assay with and without dye cushion (Example 12)

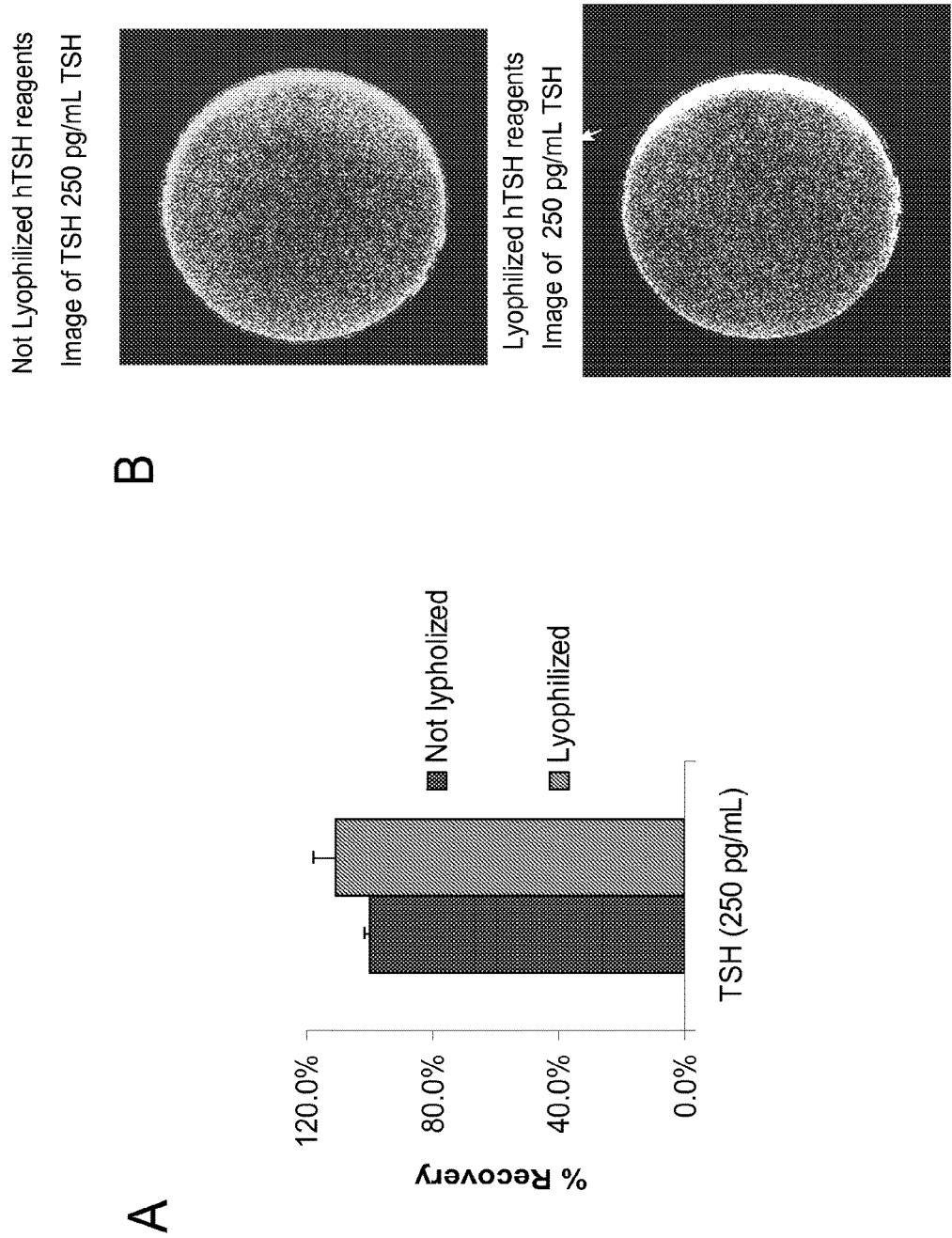
Fig. 22 Comparison of TSH assay performance between liquid and dried reagents (Example 2)

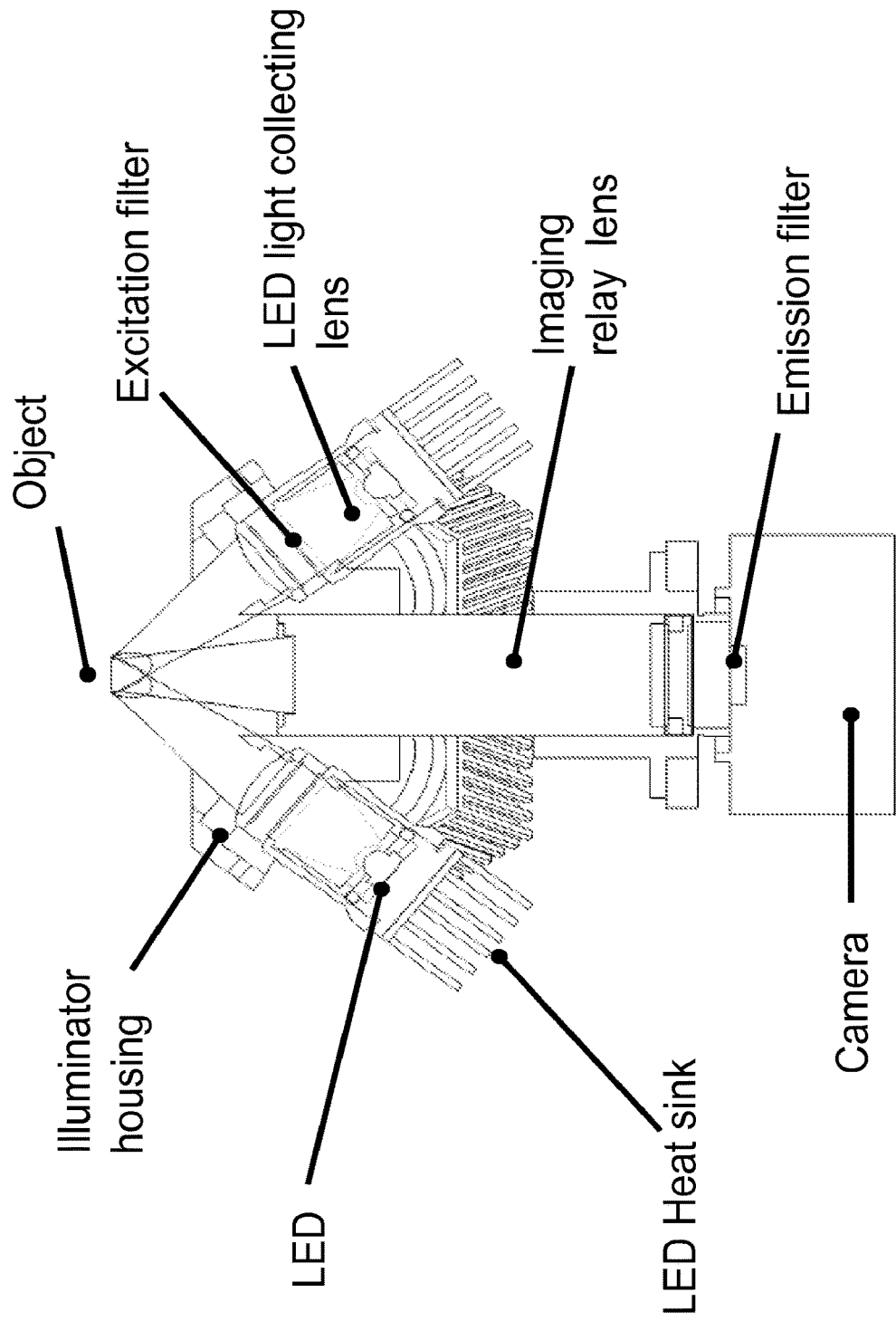
Fig. 23  Imaging and optics system diagram (Example 14)

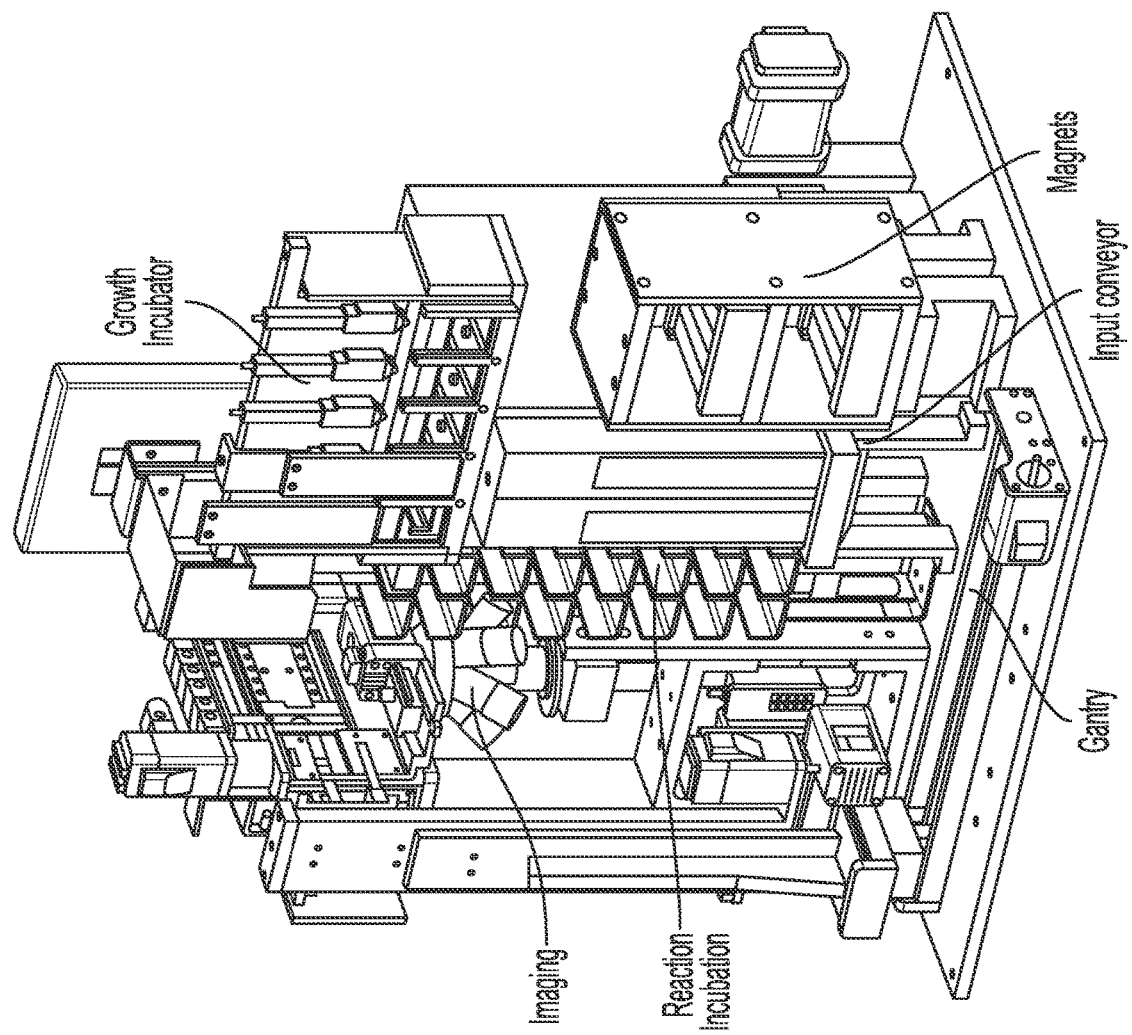
Fig. 24  Analyzer CAD Subassemblies (Example 14)

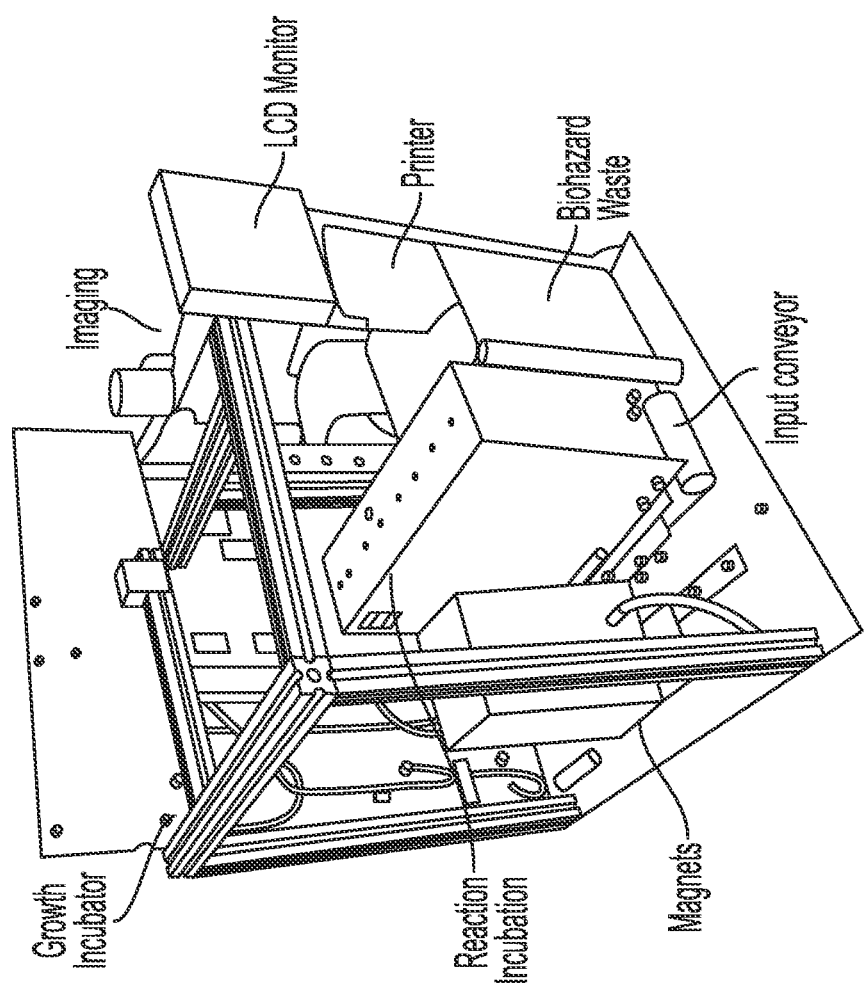
Fig. 25  Analyzer photograph (Example 14)

KITS AND DEVICES FOR DETECTING ANALYTES

CROSS-REFERENCE TO RELATED APPLICATIONS

This application is a continuation of U.S. patent application Ser. No. 13/120,504, filed Nov. 7, 2011, which application is a U.S. National Stage entry of International Patent Application Serial No. PCT/US09/58237, filed Sep. 24, 2009, which application claims benefit of U.S. Provisional Application No. 61/099,830, filed Sep. 24, 2008, all incorporated by reference.

GOVERNMENT SUPPORT

This invention was made with government support under grant numbers AI055195, AI080016, and AI078695 awarded by the National Institutes of Health. The government has certain rights in the invention.

BACKGROUND

Importance of Detecting Specific Targets.

Methods for detecting specific molecular, cellular, and viral targets are fundamental tools for medical and veterinary diagnostics, environmental testing, and industrial quality control. Examples of methods for detecting specific targets in clinical medicine include over-the-counter rapid pregnancy tests, microbiological culture tests for determining the resistance of infectious agents to specific antibiotics, and highly automated tests for cancer markers in blood samples. Detecting pathogen contaminants in food, high throughput screening of candidate compounds for drug discovery, and quantifying active ingredients in pharmaceuticals exemplify industrial manufacturing applications that depend on methods for determining the presence of specific targets. Environmental applications requiring testing for specific targets include detecting water supply contamination, airborne biothreat agents, and household fungal contaminants.

Labeling Targets.

One important approach for detecting specific cells, viruses, or molecules is to tag the targets with optically detectable labels. Targets can be specifically labeled or non-specifically labeled. Targets can be specifically labeled by tagging with target-specific binding molecules that contain an optical label. Target-specific labels can have various types of binding moieties including macromolecules (e.g., antibodies, protein receptors, nucleic acids, carbohydrates, and lectins) and small molecules (e.g., hormones, drugs of abuse, metabolites). The detectable signaling moieties of the target-specific labels can use a variety of signaling characters including fluorescence, phosphorescence, chromogenicity, chemiluminescence, light-scattering, and Raman scattering.

Alternatively, targets can be labeled non-specifically— that is, they can be labeled along with other entities in a sample. For example, all cells in the sample can be labeled with a DNA stain or all lipoproteins can be labeled with a label that binds to all such molecules. Non-specifically labeled targets can then be specifically detected using a target-specific selection as described below.

Specifically Selecting Targets.

Target-specific selection is usually important for detecting labeled targets. Specific selection is often used to physically isolate targets from other labeled entities and also from unbound label. For example, magnetic particles coated with target-specific antibodies can be used to complex with labeled targets. Applying magnetic force to the complexes can then deposit the labeled targets on a surface while labeled entities and unbound label are not deposited. Alternatively, specific selection can take place by capture, that is, by binding to a surface coated with target-specific binding moieties such as antibodies. Specific selection can occur either before or after target labeling.

Following specific selection and target labeling, the unbound label is generally removed from the reaction in successive washing steps while selection retains the specifically selected targets for subsequent detection. Washing steps require undesirable labor for the user in the case of manual test methods and may require sophisticated engineering for liquid handling in automated systems. Some technologies, such as lateral flow methods, use passive capillary action to wash unbound label and non-specifically bound label from labeled targets that have been specifically captured on a membrane or solid surface. Lateral flow methods simplify the washing function for manual tests, but these methods can be insensitive and are not appropriate for high throughput testing on automated platforms.

Using Imaging to Count Labeled Targets.

Imaging is a powerful method for detecting specifically selected labeled targets on a detection surface. Imaging methods map the optical signal emanating from each point in the detection area to a corresponding point in the image. In contrast, non-imaging detection methods generally integrate the optical signal emanating from the entire detection area.

Some imaging methods can detect and count individual labeled targets. Enumerating specifically labeled targets can result in detection at very low target levels compared to detection area integration methods. The sensitivity advantage of imaged-based target counting methods stems chiefly from the fact that the optical signal to background stays essentially constant as target levels decrease. In contrast, for detection area integration methods the signal to background decreases as the target levels decrease.

One type of method builds an image by systematically scanning the detection area with a microscopic beam. Scanning methods are more time consuming than methods that use digital array detectors (e.g., CCD or CMOS cameras) to enumerate specifically labeled targets in the entire detection area simultaneously.

Large Area Imaging at Low Magnification for Sensitive Target Counting.

Some methods use high magnification microscopy to enumerate the individual microscopic targets. Microscopic imaging lacks sensitivity because each image only samples a small area. Larger areas can be successively imaged, but acquisition of many images can be laborious, expensive and time consuming. Alternatively, labeled microscopic targets can be individually detected and enumerated using large area imaging at low magnification. Low magnification imaging can allow enumeration of a small number of microscopic targets in a relatively large area in a single image.

Methods that do not Require Washing to Remove Free Label from Specifically Labeled Targets.

Several methods that do not require washing have been developed that detect targets specifically complexed with labeled target-specific binding moieties. One type of method uses labels that do not emit signal unless they are bound to the target. These labels have the limitation that they do not emit a strong enough signal for efficient large area detection of individual labeled targets. Another method that does not require washes uses selection through a liquid phase barrier to separate labeled target complexes from unbound label. This approach uses detection area integration rather than sensitive image analysis and thus lacks high sensitivity.

Devices for Tests that Use Imaging to Detect Specific Targets.

A variety of devices have been developed for conducting tests for simultaneously detecting specific microscopic targets using imaging methods. Some testing devices are used for manual testing while others are designed for use in automated testing systems. Manual methods using visual detection of labeled targets include over-the-counter rapid lateral flow tests such as those used for pregnancy testing. Manual tests are generally designed for testing single samples and are not practical for high throughput testing. Visual tests do not count individual labeled targets and therefore lack sensitivity at low target levels.

Most testing devices for simultaneously detecting individual labeled microscopic targets use automated imaging at high magnification to image targets. For example, a simple microtiter well with an optically clear base may be used as a device that is imaged by microscopy. Targets are specifically labeled and deposited on the optical base surface. After removing the unbound label and non-specifically labeled entities by repeated washes the targets can be enumerated using a digital camera and microscope optics. Such devices have the drawbacks of requiring wash steps and lack the sensitivity because microscopic methods only image a small area.

Several testing devices that use large area automated digital imaging have been developed for simultaneously detecting individual labeled targets. These methods generally detect in a capillary chamber and use lateral flow to remove unbound label. As for other lateral flow methods, this technical approach complicates automation and limits the volume of sample that can be conveniently analyzed.

SUMMARY OF THE INVENTION

The invention provides improved kits and devices for analyzers that use large area imaging to detect individual microscopic targets. The invention allows large area imaging of individual labeled targets without wash steps, thus providing sensitive and specific detection while simplifying manual operation and lowering costs and complexity in automated operation. The invention can deliver rapid, accurate, and quantitative results. Herein we use the term imaging to mean simultaneous acquisition of an image from a region.

In one aspect, the invention features a kit including an imaging well having a depth of 2 mm and a detection area with a shortest linear dimension of ≤1 mm; signaling moieties, e.g., fluorescent particles or fluorescent or fluorogenic stains, stored in dry or liquid form; and selection moieties, e.g., magnetic particles, or capture molecules stored in dry or liquid form; wherein the signaling moieties and selection moieties or capture molecules specifically bind to a target, wherein the capture molecules are bound to the imaging well, wherein the detection area is transparent at wavelengths corresponding to the signal signature of the signaling moieties, and wherein the imaging well comprises features for alignment or registration of the imaging well with an imagining analyzer.

The kit may further include any one or more of a dye that interferes with the production or transmission of light to or from the signaling moieties; a sampling device, e.g., a swab, capable of collecting the target in a sample; a cushion or dried reagents that produce the cushion upon solvation, wherein the cushion has a density greater than an overlaying liquid layer following the solvation. The dried reagents that produce the cushion may be disposed in contact with the detection area and between the detection area and dried signaling and selection moieties. In certain embodiments, a detection surface defining the detection area is transparent in a region between 190-1100 nm, e.g., in the visible range. Preferably, the detection surface is non-fluorescent in the wavelengths of the signal signature. In other embodiments, the longest linear dimension of the detection area is 2 cm, and wherein the depth of the imaging well is less than 2 cm.

The invention also features a device for analyzing a sample potentially containing a target including a housing having an inlet for the sample; an imaging well having a depth of ≤2 mm and a detection area with a shortest linear dimension of ≤1 mm; a reservoir for selection moieties and/or signaling moieties, wherein the reservoir is disposed in the housing and fluidically connected to the imaging well (or selection moieties and/or signaling moieties disposed in the imaging well in liquid or dry form); and features for positioning or registration of the imagining well with an imaging analyzer, wherein the imaging well is disposed in the housing to allow for external illumination of the detection area and/or detection of light emitted from the imaging well, wherein the inlet is fluidically connected to the imaging well, and wherein the detection area is transparent at wavelengths corresponding to the signal signature of the signaling moieties. The device may further include one or more of capture molecules that are bound to the imaging well and that specifically bind the target; a seal for the inlet, which is engaged after the sample is introduced into the inlet; a meter for the volume of the sample introduced into the device via the inlet; a second reservoir disposed in the housing and containing a cushion or dried reagents that produce the cushion upon solvation, wherein the cushion has a density greater than an overlying liquid layer following the solvation and wherein the second reservoir is fluidically connected to the imaging well; a third reservoir disposed in the housing and containing a dye that interferes with the production or transmission of light to or from the signaling moieties, wherein the third reservoir is fluidically connected to the imaging well; a sample processing well disposed in the housing and fluidically connected to the inlet, the imaging well, and the reservoir; a plurality of imaging wells of (a) and a channel in the housing that divides sample introduced into the inlet among the plurality of imagining wells; a channel in the housing connecting the inlet to the imaging well; a vent in the housing that allows gases to exit the device as a result of the flow of liquids in the device; a sampling device, e.g., a lancet, which may or may be fluidically connected to the inlet; a filter that separates the inlet from the imaging well and allows the target to pass selectively; and an interface in the housing for connection with a fluid pump, which pumps fluids from the inlet towards the imaging well.

In various embodiments, the detection area is non-fluorescent at the wavelengths corresponding to the signal signature. The imaging well may be integral with or separable from the housing. The inlet may accept a sampling device, e.g., a sample swab or pipette. The housing may further include stabilizers for vertical stacking of multiple devices. When present, engaging a seal may result in movement of the sample from the inlet towards the imagining well. For example, the seal may include a plunger or be capable of being variably moved relative to the inlet, e.g., by screwing. The imaging well may further include a cushion or dried reagents that produce the cushion upon solvation, wherein the cushion has a density greater than an overlying liquid layer comprising solvated target signaling moieties and selection moieties following the solvation and/or a dye that interferes with the production or transmission of light to or from the signaling moieties. The second and third reservoirs, described above, may or may not be the same reservoir. A sample processing well may contain reagents that promote or inhibit cellular replication, e.g., growth media. A sample processing well may be separated by a valve from the imaging well. Sample may move from the inlet to the imaging well by capillary action. Any reservoir in the device may be separated from the imaging well by a frangible seal. The volume of the sample is, for example, between 1 µL and 1 mL, and the volume of the imaging well is, for example between 10 µL and 1 mL.

Exemplary imaging wells for use in the kits and devices of the invention are also shown in the figures and described in the examples.

In certain embodiments, the kits and devices include no provision for washing a sample prior to detection. The kits and devices may also employ labeling particles as the signaling moiety. Contacting of the labeling particles with a target results in the formation of target:labeling particle complexes. Labeling particles may be present in a kit or device in an amount to result in a specified labeling ratio, e.g., less than 100.

Some or all of the reagents for the tests may be contained in the testing device. Some or all of the reagents can be added by a user manually or by an automated instrument. Testing devices may be simple containers. Alternatively, they can be complex cartridges including, for example, combinations of: onboard pumps, fluidics channels, valves, reagent reservoirs, electronics, detectors, sample input modules, and waste modules.

By washing is meant a process for physically removing, from a container or a surface, liquid containing undesirable components from targets, which, in contrast to the undesired components, are either retained, selected, or captured in the container or on the surface.

By a test not requiring washing is meant a test in which targets are detected without using wash steps.

By an analyzer or imaging analyzer is meant an apparatus having an array photodetector and imaging optics allowing simultaneous imaging of a detection area, as defined herein. Analyzers can have many other functions for enhancing detection including modules for applying selective forces on selection moieties, conveyance, or incubation.

By a well is meant a vessel that can hold liquid. Wells generally have a well depth 1 mm.

By an imaging well is meant a well through which labeled targets can be detected by imaging. Imaging wells have a detection surface on which an imaging analyzer can detect labeled target particles. The material lying between the detection surface and the imaging analyzer's photodetector has optical properties for supporting imaging detection of labeled targets. For example, the material is generally transparent and has low optical background in the spectral region corresponding to the signal signature of the device's signaling moieties.

By imaging well depth is meant the distance of the imaging well along an axis that is perpendicular to the detection surface.

By cushion, density cushion, liquid cushion, cushion layer, or liquid density cushion is meant a substantially liquid layer which is denser than the overlying layer. In the invention, the cushion is found in the imaging well lying between the detection surface and the liquid layer including the sample and test reagents. This cushion provides a physical separation between the test's reagents and the detection surface. Using selection, labeled targets complexed with selection moieties are moved through the cushion and deposited on the detection surface for imaging. Signaling moieties which are not complexed with a selection moiety are excluded from the detection zone by the dense liquid layer of the cushion.

By dye is meant a substance or mixture added to the reaction which interferes with the production or transmission of light to or from signaling moieties. The dye reduces or eliminates signal originating outside of the detection zone while allowing detection of the signal derived from signaling moieties within the detection zone. For devices that include fluorescent signaling moieties, dyes can absorb light of the fluorescent excitation frequencies, the fluorescent emission frequencies, or both. Various dye properties can be useful for this purpose including light scattering and absorbance. In various embodiments, the dye reduces signal by at least 50%, 75%, 85%, 90%, 95%, or even 99%.

By dyed cushion is meant a cushion that includes dye. The dyed cushion simultaneously provides a physical exclusion of the bulk reaction from the detection zone (as a function of the density of the dyed cushion) while preventing or reducing the transmission of signal from the overlying reaction to the detector (as a function of the dye included in the dense layer).

By sampling device is meant a device used to collect a sample. Examples of sampling devices include swabs, capillary tubes, wipes, beakers, porous filters, bibulous filters, and pipette tips.

By target is meant a cell, virus, molecule, or molecular complex that is potentially present in a sample and the presence of which is tested by the invention.

By category of target is meant one or more features shared by multiple targets so that the multiple targets are considered identical for the purposes of a test constructed using the invention. For example, for a test designed to detect all HIV viruses, the category is HIV. Such a test would detect all HIV viruses, without differentiating the HIV-1 and HIV-2 variants. In this case, the category of the target includes both HIV-1 and HIV-2. The goal of another test might be to distinguish HIV-1 from HIV-2. In this case, each type of HIV would be considered a different category. If the goal of the test is to detect *C. albicans*, three probes considered identical for the purpose of the test because they share the common feature that they bind specifically to *C. albicans* would be considered to be in the same category of target molecules.

By category-binding molecule is meant a molecule or molecular complex that specifically binds to a category-specific binding site. Examples of category-binding molecules are nucleic acid probes that hybridize to genomic DNA; nucleic acid aptamers that have been selected or "evolved" in vitro to bind specifically to sites on proteins; antibodies that bind to cellular antigens or serum proteins; and ligands such as epidermal growth factor or biotin that bind specifically to hormone receptors or to binding molecules, such as avidin. Two category-binding molecules are distinct if they bind to distinct and non-overlapping category-specific binding sites. Category-binding molecules may be referred to according to their molecular composition, e.g., a category binding oligonucleotide, probe, antibody, ligand, etc.

By capture molecule is meant a category-binding molecule that is stably bound to a surface, membrane, or other matrix that is not a particle.

By a category-binding molecule that specifically binds to a category of target is meant a category-binding molecule that binds under defined binding conditions to essentially all targets that are members of a category scanned for by a test, but to essentially no other molecules that are likely to be present in the sample. The number of category-binding molecules that are bound by targets in a category scanned for as compared to the number bound by targets not in such a category, are typically two-fold, five-fold, ten-fold, or greater than fifty-fold greater.

By signal element is meant a molecule or particle that directly generates a detectable signal. The phrase "directly generates" refers to the fact that signal elements are the immediate source or critical modulator of the detectable signal. Thus, if the signal is photons that arise from a fluorophore, the fluorophore is the immediate source of the photons and, therefore, is a signal element. If the signal is photons scattered by an RLS particle, the RLS particle is a signal element. Alternatively, if the signal is the light transmitted or scattered from a chromogenic precipitated product of the enzyme horseradish peroxidase, the chromogenic product is the signal element.

A characteristic of a signal element is that such an element cannot be divided into parts such that each part generates a signal that is comparable (in character, not necessarily in intensity) to the whole. Thus, a 2 nM diameter quantum dot is a signal element, as dividing it changes the character (emission spectrum) of the resulting nanocrystals. A 5 µm particle impregnated with a fluorescent dye such as fluorescein, is not a signaling element, since it could be divided into parts such that each part has signaling characteristics comparable to the intact particle. The molecule fluorescein, in contrast, is a signaling element. The detectable products of signal generating enzymes (e.g., luciferase, alkaline phosphatase, horseradish peroxidase) are also considered signal elements. Such signal elements (or their precursors when there is a chemical conversion of a precursor to a signal element) may be diffusible substances, insoluble products, and/or unstable intermediates. For example, the enzyme alkaline phosphatase converts the chemiluminescent substrate CDP-Star (NEN; catalog number NEL-601) to an activated product, which is a photon-emitting signal element.

By signaling moiety is meant a molecule, particle, or substance including or producing (in the case of enzymes) one or more signal elements and that is or can be conjugated to a category-binding molecule. The signaling moiety can be attached to the category-binding molecule either covalently or non-covalently and either directly or indirectly (e.g., via one or more adaptor or "chemical linker" moieties or by both moieties being conjugated to the same particle). Examples of signaling moieties include carboxylated quantum dots; a fluorophore such as Texas Red that is modified for binding to a nucleic acid probe or an antibody probe; streptavidin-coated fluorescent polystyrene particles (which can be conjugated to biotinylated category-specific binding proteins); a rolling-circle replication product containing repeated nucleic acid sequences each of which can hybridize to several oligonucleotides tailed with fluorescently modified nucleotides and which contains a category-specific binding oligonucleotide at the 5' end. A signaling moiety can include physically distinct elements. For example, in some cases the signaling moiety is an enzyme (e.g., alkaline phosphatase) that is conjugated to a category-binding molecule (an antibody, for example). Signal is generated when a substrate of alkaline phosphatase (e.g., CDP-Star, or BM purple from NEN and Roche, respectively) is converted to products that are signal elements (e.g., an unstable intermediate that emits a photon, or a precipitable chromogenic product). It is not unusual for the category-binding molecules, enzymatic signaling moieties, and substrate to be applied to the reaction at distinct times.

By particle is meant a matrix which is less than 50 microns in size. The size of a population or batch of particles is defined as the mean measurement of the longest pair of orthogonal dimensions for a sample of the particles. The longest pair of orthogonal dimensions is the pair of orthogonal dimensions of a particle, the sum of the lengths of which is the maximum for all such sums for the particle. If a sample of two particles has a longest pair of orthogonal dimensions of 1 micron×2 micron and 2 micron×3 micron, respectively, the mean measurement of the longest pair of orthogonal dimensions is 2 microns [(1+2+2+3)/4=2 microns]. The mean measurement of the longest pair of orthogonal dimensions for a sample of particles is, e.g., less than 50 microns, less than 20 microns, or less than 5 microns.

Many particles have some characteristics of a solid. However, molecular scaffolds or complexes, which may not be rigid, are also defined as particles. For example, dendrimers or other branching molecular structures are considered to be particles. Similarly, liposomes are another type of particle. Particles can be associated with or conjugated to signal elements. Particles are often referred to with terms that reflect their dimensions or geometries. For example, the terms nanosphere, nanoparticle, or nanobead are used to refer to particles that measures less than 1 micron along any given axis. Similarly, the terms microsphere, microparticle, or microbead are used to refer to particles that measure less than one millimeter along any given axis. Examples of particles include latex particles, polyacrylamide particles, magnetite microparticles, ferrofluids (magnetic nanoparticles), quantum dots, etc.

By labeling particle is meant a particle that can specifically bind to targets and generate a signal. Labeling particles are conjugated to both signaling moieties and to category-binding molecules.

By target:labeling particle complex is meant a labeling particle to which one or more targets are specifically bound.

By labeling ratio is meant the ratio of targets to labeling particles during a contacting step. For example, if $1\times10^7$ labeling particles are contacted with a sample containing $1\times10^6$ targets, the labeling ratio is 0.1. For the purposes of calculating labeling ratios, only the targets that can specifically bind to labeling particles are considered. For example, targets that are physically inaccessible (e.g., sequestered in a cellular compartment) are not included in the calculation.

By signal character of a signal element or signal moiety is meant the aspect or aspects of a signal generated by the signal element or signaling moiety that is useful for distinguishing it from other signal elements or signaling moieties. For example, the signal character of a signaling moiety labeled with fluorescein and rhodamine is fluorescence. The character of a radio transponder is radio frequency. Examples of photonic signaling character are fluorescence, light scattering, phosphorescence, reflectance, absorbance, chemiluminescence, and bioluminescence. All but the latter two examples of photonic signaling character depend on external illumination (e.g., a white light source, a laser light source, or daylight). In contrast, chemiluminescence and bioluminescence are signaling characters that are independent of external light sources.

By signal signature is meant the distinctive signaling quality of the combination of signaling moieties that bind to a category of targets in a test. A target that is bound to four types of antibodies, one of which is conjugated to a fluorescein molecule, and three of which are conjugated with rhodamine molecules has a signal signature that is described by the combined weighted absorbance and emission spectra of fluorescein and rhodamine.

By selection force is meant a force that is used to capture, isolate, move, or sequester targets. Examples of selection forces include gravity, magnetism, electrical potential, centrifugal force, centripetal force, buoyant density, and pressure. Targets can be mobilized by a selection force acting on the targets alone. Alternatively, selection forces can act specifically on targets that are associated with selection moieties (see definition below).

Examples of the application of selection forces to mobilize targets include centrifugation of targets; magnetic selection of targets bound to magnetic particles; gravitational sedimentation of targets labeled with metallic particles; and deposition of targets on a porous membrane by vacuum filtration. Further instances of the use of selection forces are included in the examples below.

By selection moiety is meant an atom, molecule, particle, or other entity that can be conjugated to a category-binding molecule and that confers on the category-binding molecule the ability to be selectively captured, isolated, moved, or sequestered by a selection force. When a category-binding molecule:selection moiety complex is specifically bound to a target, the target can also generally be selectively captured, isolated, moved, or sequestered by the selection force. Selective refers to the preferential conferring of susceptibility to mobilization by the selection force on selection moieties and associated entities over entities not associated with selection moieties.

Paramagnetic particles and ferritin are examples of selection moieties. A dense silica particle that sinks in solution is another type of selection moiety. Such particles, when coated with category-binding molecules and bound to a microbial target will cause the target to sink in aqueous solution, thus resulting in separation of the bound target from other sample unbound constituents.

By a roughly planar surface or substrate is meant a surface that can be aligned in parallel to an imaginary plane such that when the distance is measured from points in any 1 mm×1 mm square on the surface to the closest points on the imaginary plane, the absolute value of the mean distance is less than 50 micrometers.

By detection surface is meant the surface of a roughly planar substrate onto which targets are deposited in some embodiments of the invention. In embodiments using photonic signaling character, if the detection surface is optically transparent, detection can be effected via either face of the detection surface. If the detection surface is opaque, detection is effected via the face of the detection surface on which the targets are deposited.

By detection area is meant the area of the detection surface or detection zone that is simultaneously analyzed by the invention. The detection area is typically greater than 1 mm, e.g., greater than 5 mm, 10 mm, or 15 mm, in its longest linear dimension. For example, the section of a glass slide that is simultaneously imaged by an optical device that includes a collection lens and a CCD chip might measure 0.8 cm×0.5 cm. The detection area is then 0.4 cm².

By detection zone is meant the volume in which targets can be detected. The detection zone has the same dimensions as the detection area but has a depth corresponding to the depth in which a labeling particle can be detected and identified. The depth of the detection zone is therefore dependent on the threshold criteria used to score for positive signal. When optical detection is used, the depth of the detection zone is dependent on the optical depth of field.

By the longest dimension of the detection area is meant the line of maximum length that can be drawn between two points on the perimeter of the detection area. For example, if the detection area is a rectangle measuring 0.3 cm×0.4 cm, the longest dimension of the detection area is the diagonal, 0.5 cm. If the detection area is an ellipse with semi-major axis of length 7 mm and semi-minor axis of length 2.5 mm, the longest dimension of the detection area is 14 mm.

By the shortest dimension of the detection area is meant the line of minimum length that can be drawn between two points on the perimeter of the detection area. For example, if the detection area is a rectangle measuring 0.3 cm×0.4 cm, the shortest dimension of the detection area is 0.3 cm. If the detection area is an ellipse with semi-major axis of length 7 mm and semi-minor axis of length 2.5 mm, the shortest dimension of the detection area is 5 mm.

By large area detection or large area imaging is meant a method for detecting microscopic targets in which the detection area (the area that is simultaneously analyzed by the detection device) is much larger than the target. The detection area for large area detection has linear dimensions 1 mm. In contrast, the microscopic targets are substantially smaller, typically measuring less than 50 μm in at least two orthogonal dimensions. Examples of large area detection include imaging a 9 mm diameter detection area with a CCD camera; imaging a 2 cm×1 cm rectangle by scanning with a CCD line scanner that has a long dimension of 1 cm; imaging a 4 cm×4 cm filter containing microbial targets using direct exposure on photographic film; and visual detection of colored spots corresponding to microscopic targets on a 1 cm×3 cm test area in a rapid lateral flow strip test.

By conjugated or stably associated is meant a physical association between two entities in which the mean half-life of association is least one day in PBS at 4° C.

By simultaneously detecting targets in a section of the detection area is meant detection of the signal from a section of a roughly planar detection surface in one step. Large area imaging of targets in a detection area using a CCD chip, visual detection, or photodiode-based signal integration are examples of simultaneous detection.

By sample is meant material that is scanned by the invention for the presence of targets. By direct visual detection is meant visual detection without the aid of instrumentation other than wearable corrective lenses. For example, direct visual detection can be used to detect the reddish reflective signal of nanogold particles in some rapid lateral flow tests.

By photoelectric detector is meant a man-made device or instrument that transduces photonic signals into electric signals. Examples of photoelectric detectors include CCD detectors, photomultiplier tube detectors, and photodiode detectors, e.g., avalanche photodiodes.

By illuminating is meant irradiating with electromagnetic radiation. Electromagnetic radiation of various wavelengths can be used to illuminate. It includes, for example, radiation with wavelengths in the X-ray, UV, visible, or infrared regions of the spectrum. Note that illuminating radiation is not necessarily in the visible range. Illuminating preferably occurs with the range of 190 to 1100 nm.

By signal elements or signaling moieties with photonic signaling character is meant signal elements or signaling moieties that are detectable through the emission, reflection, scattering, refraction, absorption, capture, or redirection of photons, or any other modulation or combination of photon behavior. Some examples of signal elements or signaling moieties that have photonic signaling character include: the fluorophore Texas Red (fluorescent signaling character); CDP-Star (chemiluminescent signaling character); luciferase (bioluminescent signaling character); resonance light scattering particles (light scattering signaling character); BM purple (light absorption or chromogenic signaling character); and up-converting phosphors (absorption of two long wavelength photons and emission of one shorter wavelength photon).

PBS is a phosphate-buffered saline solution containing: 120 mM NaCl, 2.7 mM KCl and 10 mM phosphate buffer (sodium salt) pH 7.4.

CCD is charged coupled device.

hTSH is human thyroid stimulating hormone.

PSA is pressure sensitive adhesive.

RF ID is radio frequency identification.

Unless otherwise noted, microbiological strains described in the specifications are obtained from the American Type Culture Collection (ATCC), Manassas, Va.

BRIEF DESCRIPTION OF THE DRAWINGS

FIG. 1 Modular assembly of a device where sample is metered by actuation of a plunger integrated into the cap. (Example 6)

FIG. 2 Example of a deformable pouch with a frangible seal acted upon by a roller mechanism.

FIG. 3 Comparison of assay performance between liquid and dried reagents (Example 1). Lyophilized S. Aureus reagents demonstrating the performance between liquid and dried reagents. FIG. 3A shows data comparing fluorescent objects (Multipath count) for samples with and without S. Aureus cells analyzed per the assay. FIG. 3B shows actual images from samples with and without S. Aureus cells using the assay using lyophilized S. Aureus reagents.

FIG. 4 A simple device that consists of a single vessel with dried reagents, a cap, and an imaging module. (Example 3)

FIG. 5 A device that autonomously processes a single sample comprising an integrated sample collection function. (A) Integrated device concept (B) SLA device (C) design of autonomous device (D) Polyjet examples of autonomous devices (E) mm-sized lyophilized spheres containing immunoassay reagents, (F) image of a positive immunoassay reaction using dried reagents and dried cushion material. (Examples 8, 9)

FIG. 6 Device with integrated sample collection modules (lancet and sterile alcohol pad in cap). (Example 9)

FIG. 7 A device with multiple reaction vessels where sample is metered by actuation of a screw cap. (Example 4)

FIG. 8 A fully integrated device with multiple wells and alignment features for stacking and registration in an analyzer. (Example 5)

FIG. 9 A device with intermediate processing growth modules. (Example 6)

FIG. 10 Photograph of a stackable device with intermediate processing growth modules. (Example 6)

FIG. 11 Work flow of a fully integrated device that accepts direct insertion of sample swabs MRSA testing.

After opening the package (1), the user applies a barcode (2), obtains a sample (3), inserts the swab into the device (4). Cap closure breaks off the swab ends (5) and one or more devices are placed in an analyzer (6). All other steps, including hospital specific data reporting, occur automatically. (Example 7)

FIG. 12 Internal view of modules that comprise a fully integrated device that accepts direct insertion of sample swabs. (Example 7)

FIG. 13 Multiple self-contained vessels with integrated disposable pipette tips. (Examples 10, 11)

FIG. 14 External packaging of multiple devices with integrated lancet and sterile alcohol pad. (Example 9)

FIG. 15 External packaging of multiple devices with integrated lancet. (Example 9)

FIG. 16 Comparison of assay using air dried and liquid cushion reagents. (Example 1)

FIG. 17 Assay of Human Thyroid Stimulating Hormone (hTSH) in human plasma using liquid reagents. (Example 2)

FIG. 18 Comparison of assay results from a device with integrated growth and reagent modules and a bench-top assay. (Example 6)

FIG. 18A shows a standard curve of assay results from a device with integrated growth compared to and a bench-top assay. FIG. 18B shows a digital image of individual stained S. aureus cells without magnification and a comparison to a sample without cells.

FIG. 19 High throughput automated analyzer (Example 1) FIG. 20 Bar magnetic assembly (Example 2) FIG. 21 Assay with and without dye cushion (Example 1). Demonstrating the use of dyed cushion for removing background from free fluorescent labeling particles specific for hTSH.

FIG. 22 Comparing performance of liquid and dried reagents in a TSH assay (Example 2) FIG. 22A shows data comparing fluorescent objects (Multipath count) for samples with and without lyophilized hTSH analyzed per the assay described below. FIG. 22B shows actual images from samples with 0 pg/mL and 250 pg/mL TSH using lyophilized TSH reagents.

FIG. 23 Diagram of imaging components of an imaging analyzer.

FIG. 24 Diagram of components of an imaging analyzer.

FIG. 25 Photograph of an imaging analyzer.

DETAILED DESCRIPTION OF THE INVENTION

Overview of invention. The invention features kits and devices for rapid and sensitive detection of targets in medical, industrial, and environmental samples. In various embodiments, the device has on-board reagents (signaling moieties and selection moieties) for distinguishing labeled targets from free label and other labeled entities without wash steps; one or more imaging wells allowing detection of individual labeled targets using large area imaging; accepts a variety of sample types; can be introduced into manual or automated imaging analyzers; allows for labeling of targets; can include sample and/or reagent processing functions; can include fluidics functions for movement of liquids; and can interface with mechanical devices on an automated analyzer to move fluids. Diagnostic tests based on the device can be rapid, ultra sensitive, quantitative, easy-to-use, multiplexed, and automated. The kits or devices may be designed for use with an imaging analyzer as described herein. The devices and kits may be employed in assays as described herein.

Some of the key functions and attributes of the device are described in the following sections:

1. Device structure
2. Sample input module
3. Dynamic interaction with analyzer

4. Detection without washing
5. Liquid reagents
6. Dried reagents
7. Fluidic system
8. Intermediate processing
8. Analyte selection
10. Imaging
11. Information management
12. Packaging

1. Device Structure

The overall structural complexity and organization of the device depends on the application, venue, and analyzer and can range from a simple optical container having reagents to a multifunctional device with built-in fluidic processing elements and interface with mechanical elements of an analyzer. FIG. 4 illustrates a simple embodiment of the invention, a single vessel with an optically clear imaging well for large area imaging, dried reagents, and a cap. A more complex embodiment, shown in FIG. 12, has multiple modules that are integrated to achieve multiple functions. The device shown in FIG. 12 has the functionality of the simpler device shown in FIG. 4 but also has a module for accepting sample swabs, a closure mechanism that initiates flow of on-board liquid reagents that bathe the swabs, media, and dried reagents for determination of antibiotic resistance by differential growth of bacterial cells in growth wells, and a features for interacting with analyzer mechanics.

The device and its modules are amenable to various manufacturing methods and strategies. The device can be manufactured as an integrated unit or separate modules using a variety of materials, manufacturing processes, and assembly methods. The device can perform one or more assays per sample, can accommodate one or more samples, and can incorporate fluidics and modules for intermediate sample processing.

Types of Modules.

A variety of structural modules may be integrated into the device. Modules may contain liquid or dried reagents in wells, channels, or blister pouches. The device may have a sample input module for sample input including wells, capillary channels, or receptacles for sampling devices. There may be one or more imaging wells with optical properties for efficient imaging. One or more modules may be used for assay reactions or sample processing. These and other functional modules are described in detail the following sections.

Combinations of modules can be formed from a single manufactured part, or they can be fabricated as separate structural modules that are integrated during manufacturing assembly. Each module can be independently fabricated or not. For example, reaction modules can be an individual unit such as in FIG. 4, or they can be combined in parallel as in FIG. 7. Modules of different functions can be combined into a single manufactured module, such as in FIG. 1 where multiple growth and imaging well modules have been fabricated in a single injection molded piece. Components can also be discrete parts that are assembled or joined together after fabrication, such as the separate cap and plunger modules in FIG. 1 that are joined by a pressed fit during device assembly. Modules can be joined together readily as discrete subunits forming an integrated assembly. The numbers and types of modules integrated may vary depending on the type of assay tested for on a device. For example, a device that requires a blood sample may have an integrated lancet (FIG. 6). Alternatively, a device for testing nasal samples may have a receptacle for nasal swabs (FIG. 12). A device that processes an assay requiring growth may have wells for on-board for growth (FIG. 9).

There may or may not be a base module into which other modules are assembled. For example, FIG. 1 shows a device where modules mount to a base by pressure sensitive adhesive tape. However in FIG. 4, the device modules are all manufactured as a single integrated part, and a base module is not required.

Module Fabrication.

There are several fabrication methods that can be used to create the device's modules. For example, the device modules can be fabricated using shot injection molding (see the growth and imaging wells illustrated in FIG. 10). They can also be rapidly prototyped using such methods as a Polyjet 3D printer (FIG. 5D), fused deposition modeling (FDM), or by a stereo lithography apparatus (SLA) (FIG. 5B), as examples. Modules can also be machined or laser die cut, such as with the PSA tape shown in FIG. 1. Modules can also be laminated metal foils or plastic films (FIG. 1). Other comparable fabrication methods exist which are known to those familiar with the art.

There are many different methods that can be used to join modules together. Some examples include heat, spin, contact, and ultrasonic welding wherein plastic components are fused or melted together. Modules can also be joined mechanically such as in a press or snap fit. Adhesives such as pressure sensitive adhesive (PSA), PSA coated tapes, or various epoxies can also be used. Some materials, such as silicon based materials, can also be anodic bonded. Other comparable joining methods exist which are known to those familiar with the art.

The device modules can be fabricated from various materials. Materials compatible with imaging may have properties that include optical transparency for a given wavelength, may be minimally fluorescent at certain excitation wavelengths, or have low reflectance at certain wavelengths. The imaging surface may also require protection against dust, scratching, and contamination. This can be accomplished with physical features such as physical standoffs, a foil or plastic cover, a hinged or sliding door that can be removed by an analyzer or user before imaging occurs. Alternatively protective doors might be immobile modules. Transparent coatings or materials may also sufficiently protect the optical surface. Materials that perform mechanical actions may need a certain elasticity, such as those used for living hinges and caps (FIG. 10, 12). Materials may be selected that are favorable to fluidics and assay reagents. Some of these properties include reactivity, fluid flow, hydrophobicity, non-specific binding of samples and reagents, porosity, and hygroscopicity. Choice of materials and methods may influenced by cost and/or ease of manufacturing.

Alignment Features.

The device may have modules that allow for alignment and stacking. These can include features for device stacking (device-device alignment and stabilization) and device-analyzer alignment. Neither, either, or both types of features may be present in a device.

Device-device alignment keys may be included to improve transportability for the user (FIG. 8, FIG. 10). These may include modules or features that include physical geometries that make devices stack-able or interlock-able. These may include mating or interlocking features. The devices may stack such that they are not easily tipped over; for example, the device may be wide, with low center of gravity. Also, the device may have an overall size and shape that is easy for users to manipulate with one hand or with gloved hands.

Device-analyzer alignment keys and security features may be present to ensure the devices are inserted into the analyzer in the correct orientation and that the analyzer can interface with it properly for functions such as incubation, conveyance, magnetic selection, and imaging. The alignment features on the device may also include one or more modules that have security features. Security features are elements that may restrict access of system components to operators with a defined functional relationship with the analyzer. Device-analyzer alignment keys and security features which may comprise physical geometrical features, radio frequency identification (RF ID) tags, embedded electronics, optical fiducials, one- or two-dimensional barcodes, images, or holograms, to list a few examples.

2. Sample Input

The device may have various types of modules for accepting a sample to be tested. The device can accommodate a variety of different types of samples and modes of sample introduction. Once added to the device, a sample may be sealed into the device and experience pre-assay treatments.

Types of Samples.

Sample sources may range widely. Human samples can include for example urine, feces, blood, serum, saliva, nasal, cerebral spinal, skin, wound, and many others. Industrial samples can include food, beverages, and pharmaceuticals. And environmental samples can include water, air, or surface samples. Similarly, a great variety of sample collection devices can be used with the invention. The invention can accommodate a broad range of sample volume. The volume can, for example be less than 1 μL for a fingerstick of blood (as in FIG. 5) to greater than 1 mL for a fecal sample. The sample may have been preprocessed or not. For example, diluents or microbial growth reagents may be added to the sample before they are added to the device, or microbial growth may be allowed to occur before adding the sample to the device. Also, one or more additives may be added to the sample. For example, anti-coagulant may be added to a sample of whole blood to prevent clotting.

There are many different possible modes of sample introduction. A sample can be introduced to the device via pipette or sample collection bulb, swab, finger with drop of blood, syringe, capillary, cloth or wipe, for example. A sample may be introduced after removal from the sample collection device or a receptacle for the sample collection device can be integrated into the device. An example of an integrated sample input module is shown in FIG. 6, in which whole blood is collected by on-board lancet and capillary. An example of an externally introduced sample is in FIG. 8 in which a diluted fecal sample is pipetted into device manually by the user.

Types of Caps.

The device may have structures for sealing the sample inside. There are several different structures of closure, some examples include, but are not limited to, snaps (FIG. 4), screws (FIG. 7), press or compression fittings (FIG. 10), hinges (FIG. 10), slides, reseal-able membranes, o-ring seals, and valves including duck bill, rotary, ball, linear, and check. The cap module may integrate different parallel functions in addition to sealing. The cap may exert pressure to move the sample (FIG. 7) or release pressure such as by venting air (FIG. 5). It can mobilize liquid reagents, such as bathing swabs in buffer, as in FIG. 12, or it can include a mechanical interface with an analyzer, such as via the plunger support in FIG. 1. The cap can also perform one or more processing steps on the sample collection device. For example, the cap can cleave the handle from a nasal swab, as in FIG. 11.

The cap can integrate features that allow or limit interactions with a user or analyzer. For example, the cap can lock upon closure so that it can not be reopened by a user or analyzer. The cap can seal the sample inside the device so that it does not leak out after closure. The cap can give the user or analyzer feedback such as a sound or visual cue that the cap has been sealed properly, such as an audible click or a color change when the cap completes proper engagement. In some embodiments there may be present a window for a user or analyzer to visually determine if a sample has been correctly inserted and is ready for further processing.

On-Board Sample Pretreatment.

Once inside the device, the sample may pretreated before the contacting the assay reagents. The sample input reservoir may expose the sample immediately to the assay reagents as does the capillary tube for a blood sample in FIG. 5C in which the reaction begins immediately. Alternatively, the sample may be held temporarily in a vessel, such as a sample input reservoir (FIG. 7), until the reaction is initiated. For example, the reaction can be initiated by interaction between the device and a mechanical component of the analyzer. Liquid reagents may be added to the sample for temporary storage or pre-reaction incubation (FIG. 12). There can be pre-assay sample preparation treatments that occur automatically on the cartridge after the user closes the cap. For example, anticoagulant may be mixed with a whole blood sample, or growth media can be added to bacterial samples (FIG. 12). The pre-assay treatments can employ dry or liquid reagents. These reagents can reside inside the sample input module, or alternatively the reagents can be located elsewhere in the device. Pre treatments can be effected elsewhere in the device after the sample has left the sample input module or reservoir. For example, the sample can be combined with reagents that are dried inside a fluid flow channel and mixed with sample as it flows through the channel.

3. Dynamic Interaction with Analyzer

The device may incorporate structures to interact dynamically with an analyzer in a variety of different ways. The device may be capable of accepting materials or energy that may be transferred from the user or analyzer to specific modules of the device. It may also communicate information, such as assay status, with the analyzer or user.

The device may be compatible with direct or indirect transfer of materials or energy. For example, the device may accept one or more reagents including liquids or solids from an analyzer. An analyzer may transfer by pipette (or by other means) diluent, dye, density cushion, signaling moieties, selection moieties, or other reagents. The analyzer may interact with the device to heat, cool, or mix the device and/or its contents.

One or more portions of the fluids on the device may be mixed which may or may not require dynamic interaction with the analyzer. Methods of mixing may be passive or active. Mixing may occur passively in ways such as turbulent flows, contorted paths, low energy of solution (dried reagents in FIG. 3) that does not require interaction with an analyzer. However, mixing may also occur actively by dynamic interaction with an analyzer. Mixing may include, but are not limited to, physical motion such as by paddle or stir bar, repipetting (pipetting up and down), vibration (e.g., ultrasonic treatment), or vortexing. All, part, or none of the apparatus for mixing may be integrated into the device. For example, a stir-bar may be integrated into a device that is acted upon by an external magnetic field or an external pipette on an analyzer may be introduced to the device to mix reagents.

Liquids on the device may be moved in a way that requires dynamic interaction with an analyzer. Liquid may be moved by capillary action; for example the analyzer can bring a capillary into contact with a fluid. Other methods include a mechanical plunger (FIG. 1) or opening of a frangible seal (FIG. 2) where a blister pouch or seal between rigid vessel or channel are opened by mechanical compression such as a roller or linear actuator (Findlay, et al. 1993 Clin Chem 39, 1927-1933). Alternatively, liquid can be acted upon by an auger or screw (FIG. 7), or an external force can be applied to a deformable or collapsible solid module such as a membrane, diaphragm, bellows or accordion. Mechanical motion can open a gate or valve or bring together two physically separated components so that they are joined fluidically. A solid or liquid or gas that is used strategically to block a channel can be removed or melted or evaporated by physical energy, elevated temperature, chemical reaction, or absorption of energy such as a laser or ultraviolet light that may be introduced by an analyzer. The device may also allow direct liquid transfers such as by a pipette, as shown in FIG. 8. The device can allow an analyzer to induce changes in osmotic pressure that can induce flow of liquids, such as across a semi-permeable membrane, or changes in electrical environment, such as addition of electrical current to induce electrophoretic mobilization. Compression of a deformable matrix by an external analyzer module can induce fluid motion in a manner analogous to squeezing liquid out of a sponge. These are a few ways in which a device can interact with an analyzer to mobilize fluids.

The device may be compatible with irradiation by external energy sources. This may include acceptance of electro- or solid-state magnetic fields or electrical currents or fields. This might induce motions of entire device modules, as with a magnetic conductive component such as iron-oxide, or it might be used for sample processing, such as electrophoresis or electrochemistry. The device may have specific modules for connections to these energy sources that ensure efficient power transmission. Radio, sonic, and ultrasonic wave energy may be used to activate modules, for example switching valves that allow or block flow, or by mixing and moving liquids. The device may need modules that allow mechanical contacts for energy transmission, such as a transmission liquid in the case of ultrasonic mixing. Contacts may be included on the device to convey energy without significant loss. Coherent light, such as from a laser, or non-coherent light, such as from an unconditioned light emitting diode, may be used to open or close channels that may be fabricated from dynamic materials, that may change properties when exposed with certain light wavelengths or intensities.

Dynamic interaction with the analyzer generally includes compatibility with the analyzer's method of exerting selective force on the selection moieties. Some examples of selective forces used by analyzers include magnetic, centrifugal, buoyant, and electrical forces.

The device may also include quality control features communicate with the analyzer. For example, the device can have a window for assessing presence of adequate sample volume.

4. Detection without Washing

The invention simplifies test operation while delivering high sensitivity by employing detection and enumeration of individual labeled targets by an imaging analyzer without requiring washing steps. The invention can employ reagents (in various combinations) that support sensitive imaging without wash steps including signaling moieties, capture molecules, selection moieties, cushion, and dye.

Signaling Moieties.

The invention includes signaling moieties with photonic signaling character for optical labeling of targets. Signaling moieties can be target-specific labels such as labeling particles; for example, fluorescent particles conjugated to target-specific antibodies. Signaling moieties can be non-specific labels that bind to a broad class of analytes, for example, propidium iodide, which labels DNA and cells that have DNA that is accessible to the reagent.

Selection Moieties or Capture Molecules.

The invention includes selection moieties or capture molecules which are generally used for specifically depositing labeled targets onto the detection surface. This step separates or distinguishes the labeled targets from free label and other labeled entities. Selection moieties use force to achieve the deposition of targets on the detection surface and can include, for example, target-specific paramagnetic particles or dense target-specific silica particles. Capture molecules can be used to coat the detection surface for specifically capturing targets.

Cushion.

The invention can include a high density cushion for excluding unselected components of the reaction from the detection zone. The cushion is a liquid layer which is of higher density than the bulk reaction between the bulk of the reaction components and the detection surface before beginning the process of depositing selection moieties onto the detection surface. The cushion can include various density agents singly or in combination (and at various concentrations) including for example, sucrose, diatrizoate, iodixanol (tradenamed Optiprep®), NaCl, CsCl, Percoll®, metrizamide, or albumin.

Dye.

The incorporation of an appropriate dye into the assay of the invention can effect optical separation to support sensitive detection in the device without wash steps. The dye increases the discrimination of signaling moieties that are in the detection zone from signaling moieties that are not in the detection zone. When the reaction medium is substantially transparent to excitation light or other illuminating light, as well as to reflected or emitted light producing the imaging signal, unbound label which is outside of the detection zone can contribute a large nonspecific optical signal to the image. Inclusion of a dye into the reaction before imaging can be used to eliminate or reduce the signal produced by unbound label residing outside of the detection zone. Dye at an appropriate concentration allows detection of fluorescence in the detection zone at or near the detection surface, while masking the signaling contribution from unbound label in the remainder of the solution. When the signaling moiety is fluorescent, the dye used can have an absorbance of light overlapping the excitation or emission wavelengths of the fluorescent signaling moiety, or can absorb both exciting and emitted light. For example dyes that are useful in the invention when the fluorescent signaling moiety is yellow-green in color, include Chromotrope 2R and Acid Red 1. Many other dyes appropriate in this and other spectral regions are known to those familiar with the art.

Dyed Cushion.

The combination of the dense cushion layer and dye provides an efficient method for imaging labeled targets without washing. This approach can eliminate background signal due to unbound signaling moieties and labeled entities other than the target. The cushion can ensure that only targets drawn through the dense layer by virtue of their association with selection moieties reach the detection zone. The dye prevents the detection of signal due to the free signaling moieties in the overlying bulk reaction mixture thereby isolating the signaling contribution of labeled targets complexed to selection moieties deposited within the detection zone.

5. Liquid Reagents

The device can contain on-board liquid reagents that can be held and mobilized in various ways.

Types of Liquid Reagents.

Liquid reagents can include solutions containing signaling moieties and/or selection moieties, cushion reagents, dyes, diluents, additives (e.g., detergents or anticoagulants), growth media (which may also include antibiotics), blocking agents, internal controls, and other reagents that are known to those skilled in the art. Liquid reagents can have simple or complex composition.

Reagent liquids may be sterilized. Sterilization may occur by methods such as, but not limited to, exposure to ultraviolet radiation, heat (e.g., autoclave), or ethylene oxide, by filtering, or by addition of one or more preservative agents (e.g., ProClin (Supleco), sodium azide). Sterilization of reagents may be done before or after introduction to the device.

Liquid Reagent Containment.

The liquid reagents may be contained in different concentrations and volumes. Liquids can be present in volumes as small as less than 1 μμL or as much as more than 1 mL. Concentrations can range from a pure sample to a dilution of less than one part per million. The liquids may have different methods of containment, including one or more pouch or blister (FIG. 2), wells or vessels (FIG. 13), capillaries (FIG. 5), or channels. These are only a few examples of possible liquid containment, further details are included in section 6. Fluidic System. Liquid reagents may require sterilization during manufacture or aseptic filling.

There may be one or more modules to keep humidity away from dried reagents. One example is a frangible seal (FIG. 2) that is located between a region of liquid and dried reagents. Other methods of keeping dried reagents dry include valves, reseal-able or hydrophobic membranes, o-rings or other gasket materials. Mechanically movable parts can also be used to contain humidity, including two parts that snap (FIG. 4), screw (FIG. 7), or press (FIG. 10) together. Mechanical parts can also incorporate a slide or a hinge such as the living hinges in elastomeric plastic illustrated in FIG. 10. Other sealing techniques exist that are not listed here, but are known to those familiar with the art.

Methods of Liquid Mobilization.

Liquids can be mobilized in a wide variety of ways that can be either passive or active. Passive means, such as capillary action, can induce flows by molecular-level interactions of surface tension. Such is the case with blood samples inserted into the narrow channels of the device in FIG. 5. Other passive liquid handling methods include differences in osmotic pressure such as across a semi permeable membrane or by differences in electrical environment, among others. Fluid flow in a channel can be either passive, in the case of capillary action, or active if it is under applied pressure.

Active liquid mobilization requires a pressure gradient to be induced across a liquid. There are many ways to mobilize liquids in this manner. A fluid can be acted upon by a plunger as in FIG. 1 or FIG. 9, a screw as in FIG. 7, or by direct linear actuation as illustrated in FIG. 12. This mobilization module can be either external or integrated into the cap module, such as the screw in FIG. 7, the plunger in FIG. 9, or the tabs in FIG. 12. Fluid can also be mobilized by a deflection of a solid device, such as in the deformation membrane or diaphragm, or the collapse of a bellows or accordion. Other examples of active liquid mobilization are known in the art.

Other ways of active liquid mobilization include blister pouches, frangible seals, and combinations of the two. Liquid can be sealed into a blister pouch and released by applying pressure to the deformable module until it bursts. Likewise, a frangible seal can be designed to fail at specific pressures so that liquid is mobilized after specific forces have been applied behind a bolus of liquid. A liquid reagent contained inside a blister pouch that has been sealed by a frangible seal can be mobilized by a roller mechanism, such as illustrated in FIG. 2. By packaging reagents into modular pouches, longer shelf life and reliability may be achieved. A frangible seal can be used with or without a blister. The simplicity of the roller mechanism can ensure robustness; for example, the possibility for unidirectional fluid motion can limit back flow and cross flows. The roller mechanism can be placed on-board or off-board the device. Use of a roller for moving liquids in a different type of device was illustrated by Findlay (Findlay, et al. 1993 Clin Chem 39, 1927-1933).

There are other active mobilization processes that integrate mechanical motions. In some cases, a mechanical action will open a gate such as a valve. Valves come in a wide variety of type and include examples such as pinch, rotary, check, or duck bill valves. Other mechanical motions, such as compression of a deformable absorbent matrix can induce liquid motion, in a manner analogous to squeezing liquid out of a sponge. A wide variety of absorbent materials that have a specific absorbency and volume can be used to this effect. In another example of mechanical motion, two physically separated components are brought together and aligned that were previously non-contiguous.

Other methods to actively mobilize liquids include removal of a solid or liquid or gas that strategically blocks a channel. This can be done by physical movement, melting, or evaporation by elevated temperature, chemical reaction, absorption, or exposure to radiation, such as ultraviolet light. Samples can also be physically moved by direct liquid transfer, such as by pipetting. Liquid mobilizations by pipette are shown in FIG. 8 and FIG. 13.

Any combination of one or more of the above mobilization methods can be envisioned to create complex liquid handling schemes. One example is shown in FIG. 12, where a liquid is first mobilized by movement of tabs in the cap, which compress a blister pouch and open a frangible seal. Once the frangible seal is opened, liquid flows through a channel by capillary action to the sample input wells. Numerous alternative combinations of fluid mobilization methods can be envisioned.

6. Dried Reagents

The device may contain on-board dried reagents. The dried reagents can be of many different types, requiring various preparation methods. They can be contained and rehydrated in a number of different ways.

Types of Dried Reagents.

Dried reagents included in the device can include solutions containing signaling moieties and/or selection moieties, cushion reagents, dyes, diluents, additives (e.g., detergents or anticoagulants), growth media (which may also include antibiotics), blocking agents, internal controls, and other reagents that are known to those skilled in the art. These reagents may be combined as admixtures or layers of admixtures, depending on functionality requirements of the device.

Dried Reagent Containment.

The dried reagents may be contained in different amounts. They can be present in weights as small as less than 1 mg or as much as more than 1 g. Concentrations can range from a pure sample to a dilution of less than one part per million. The dried reagents may have different methods of containment, including one or more pouch or blister, well or vessel, capillary, or channel. These are only a few examples. Dried reagents may require sterilization during manufacture or aseptic filling.

There may be one or more modules to keep humidity from the dried reagents. One example is a frangible seal (FIG. 2) that is located between a region of liquid and dried reagents. Other means of keeping dried reagents dry include valves, reseal-able or hydrophobic membranes, o-rings or other gasket materials. Mechanically movable parts can also be used to contain humidity, including two parts that snap (FIG. 4), screw (FIG. 7), or press (FIG. 10) together. Mechanical parts can also incorporate a slide or a hinge such as the living hinges in elastomeric plastic illustrated in FIG. 10. Other examples are detailed above.

Methods of Preparation.

There are a variety of ways in which the dried reagents can be prepared. The goal of drying reagents is to extend the shelf life of devices by protecting reagents from humidity. The method for drying reagents should be such that reagents retain their original functionality following rehydration.

There are a several different methods of drying reagents. Lyophilization or freeze drying (Example 3) can be used to dry one or more layers of reagents inside device modules such as a well or channel or pouch. Lyophilized reagents can include a layer of cushion, dye, or binding moieties. Alternatively, reagents can be lyophilized separately and added to the device modules during device assembly. Other methods of dry reagent preparation might include air drying or evaporation, silk screening, vapor deposition, precipitation from solution, or chemical reaction, to provide a few examples.

Methods of Resuspension.

The dried reagents can be rehydrated by adding liquid in a number of different ways. Resuspension may occur passively such as by a liquid and dried reagent mixing in turbulent flows, contorted paths, or by readily absorbable dried reagents. An example of a readily absorbable dried reagents is described in Example 3. Alternatively, resuspension may be achieved by active mixing, for example by a paddle, stir bar, repipetting, vibration, vortexing, or nutation.

7. Fluidic System

For an assay to occur, the sample and reagents are brought together via a fluidic system. The fluidic system may include movement of liquids, solids, and gasses in a precisely controlled manner.

The fluidic system can have a wide range of complexity. It can be as simple as pipetting manually into a single vessel that contains dried reagents (FIG. 4) or as complex as a multifunctional device with numerous multiplexed fluidics processing steps (FIG. 12). The device can utilize fluidics management methods that are entirely manual, entirely automated, or a combination of both. An entirely manual device example includes the one shown in FIG. 4 in which a user pipettes the sample directly into a well containing dried reagents. Alternatively, fluid management can be entirely controlled by the device, such as in FIG. 5 where whole blood is metered by capillary flow and is entirely internal to the device. Fluid management can also be managed partly or entirely by analyzer functions, such as in FIG. 7, where the analyzer meters liquid movement into the imaging wells through actuation of a screw cap.

Methods of Liquid Mobilization.

Liquids can be mobilized in a wide variety of ways that can be either passive or active. Passive means, such as capillary action, can induce flows by molecular-level interactions of surface tension as with the blood samples inserted into the narrow channels of the device in FIG. 5. Other passive liquid handling methods include differences in osmotic pressure such as across a semi permeable membrane or by differences in electrical environment, among others. Fluid flow in a channel can be either passive, in the case of capillary action, or active if it is under pressure.

Active liquid mobilization requires a pressure gradient to be induced across the liquid. There are many ways to mobilize liquids in this manner. A fluid can be acted upon by a plunger as in FIG. 1 or FIG. 9, a screw as in FIG. 7, or by direct linear actuation as illustrated in FIG. 12. This mobilization module can be either external or integrated into the cap module, such as the screw in FIG. 7, the plunger in FIG. 9, or the tabs in FIG. 12. Fluid can also be mobilized by a deflection of a solid device, such as in the deformation membrane or diaphragm, or the collapse or expansion of a bellows or accordion.

Other means of active liquid mobilization include blister pouches, frangible seals, and combinations of the two. Liquids can be sealed into one or more blister pouches and released by adding pressure to a deformable region until it bursts. Likewise, a frangible seal can be designed to fail at specific pressures so that liquid is mobilized after specific forces have been applied behind a bolus of liquid. A liquid reagent contained inside a blister pouch that has been sealed by a frangible seal can be mobilized by a linear actuator or a roller mechanism, such as illustrated in FIG. 2. By packaging reagents into modular pouches, longer shelf life and reliability may be achieved. Frangible seals can be used with or without a blister. A roller mechanism may be used (Findlay, et al. 1993 Clin Chem 39, 1927-1933). The possibility for controllable, directional motion using a roller-type mechanism can limit back flow and cross flows or even be used for mixing. The roller mechanism can be integrated on-board or placed off board the device.

There are other active mobilization processes that integrate mechanical motions. In some cases, mechanical action can open a gate such as a valve. Valves come in a wide variety and include examples such as pinch, rotary, check, or duck bill valves to name a few. Other mechanical motions, such as expansion or compression of a deformable absorbent matrix can induce liquid motion, such as squeezing liquid out of or into a sponge. A wide variety of absorbent materials that have a specific absorbency and volume can be used to this effect. In another example of mechanical motion, two physically separated components are brought together and aligned that were previously non-contiguous.

Other methods of actively mobilizing liquids include removal of a solid or liquid or gas that is strategically blocking a channel and can be removed or melted or evaporated by elevated temperature, chemical reaction, absorption, or exposure to radiation, such as ultraviolet wavelength light. Samples can also be physically moved by direct liquid transfer, such as by pipetting. Liquid mobilizations by pipette are shown in FIG. 8 and FIG. 13.

Any combination of one or more of the above mobilization methods can be envisioned to create complex liquid handling schemes. One example is shown in FIG. 12, in which liquid is first mobilized by linear motion of tabs in the cap. Closure of the cap results in a compression of a blister pouch that opens a frangible seal. Once the frangible seal is opened, liquid flows through channels by capillary action to the sample input wells. Numerous alternative combinations of fluid mobilization methods can be envisioned to create any number of unique schemes.

Onset of Flow.

There are many ways to control onset and timing of fluidic motion. A frangible seal (FIG. 2), reseal-able membrane, or valve can prevent fluid from moving until the proper time. O-rings can be compressed or relaxed to control flow. And mechanically movable components that mate with one another in specific ways can be used to control flows. Examples include, but are not limited to, snaps (FIG. 4), screws or augers (FIG. 7), pressed fits (FIG. 10), hinges (FIG. 10), or slides.

Surface treatments can be used to modify flow characteristics by introducing hydrophobic or hydrophilic regions on the device. These regions can be created by environmental treatments such as placing modules in oxygen plasma, corona, ionically charged chambers. Modules can also be exposed to other types of treatments, including but not limited to, chemical etchings, vapor and liquid depositions, and chemical coatings. Onset and direction of flow can also be effected by material selection and processing, including surface texture and roughness.

Metering Fluids.

Fluid can be precisely metered and delivered to one or more parallel or serial vessels. Metering can be controlled externally through mechanical displacement of a device-analyzer fluidics interface. It may include one or more of the following modules that include a variety of passive and active methods.

Fluids can be actively metered in a number of different ways. Active fluid metering can include moving a plunger (FIG. 9), compressing a blister pouch with or without roller (FIG. 2), controlled rupturing of a frangible seal (FIG. 2), turning of an auger or screw (FIG. 7), deforming a membrane, diaphragm, bellows or accordion. Fluids can also be directly transferred by pipetting (FIG. 4).

Passive metering can occur in several ways. One way may include a module in part or completely controlled by geometric designs that equalize resistance to flow, for example by surface tension or by capillary action (FIG. 5). Metering also can be done with a fill to a hydrophobic or hydrophilic boundary region. In this case, liquid displaces gas or air, but stops at a hydrophobic membrane or boundary (FIG. 7) that it cannot readily pass. Another passive embodiment can include metering using a vacuum filled region. A self contained vacuum in a well or vessel can be opened to a fluid volume that was backed by a higher pressure, such as atmosphere. Releasing the boundary between the vacuum region and the liquid can result in a specific liquid volume being metered into the formerly evacuated region as the liquid rushes in to equilibrate the region of low pressure.

The same features used for precisely metering can be used for timing.

Preventing Leakage.

The device may have features for liquid containment and preventing leakage. Containment modules may include wells, blisters, bibulous membranes, vessels, and channels, for example. Boundaries that contain fluid flows, control the physical location and paths of movement of a sample, and prevent leakage may be made from a solid, liquid, or gas.

There are various ways to prevent leakage before, during, and after pre-processing and assay reaction steps. Immobile solid containments include, but are not limited to, channels, wells, vessels, and chambers, including pipette tips and bulbs. There are also pads or membranes.

Fluids can be used to keep another liquid contained, such as by focused flow, an emulsion, or a suspension of two immiscible fluids, to list a few examples. These liquids can be either static or in motion.

Flows can be contained by mechanically movable solid parts which may include two parts that fit together by snapping (FIG. 4) or press fit (FIG. 10), a screw (FIG. 7), a hinge (FIG. 10), slide, o-ring, valve, frangible seal (FIG. 2) or resealable membrane.

The fluid may need to displace trapped air, therefore venting methods may be included to minimize trapped gases inside wells or channels. There are many ways to vent air. A few examples include hydrophobic membranes (e.g., Versapor-800R; Pall), other membranes, vacuums or low pressure regions, displacement or compression of another liquid, gas, or deformable solid such as a diaphragm, a capillary or large hole open to atmosphere, or a porous solid.

During metering and after it is completed, there may be a need to minimize crossover or backflow. Divided samples may need to remain divided through optical interrogation. Preventing backflow may be achieved by using a membrane, a valve, or a bubble of air or immiscible fluid, such as oil with an aqueous sample.

Mixing. The device may have features that allow mixing of fluids with other liquid or dried reagents. Mixing may occur passively or actively. Passive mixing may include means such as turbulent flows, contorted paths, or low energy of solutions such as adding liquids to dried reagents (Example 1). Active mixing includes but is not limited to physical motions such as a rotating or oscillating paddle or stir bar, repipetting (pipetting up and down), vibrational such as ultrasonic waves, or by vortexing or nutating.

8. Intermediate Processing

Device modules for intermediate processing steps are required for certain testing applications and sample types. Intermediate processing steps include, but are not limited to, those for heating, cooling, mixing, growth, and filtration. The complexity of the intermediate processing modules can range from devices as simple as those in which no intermediate processing modules are necessary (FIG. 4) to one as complex as FIG. 12 in which multiple pre-processing steps occur before an assay reaction takes place.

Incubation Modules.

A device may include sample processing modules that are compatible with heating or cooling. Temperatures can be externally controlled, such as by an incubator inside an analyzer for example. In this case, modules and bonding methods may need to withstand incubation conditions. For example, the device illustrated in FIG. 10 analyzes MRSA, which may incubate a sample for several hours at 37 degrees Celsius. Temperatures can be also be controlled by a module integrated into the device, such as a local heating element which may or may not contain an integrated power source or means to connect to an external power source. Internal temperature can also be changed by internal modules that might undergo chemical reactions such as when calcium chloride or magnesium sulfate or sodium acetate is mixed with water to produce a local exothermic reaction.

Mixing Modules.

The device may have features that allow mixing of fluids with other fluids or dried reagents. Mixing may occur passively or actively. Passive mixing includes methods such as turbulent flows, contorted paths, or low energy of solutions such as adding a liquid to a lyophilized reagent (Example 1). Active mixing includes but is not limited to physical motions such as a rotating or oscillating paddle or stir bar, repipetting such as pipetting up and down, vibrational such as ultrasonic waves, or by vortexing or nutating.

Separation Modules.

Samples may contain particulates or other substances that can interfere with the assay. To mitigate this problem, a separation method may be utilized to remove detritus of a particular size. There are many different separation methods available that include, but are not limited to, filtering through a porous solid, fibrous mesh, membranes, woven meshes, liquid separations such as utilization of field flow fractionation, electrophoretic or electro-osmotic flows, or chemical reactions. One example is illustrated in FIG. 9, in which a fibrous mesh (Filtrona R26758) is utilized to exclude particles in solution that are larger than the order of 100 microns in diameter. The filtration module in this example can be modified to exclude particles in a sample of larger or smaller diameters as required by the assay. A similar method can be used to remove specific agents in a sample, such as blood cells or certain proteins. Unwanted moieties in a sample solution can be removed. For example, with specific antibody capture, such as passing a sample through a porous media with antibodies chemically bound, certain proteins that may affect an assay can be removed or changed in concentration as a pre-assay step.

Growth Modules.

Modules may be present for assays that require growth. The growth module may have dried or liquid reagents for growth, and may be combined with or without antibiotics. For the full detail of growth reagents, see sections 4 and 5 above. The growth module may require boundaries that contain fluid flows and prevent leakage. These may be made from a solid, liquid, or gas that control the physical location and paths of movement of a sample, such as channels, wells, vessels, chambers, pipette tips, bulbs, pads, membranes, focused flow or other liquid boundaries including emulsions of two immiscible fluids, acoustic and ultrasonic waves, or any combination of materials that do not mix with one another. Additional examples are listed above.

Growth modules can be contained by one or more mechanically movable parts which may snap (FIG. 4), screw (FIG. 7), press together (FIG. 10), hinge (FIG. 10), or slide. Containment can also occur with o-rings, valves, frangible seals (FIG. 2) or resealable membrane.

The growth module may need to displace trapped air or allow aeration for a sample to grow. Examples include hydrophobic membrane (such as Pall Versapor-800R used in FIG. 1), membrane, capillary hole or other physical opening, a porous solid or other methods listed above.

During growth there may be a need to minimize crossover or backflow or premature forward flow. This might be accomplished by specific device module geometries, such as a change in aspect ratio from a large well to narrow capillary in which surface tension stops forward flow. Other embodiments include, but are not limited to, a membrane or filter, a bubble of gas or immiscible fluid such as air or oil, a valve, a frangible seal, immiscible liquid such as silicone oil soaked cotton plug compatible with the gate in FIG. 9. Various other examples of containment and venting of fluids apply here and are detailed in section 6.

9. Selection

The device is compatible with a method for depositing targets on the detection surface. Specific selection can be useful because it can dramatically lessen the background signal of unbound labels and non-specifically bound labels in the detection zone. It is also advantageous because it can gather all target moieties into the detection area for optimal imaging.

Some devices may capture targets on an imaging surface coated with target-specific binding moieties, for example, antibodies or oligonucleotides. Alternatively, the device may contain target-specific selection moieties such as magnetic particles coated with target-specific antibodies. A magnetic field can be applied to such a device resulting in deposition in the detection zone of the magnetic particles complexed with labeled targets. Other types of capture use centrifugation, sedimentation, buoyancy, electrophoresis, or filtration.

The devices of the invention generally have an imaging well in which the target complexed to selection moieties can be deposited directly onto a detection area. Linear projection of a volume directly onto a surface can enhance sensitivity by allowing dispersion of the labeled complexes across the detection area. Such dispersion allows detection and enumeration of individual labeled target complexes. For example, in FIG. 4, dried reagents may include magnetic particles that are pulled down to the bottom of well in which they can be imaged from below. Alternative embodiments include selection to other surfaces, such as the sides or top of the imaging well. The selection can be done in the absence of flow.

10. Imaging

The devices have one or more imaging wells with an imaging surface or detection area onto which labeled targets are deposited by selection for subsequent detection by imaging. Imaging wells typically have properties and features that support optical detection of labeled targets. These properties and features may include optically appropriate materials, geometries, and fiducial features for focusing.

In general, the face of the imaging well that includes the detection area is optically transparent with properties that are well-suited for detecting the signaling moieties used to label the target. For example, if fluorescence is to be detected, the optical window should be non-fluorescent at wavelengths in the corresponding spectral regime of the target. The imaging well would also have low reflectance of incident light at specific wavelengths that might also interfere with imaging by increasing background signal.

The image surface may be protected against dust, scratches, and contamination. This may be beneficial in limiting nonspecific background or artifacts that may complicate imaging. Some means of protecting the surface include incorporating physical standoffs, feet, or barriers (FIG. 4 and FIG. 8), or by covering the optical surface with a foil or plastic cover. Alternatively, a door that is hinged or slides can be used to protect the surface. These protective features can be removed by an analyzer or user before imaging occurs or can be removed automatically by the device. Alternatively, these features might not be mobile features, as would be the case with protective or scratch-resistant coatings.

An imaging module may have one or more features to aid with focusing an image. These features may include optical fiducials such as images or objects in one- two- or three-dimensions, including barcode. Alternatively, focusing can be accomplished using mechanical registration features such as v-grooves or alignment pins or other physical features on the device. An example of focusing alignment features includes the feet on FIG. 4 and device-analyzer alignment features in FIG. 9.

A variety of geometries are possible for the imaging module. Imaging can occur from the bottom, top, or side, so the imaging module can be designed to accommodate any of these configurations.

The imaging module may be fabricated from many different materials. The material selection depends on the target and imaging method, but can be a plastic such as a cyclic olefin copolymer as in FIG. 10, acrylics, polystyrenes, and other transparent materials. It can also be fabricated from glasses such as borosilicate glass, fused silica, quartz, or others. Other materials might include, but are not limited to PDMS, RTV, optical adhesives, and laminates. The imaging module may have built in optical filtering functionality which may include a coating or structural composition, such as a laminate or additional physical layer that block or absorb certain wavelengths of energy.

11. Information Management

There may be one or more modules that assist in the transmission and pairing of patient information and test results. Information management modules may be compatible with analyzer read methods, allowing automated results communication and tracking which may decrease rates of error. These modules may include, but are not limited to, those compatible with optical interrogation by CCD or barcode reader such as a one- or two-dimensional barcode (FIG. 8), image, hologram, handwritten label, or physical geometry such as an imprinted numeric sequence or code. Electrical signals can be embedded into the device and read by external detection of a voltage change, or signal emission such as radio frequency (RF ID, FIG. 6) can be excited and read. The device may or may not be externally read by a user or analyzer in any of the above cases.

12. Packaging

Each device may or may not be delivered to the user in an external package. The external packaging may vary depending on the assay test, the venue in which the test is performed, and the lot size of devices required at a venue. External packaging may convey information important to the user such as assay type and shelf life.

External labeling information may be present for communicating contents to the user and for tracking. External package labeling may include information such as lot number, test type, number of units, kit contents, directions for use, warnings to specific hazards, expiration date, as well as other useful information. Analyzer or user read tracking information may be present, including any of those described in section 11 Information Management. Some means of information management on external packaging include transmission through optical interrogation, CCD, barcode reader, electrical or other signal emission, such as radio frequency, or by physical geometry. Packaging information can allow tracking by lots for quality control management. Shelf life information may be communicated to the user, so that expired devices can be replaced in a timely manner. A tamper-resistant seal may be included to indicate if a device has been previously opened or modified in a way that may adversely affect assay results.

Packaging allows grouping of all necessary assay modules into assay-specific kits. Kits may include one or more sample collection modules that may include, but are not limited to, a sample collection bulb or pipette, a swab (FIG. 11.1), a lancet or other finger stick device (FIG. 6), a capillary, or syringe. One or more sample collection modules may be included per package. The modules in a kit may be identical or different modules, for example two swabs or a lancet and a capillary may be included in one kit. One or more device or kits may be included per package.

There may be assay dependent packaging inserts and treatments that can control the environment around and inside the device, such as sterilization (FIG. 6), anticoagulant for blood samples (FIG. 6), and humidity or desiccation (FIG. 11).

EXAMPLES

The invention is further described with respect to the following nonlimiting embodiments. Unless otherwise noted, any element of a device specifically described in the examples may be employed generally with a device or kit of the invention.

Example 1. Use of Liquid Reagents to Image Individual Labeled Target Complexes

Overview.

There are various forms and ways to stabilize the reagents that are placed on the device. This example details one method for housing liquid reagents including target-specific fluorescent particle signaling moieties, target-specific magnetic selection moieties, and a dye cushion reagent (this reagent reduces assay background and allows assay of target in a imaging well without washing) and other assay components. The reagents in this example were dispensed in layers in multiple pipetting steps. This example teaches how to formulate the liquid reagents so that they can be used to perform an assay on a human plasma sample to measure the concentration of human thyroid stimulating hormone (hTSH).

Methods.

Anti-hTSH antibody labeled fluorescent particles (anti-hTSH FP) were prepared by chemically linking carboxylated 500 nm fluorescent particles (Invitrogen cat #8813) with free amino groups on mouse monoclonal anti-human thyroid stimulating hormone (Meridian OEM cat. #MAT04-005) antibodies using a two step carbodiimide and N-sulfohydroxysuccinimide reaction using a standard method (Bioconjugate Techniques, Herrmanson Academic Press, 1996). Anti-hTSH antibody labeled magnetic particles (anti-hTSH MP) were prepared by chemically linking carboxylated 292 nm magnetic particles (Ademtech cat #0213) with free amino groups on mouse monoclonal anti-human thyroid stimulating hormone (Thermo Serdyn cat. #MIT-0409) antibodies using a two step carbodiimide and N-sulfohydroxysuccinimide reaction using a standard method (Bioconjugate Techniques, Herrmanson Academic Press, 1996).

Recombinant hTSH (CellSciences cat #CRT505B) was added at known amounts to human plasma previously depleted of hTSH to generate a standard curve (FIG. 17).

A reaction of 10 µL of a 0.007% w/v dilution of anti-hTSH antibody labeled fluorescent particles and 10 µL of a 0.05% w/v dilution of anti-hTSH antibody labeled magnetic particles were mixed with 10 µL 200 mM EPPS (Sigma-Aldrich cat #E9502) buffer, 400 mM 1,3 diaminopropane (Sigma-Aldrich cat #D230807) pH 7.8, 10 µL of 1 mg/mL Alginic acid (Sigma-Aldrich cat #A2158), 2.5% w/v polyvinylpyrrolidone (Sigma-Aldrich cat #PVP40), 0.5 mg/mL bovine gamma globulin (Lampire Laboratories cat #7400805), 1 mg/mL mouse gamma globulin (Jackson Imunno Cat #015-000-002) in 10 mM phosphate, 140 mM sodium chloride, 3 mM potassium chloride (Calbiochem cat #524650) pH 7.4 and 10 µLµL of plasma sample was formed, mixed, and incubated for 10 minutes. In another well, 90 µL of cushion dye reagent 2 mg/mL Chromotrope R2 (Sigma-Aldrich cat #C3143) and 25% v/v Optiprep® (a 60% w/v solution of iodixanol) (Sigma-Aldrich D1556) in 20 mM Tris (JT Baker cat #4109-02), 0.05% w/v Tween 20 (Acros cat #2333600010), 2 mg/mL Bovine serum albumin (Sigma-Aldrich cat #A3059), 0.05% w/v ProClin 300 (Supleco cat #48912-U) was added. At the end of the incubation a 40 µL aliquot of reaction mixture was layered on top of the dye cushion layer. The wells were then placed on a bar magnet and the immunocomplexes selected magnetically for 5 minutes and deposited on the bottom of the well. The bar magnet used a configuration of 22×22×100 mm permanent magnets depicted in FIG. 20. The well was then placed in a high throughput analysis automated analyzer (FIG. 19). The wells were then imaged on the analyzer at a 0.1 second exposure time. Individual fluorescent particles were enumerated using imaging software.

Samples were processed by an automated analyzer (FIG. 19). The user placed the sample into the analyzer input for automatic processing. A programmable 3-axis stage was programmed to focus on the imaging wells of each device, capture an image using non-magnified, large area imaging and analyze the results. Image analysis was performed by first preprocessing the image to find the region of interest and compensate for distortion or lighting effects. Next, signal components were separated from background using a thresholding process followed by connectivity analysis. These components were sorted based on measured parameters to remove non-signal items such as debris. Finally, a result was computed based on signal statistics which include component count and total component intensity.

Results.

The data (FIG. 17) was analyzed and graphed as TSH concentration versus fluorescent particle number, and the data demonstrate a dose-response and the sensitivity of the assay for hTSH.

Conclusion.

The example demonstrates a sensitive test for human thyroid stimulating hormone in human plasma using large area imaging and liquid reagents including target-specific signaling moieties, and target-specific selection moieties.

Variations.

There are many ways in which liquid reagents can be incorporated into the device, as are described in the Fluidic System section of the detailed description above. Important variations include instances in which liquids are manufactured and stored on the device and in which liquids are dispensed into the device by an analyzer. Reagents also can be any combination of liquid and solid, including dried or lyophilized reagents. Liquids can be contained and mobilized by a blister pouch, which can increase shelf life of the liquid reagent, allow for repeatable results, and simplify manufacturing and assembly of devices.

Example 2. Stabilization of Reagents by Lyophilization

Overview.

There are various ways to stabilize the reagents contained in the device. Drying reagents within the device can increase stability while maintaining functionality, ultimately improving the shelf-life of the device. A longer shelf-life device can decrease costs to the user by ensuring devices will yield accurate results over longer periods of time. This example shows stabilization of reagents by lyophilization of dye-cushion, target-specific immunoparticles, and other reagents.

This example teaches how to formulate dried reagents using lyophilization that can be readily rehydrated upon introduction to liquids without a specific module for mixing. On-board reagents can be lyophilized as one or more layers in one or multiple freeze-drying steps with the methods below to prepare a single layer, discrete spheres, or dual layer reagents.

Method.

Reagents were lyophilized for an assay for human thyroid stimulating hormone (hTSH) in separate dried spheres.

Lyophilized Dye Cushion Layers.

A Dura-Stop lyophilizer was pre-cooled to −45° C. 10 µL of dye-cushion reagent (made as described in Example 1 with the following modifications: 5% w/v trehalose (Sigma-Aldrich cat #T9449) was included to the reagent) was pipetted into specific wells of a black-walled 384-well microtiter plate. The plate was placed in the lyophilizer and the reagent layer allowed to freeze for 1 hour. Then vacuum was applied, and the plates were lyophilized at −45° C. for 16 hours. After the first phase, the temperature was set to −5° C. for 6 hours, followed by 25° C. for 2 hours to complete the lyophilization. The lyophilizer power was turned off and the vacuum released. The plates were removed and covered with a self-adhesive film and stored in desiccation chamber until use.

Lyophilization of Fluorescent and Magnetic Particle Spheres for Human Thyroid Stimulating Hormone.

Lyophilized spheres of 5 µL of a mixture of 160 mM EPPS (Sigma-Aldrich cat #E9502) buffer, 320 mM 1,3 diaminopropane (Sigma-Aldrich cat #D230807), 5% w/v trehalose (Sigma-Aldrich cat #T9449), 0.003% w/v dilution of anti-human thyroid stimulating hormone fluorescent particles, 0.08% w/v dilution of anti-hTSH MP (described in Example 1) pH 7.6 were made by accurately pumping 5 µL drops of the mixture into a insulated beaker of liquid nitrogen. The frozen spheres were then immediately placed in Dura-Stop precooled to −45° C. The vacuum was applied immediately and the spheres were lyophilized for 16 hrs, the lyophilizer was brought to −5° C. for 4 hours and then 25° C. for 1 hour.

Dried reagents were stored in a low humidity environment until use. The resulting reagent spheres (FIG. 5E) can be manually placed, either by hand or by automated robotics, into specific locations on a device for use.

Assay Comparing Dried Thyroid Stimulation Hormone Reagents with Liquid Reagents. Recombinant hTSH (CellSciences cat #CRT505B) was added to a solution of 10 mM phosphate, 140 mM sodium chloride, 3 mM potassium chloride (Calbiochem cat #524650), 0.05% w/v Tween 20 (Acros cat #2333600010), 2 mg/mL bovine serum albumin (Sigma-Aldrich cat #A3059), 0.05% w/v ProClin 300 (Supleco cat #48912-U) pH 7.4. Two different solutions were made (a) 250 pg/mL hTSH and (b) 62.5 pg/mL hTSH. Lyophilized spheres of fluorescent and magnetic anti-hTSH particles (lyophilized as described above) were placed on top of specific wells containing lyophilized dye-cushion reagent. In a separate 384 well black walled microtiter plate 10 µL of dye cushion reagent (as described in Example 1 with the following modifications: 5% w/v trehalose (Sigma-Aldrich cat #T9449) was included) was pipetted into specific wells. A 5 µL aliquot of the 250 pg/mL solution of TSH was added to 5 µL of a mixture of 160 mM EPPS (Sigma-Aldrich cat #E9502) buffer, 320 mM 1,3 diaminopropane (Sigma-Aldrich cat #D230807), 5% w/v trehalose (Sigma-Aldrich cat #T9449), 0.003% w/v dilution of anti-human thyroid stimulating hormone fluorescent particles, 0.08% w/v dilution of anti-hTSH MP and incubated for 10 minutes in specific wells of a 96 well polycarbonate PCR plate. After incubation 7.5 µL of this mixture was layered onto of the liquid dye-cushion wells. During the incubation of the liquid reagents 20 µL of the 62.5 pg/mL solution of hTSH was carefully pipetted on top of specific wells of lyophilized reagents. The plates were then placed on a bar magnet and the immunocomplexes selected magnetically for 5 minutes and deposited on the bottom of the well. The bar magnet used a configuration of 22×22×100 mm permanent magnets depicted in FIG. 20. The plates were then placed in a high throughput analysis automated analyzer (FIG. 19). The wells were then imaged on the analyzer at a 0.1 second exposure time and processed as described above Results.

FIG. 22A shows a bar graph of the percent recovery of hTSH in the lyophilized wells compared to the liquid reagent wells (Liquid reagents were assigned as 100% recovery). FIG. 22B shows actual images from samples with 0 pg/mL and 250 pg/mL TSH using lyophilized TSH reagents. The recovery of hTSH using lyophilized reagents is similar to liquid reagents with the experimental error of the assay.

Conclusions.

The data demonstrate that lyophilized reagents can be used in an assay and perform as well as liquid reagents.

Variations.

There are other alternative embodiments of this example. Example 13 demonstrates lyophilization dye-cushion and assay reagents in a single well resulting in two liquid layers upon rehydration. Lyophilization conditions, such as temperatures and times can be adjusted, and various reagents, in addition to those listed above, can undergo similar treatments. Reagents can alternatively be dried by evaporation (FIG. 16) or by vapor deposition. For example, reagents mixed as above, can be placed in an oven at elevated temperature or left at or below room temperature where moisture can be allowed to escape in vapor form due to differences in relative humidity. Alternatively, the reagents can be placed in a desiccating chamber to remove moisture from reagents. A combination of liquids and solids can be used on the device.

Example 3. A Simple Device for Testing a Single Sample

Overview.

A simple embodiment of the invention in this example has a single imaging well with integral dried reagents (including target-specific selection moieties, target-specific signaling moieties, and dyed cushion); a cap; and features for alignment in an analyzer. This device allows powerful but cost-effective analysis that is useful in scientific, clinical, environmental and manufacturing quality laboratories. Multiple test types are possible by changing the contents of the reagents. In this example, sample is added manually using a pipette. The imaging well is compatible with high resolution imaging techniques.

Methods.

The structure of the device includes modules that have been integrated into a single fabricated component (FIG. 4). The modules that are integrated into the single component include an imaging well, dried reagents, and a cap that is attached by a tether. The cap is sealed by mechanical snapping. The device includes feet for protecting the imaging surface and a lip for device-analyzer alignment and focusing. The device is fabricated out of a single injection molded Zeonor® (Zeonor® 1060R, Zeonex®) plastic component, which has materials characteristics ideal for the fluorescent spectral regime.

The imaging well accepts various a samples which seals inside with a cap. The sample can be diluted or not and requires manual user sample input by pipetting. Sample volumes up to 500 µL can be accepted by this device. The cap, attached to the reagent cup by a living hinge of plastic, is snapped sealed by the user. Closing the cap seals the sample inside.

The device can dynamically interact with an analyzer. Alignment keys are present on the outside of the device for alignment to an analyzer. Feet at the base of device minimize optical surface scratching, dust accumulation, and other surface fouling, as well as provide alignment for image focusing.

On-board reagents are dried at the bottom of the well. They include signaling moieties and magnetic selection moieties specific for TSH, as detailed above. Sample fluid is introduced to the device manually by a user pipetting. The reaction is begun immediately upon introduction of the sample to the reaction vessel.

The device is compatible with magnetic selection and fluorescence-based imaging at the bottom surface. The bottom surface is optically flat and transparent, with a thickness of 1 mm.

Conclusion.

This example shows a simple device embodiment in which necessary modules are integrated into a single unit for fabrication. The imaging well is manufactured as an integrated injection molded part that also includes features, such as alignment keys, that allow for dynamic interaction with an analyzer. Dried reagents that include signaling and selection moieties are lyophilized into the imaging well which is compatible with the characteristic spectral regime and large area imaging.

Variations.

There are many potential variations, including those listed in the detailed description of the device above. Another embodiment of this device can include device-device alignment features that can be used for stacking or joining together of multiple devices for improved transportability. Information management features can be added. Also, the imaging window can be located on a different surface, such as the top or side, which would make other types of specific selection possible. The sample volume of this device can be modified depending on assay requirements by fabricating a well of a different size. The volume of an assay may range from as small as less than 2 µL for a whole blood sample from a fingerstick to as large as greater than 2 mL for a diluted fecal sample. Alignment features, including feet and lip, and the cap presented in this device may or may not be present in alternative embodiments.

Example 4. A Device for Performing Multiple Assays on a Sample

Overview.

One embodiment of the device exemplifies the ability to perform multiple assay tests on a single sample. In this example, a sample is metered by actuation of a screw cap into parallel reaction wells where different tests are run in parallel. The screw cap can interface with an analyzer for precise metering of fluid. This device provides powerful but cost-effective analysis of multiple tests in a single sample, which can include tests such as integrated positive or negative controls. It is useful in scientific, clinical, environmental and manufacturing quality laboratories.

The device requires manual sample input by either user or analyzer, such as by pipetting. The device includes dried reagents in the imaging wells. The sample is distributed precisely to multiple imaging wells through the device-analyzer fluidics interface. Trapped air is vented through a hydrophobic membrane that has been heat welded to the top surface of the device. The hydrophobic membrane also helps ensure proper metering. Assay interfering detritus is removed with the integrated filter. The integrated imaging well is compatible with the characteristic spectral regime as well as high resolution imaging techniques.

Methods. This device (FIG. 7) includes specific instances of modules and parameters of modules described in the detailed description sections above. They are described here to illustrate one possible combination of modules that may be grouped together to create a useful embodiment of the device.

The structure of the device includes modular components such as the cap, base, channels, and optical window (FIG. 7). These are fabricated as individual modules which are bonded together with heat or ultrasonic welding.

The sample input module accepts samples and seals them inside with a cap. The device requires manual sample input, such as pipetting. The sample in this device example is a fecal sample that may be diluted or not, and have a volume up to 1 mL. The integrated screw cap has means for dynamic interaction with an analyzer. The single sample is distributed precisely to multiple reaction vessels through the device-analyzer fluidics interface on the integrated screw cap. The reaction vessels double in function as imaging wells.

On-board reagents are dried by lyophilization into the imaging wells. See Example 2—Lyophilization of Reagents for details. Regents include signaling and selection moieties. Multiple test types are assayed on a single sample in parallel. In this example, there are three assay tests that include an experimental test as well as one positive control and one negative control that measure the presence of *Clostridium difficile*.

The fluidic system integrates a screw cap module that is engaged by an analyzer mechanism, similar to a screw driver, to mobilize and meter the sample fluid. Upon mobilization, the liquid first passes through a filter (Filtrona, #R26785) to remove large scale particulate matter larger than about 100 microns in size. Then fluid is divided equally along plastic channels with equivalent volumes and resistances to flow. The channel geometries are on the order of 1 mm in both cross-sectional dimensions. Channels are sealed by ultrasonic welding of a polystyrene plastic imaging window, with also forms one wall of the channels. Trapped air is vented out through the top of each well through a hydrophobic membrane (such as Pall, Versapor 800R) that has been heat welded to the plastic base material.

The imaging well is compatible with selection and imaging from below with high resolution imaging techniques. The bottom is flat, 1 mm thick polystyrene sheeting that is compatible with the spectral regime of the signaling moiety. Signaling moieties are detected by fluorescence in visible range (450-550 nm). The recessed imaging window protects surface from dust and scratching. Feature geometry ensures positioning and registration in an imaging analyzer.

Conclusion.

This example shows a device embodiment in which multiple assay tests are conducted on a single sample. Features on the device allow interaction with an analyzer, including sample metering and positioning for imaging. Dried signaling and selection moieties are lyophilized into the imaging wells which are also compatible with the characteristic spectral regime and large area imaging.

Variations.

There are many potential variations, including those listed in the detailed description of the device above. Another embodiment of this device includes a frangible seal on the sample inlet reservoir. This allows liquid reagents to be used. Device-device alignment features could be added to provide for stacking or joining together of multiple devices for improved transportability. Also, information management features could be added. The imaging window could be moved a different surface such as the top or side, allowing for other selection types. The device could be fabricated out of different materials and could be bonded together in different ways, such as epoxy or diffusion bonding. Other samples could be used. The sample volumes could be as small as less than 2 µL for a drop of blood, for example, to as large as greater than 2 mL for environmental water testing, for example. Different sized well volumes could be fabricated depending on assay requirements. The sample could be divided into as few as two or as many as more than six equal volume aliquots for parallel assay testing. Alternatively, the sample could be analyzed without sample division, such as in Example 3.

Example 5. A Device with Alignment Features for Stacking and Registration in an Analyzer Overview.

This example illustrates a fully integrated device with alignment features for stacking and registration in an analyzer. The device also has multiple imaging wells and a sample metered by analyzer actuation of a screw cap. This device provides powerful but cost-effective analysis and is useful in scientific, clinical, environmental and manufacturing quality laboratories. Device-device alignment features provide for stacking of multiple devices for improved transportability to an analyzer. After manual sample input and transport to the analyzer, the device allows multiple tests to be run with on-board reagents. Specific device-analyzer alignment features for input to an analyzer ensure proper engagement between the device and an analyzer. The device also interacts with an analyzer through the device-analyzer fluidics interface to precisely distribute and meter the sample into multiple reaction vessels for processing. The imaging well is compatible with high resolution imaging techniques and the spectral regime characteristic to the signaling moiety. Also illustrated by this device example are two information management features, a one-dimensional barcode and a handwritten label.

Methods.

This device (FIG. 8) includes specific modules and parameters of modules described in the detailed description sections above. The device described here serves to illustrate only one possible combination of modules that can create a useful embodiment of the device.

The structure of the device includes modular components such as the reagents, cap, base, channels, and imaging well (FIG. 8). These are fabricated as individual modules which are bonded together with heat or ultrasonic welding. This device also has device-device alignment features for stacking and device-analyzer alignment features for interaction and alignment with an analyzer.

The sample input module accepts a sample and seals it inside with a cap. The device requires manual sample input, such as pipetting, by a user. The sample in this device example is a fecal sample that may be diluted or not, with a volume up to 1 mL. The integrated screw cap interacts dynamically with an analyzer. The single sample is distributed precisely to multiple reaction vessels through the device-analyzer fluidics interface on the integrated screw cap.

On-board reagents are dried by lyophilization into the imaging wells. See Example 2—Lyophilization of Reagents for details. Multiple test types are assayed on a single sample in parallel. In this example, there are three assay tests that include an experimental test as well as one positive control and one negative control that measure the presence of *Clostridium difficile*.

The fluidic system integrates a screw cap module that is engaged by external means of an analyzer to mobilize and meter the sample fluid. Upon mobilization, the liquid passes through a filter (Filtrona, #R26785) to remove large scale particulate matter. Then fluid is divided equally along plastic channels with equivalent volumes and resistances to flow. Trapped air is vented out through the top of the wells through a hydrophobic membrane (Pall Corporation, Versapor® 800R) that has been heat welded to the plastic base material.

The imaging wells are compatible with specific selection and imaging from below with high resolution imaging techniques. Imaging wells are formed by ultrasonic welding of 1 mm thick Zeonor® plastic film (Zeonex®) to the plastic base and are optically flat. Signaling moieties are detected by fluorescence in the visible wavelength range, which are compatible with the spectral regime of the imaging wells. The recessed imaging window protects surface from dust and scratching.

The device has information management features for linking patient information with assay results. There are two types of information management modules in FIG. 8. A one-dimensional barcode, applied during manufacturing, is adhered to the base by pressure sensitive adhesive. There is also a label where sample and patient information can be handwritten by the user.

Conclusion.

This example shows a device embodiment in which multiple assay tests are conducted on a single sample. Features on the device provide for interaction with an analyzer, including sample metering and positioning for imaging. Dried signaling and selection moieties are lyophilized into the imaging wells which are also compatible with the characteristic spectral regime and large area imaging.

Variations.

There are many potential variations, including those listed in the detailed description of the device above. Alternative information management modules could be used such as RF ID or embedded electronics. Other alignment keys could also be envisioned.

Example 6. A Device with Integrated Growth and Reagent Modules

Overview.

This example illustrates a fully integrated device with multiple wells for growth and reaction where a sample is metered by analyzer actuation of a plunger module integrated into the cap. This device provides powerful but cost-effective analysis and is useful in scientific, clinical, environmental and manufacturing quality laboratories. Device-device alignment features provide for stacking of multiple devices for improved transportability to an analyzer. The device allows multiple tests to be run with on-board dried reagents. Specific device-analyzer alignment features ensure proper engagement between the device and analyzer. The device also can interact with an analyzer through the device-analyzer fluidics interface integrated into the cap. Through this module, sample is precisely distributed and metered into multiple growth and imaging wells for processing. The imaging wells are compatible with high resolution imaging techniques and the characteristic spectral regime of the signaling moieties on-board.

Methods.

This device (FIG. 9 and FIG. 10) includes specific instances of modules and parameters of modules described in the detailed description sections above. The example described here illustrates one possible combination of modules that can create useful embodiments of the device.

The structure of the device includes modular components such as the cap and plunger, reagents, base, channels, and integrated imaging and growth wells with a gate. The modules were fabricated as individual modules or were combined, such as with the imaging and growth wells which were injection molded as one piece. The imaging and growth wells were injection molded in Zeonor® 1060R (Zeonex®), an optical grade cycle olefin compatible with the characteristic spectral regime of the signaling moieties on-board. The base was injection molded from K-Resin® K03 (Chevron Phillips Chemical Co. LLC). The plunger was similar in material composition to the rubber plunger tip in a 5 cc syringe plunger, (Becton, Dickenson & Co. Part #9603). The modules were bonded together, as illustrated in FIG. 1, with die cut double sided pressure sensitive adhesive (PSA) coated tape (Adhesives Research, Inc. ARcare® 90445). Plastic films and tapes were cut using a VersaLASER® VL-200 30 mW CO$_2$ laser table. The flow channels were fabricated from the same die-cut PSA coated tape. This device also has device-device alignment features for stacking and device-analyzer alignment features for interaction and alignment with an analyzer.

The sample input module accepts a sample and seals it inside with a cap. The device requires manual sample input, such as pipetting, by the user. The sample in this device example is an eluted nasal swab sample that may have a volume of up to 1 mL. The integrated cap has means for dynamic interaction with an analyzer by a plunger that makes a compression fitting inside the cylindrical shape of the sample input reservoir.

On-board reagents are dried by lyophilization into the growth and imaging wells. See Example 2—Lyophilization of Reagents for details. Multiple test types are assayed on a single sample in parallel. In this example, the growth wells have three different reagents. The sample was inoculated into tryptic soy broth, tryptic soy broth with 6 μg/mL cefoxitin, or tryptic soy broth with ProClin 300™ growth retardant, depending on the growth well. Growth was halted in tryptic soy broth with Proclin 300™. MRSA cells will grow with and without antibiotic, MSSA cells (cefoxitin sensitive) will only grow without antibiotic. Samples containing cells that are not *S. aureus* (e.g. mixed sensitive and resistant cultures) will grow with and without antibiotic, but the assay specificity will not detect non-*S. aureus*. After growth, the three wells are independently tested with identical assay reagents that include signaling and selection moieties to compare rates of bacterial growth under the different growth conditions.

The integrated cap dynamically interacts with an analyzer by a plunger that makes a compression fitting inside the cylindrical shape of the sample input reservoir. Upon mobilization, the liquid passes through a filter (Filtrona, #R26785) to remove large scale particulate matter. Then fluid is divided equally along plastic and PSA tape channels with equivalent volumes and resistances to flow. Next fluid fills the three growth wells, which contain dried reagents as described above. The channel geometries are on the order of 1 mm in width and 0.1 mm in depth and the growth wells have a volume of 150 μL each. Trapped air is vented out through the top of the wells through a hydrophobic membrane (Pall Corporation, Versapor® 200R) that has been heat welded to the top of the growth wells. A gate prevents premature forward flow into the imaging wells, keeping dried reagents in those wells dry while growth occurs. The gate in the example illustrated in FIG. 9 has a cotton plug soaked with silicone oil. The oil prevents forward flow until additional pressure is applied to the device-analyzer fluidics interface after the growth stage has been completed. After growth is completed, the device-analyzer fluidics interface is activated and the sample moves from the growth wells through the gate into the imaging wells where dried assay reagents react with any targets present in the sample. The silicone oil floats to the top of the wells and does not interact with the assay tests. The imaging wells each have a volume of 100 μL. Once again, gas is vented through hydrophobic membranes that seal the tops of the wells and channels.

The imaging wells are compatible with selection and imaging from below. It is also compatible with high resolution imaging techniques when using the spectral regime corresponding to the signal signature of the signaling moieties used. The bottom is optically flat with a 1 mm thickness. Signaling moieties are detected by fluorescence in visible wavelength range. The recessed imaging window protects the surface from dust, scratching, and other fouling. Holes in the base material mask off any extraneous background fluorescence and reflected light to ensure optimal signal detection.

An assay was run in the device and compared to a hand prepared assay, run on the benchtop. The procedure follows. A culture of *S. aureus* (ATCC strain 29213) was grown in growth media TSB (Tryptic Soy Broth, Acumedia cat #7164A) at 32.5° C. for 2 hours to achieve log-phase growth ($OD_{600}$=0.3). The *S. aureus* cells were counted in a hemacytometer on a Zeiss microscope and cells were diluted to 0, 700, 2100, and 8400 cells per every 35 μL solution in fresh TSB for the assay. A reaction mixture containing 100 μL Sybr Green® (Invitrogen cat #S-7563) was diluted 1 part in 2000 parts, 25 μL of 0.005% w/v chicken anti-*S. Aureus* protein A magnetic particles (manufactured as described in Example 1 with the following modification: chicken anti-protein A (Meridian OEM cat #C5B01-296 antibody was used) in 10 mM phosphate, 140 mM sodium chloride, 3 mM potassium chloride (Calbiochem cat #524650), 0.05% w/v Tween 20 (Acros cat #2333600010), 2 mg/mL bovine serum albumin (Sigma-Aldrich cat #A3059), 0.05% w/v ProClin 300 (Supleco cat #48912-U) pH 7.4 and 125 μL of the *S. aureus* dilutions in TSB described was mixed well by pipetting and incubated for 15 minutes at ambient temperature in the dark. After incubation, the reaction mix was spilt into 6 equal portions, 35 μL of reaction mixture was overlaid on 65 μL of dye-cushion solution 15% v/v OptiPrep® (Sigma Cat. No. D1556) and 2 mg/mL Chromotrope 2R (Sigma-Aldrich C3143) pre-aliquoted in 3 wells in a 96-well half-area diameter clear bottom black plate (Grainer, Cat. No. 675096) and in 3 imaging wells of the device. Cell-particle complexes were deposited on the bottom of all wells by magnetic selection. Wells in a 96 well plate were placed on a bar magnet for 4 minutes. The bar magnet used a configuration of 22×22×100 mm permanent magnets depicted in FIG. 20. The plate was then removed from the magnet and placed in a high throughput automated imaging analyzer (FIG. 19). The wells were imaged on the analyzer at a 0.1 second exposure time. Individual fluorescent cells were then enumerated using software as described above. Wells in the device were placed in an alpha analyzer which automatically moves the cartridge to a magnetic selection station and then to the imaging station. The wells were then imaged at a 0.1 second exposure time. Individual fluorescent cells were enumerated using imaging software as described in Example 1.

Results.

FIG. 18A shows the comparison of fluorescent counts in the *S. aureus* assay as run on the high throughput automated imaging analyzer and alpha analyzer. The results are similar within experimental error. FIG. 18B shows a digital image of individual stained *S. aureus* cells without magnification and comparison to a sample without cells. The results demonstrate that reagents in imaging wells of the device analyzed on the analyzer and by hand yield similar results.

Conclusion.

This device embodiment illustrates an integrated device consisting of numerous individual modules. It includes reagents with signaling and selection moieties, large area imaging wells compatible with the spectral regime, and intermediate processing modules for on-board growth. Features on the device provide for interaction with an analyzer, including sample metering and positioning for imaging. One example of manufacturing assembly is also illustrated.

Variations.

There are many potential variations, including those listed in the detailed description of the device above. Another embodiment of this device could include a frangible seals on sample inlet reservoir and wells, which would allow liquid reagents to be contained. Alternatively, these frangible seals could be used as gates, keeping dry reagents dry until appropriate for the assay. Information management features could be added, such as a barcode, which would allow information tracking. The imaging window could be moved a different surface such as the top or side, allowing for other selection types. The device could be fabricated out of different materials and could be bonded together in a different ways such as heat or sonic welding. The sample volume could be varied so that it may be as small as less than 2 μL or as large as greater than 2 mL. Different sized well and channel volumes could be fabricated depending on assay requirements. The sample could be divided into as few as two or as many as more than six equal volume aliquots for parallel assay testing. Alternatively, the sample could be analyzed without any sample division. Alternative intermediate modules could be used in place of the growth modules, for assays that may require different pre-assay sample treatments.

Example 7. A Device that Accepts Sample Swabs

Overview.

This device embodiment consists of parallel growth and imaging wells with dried reagents where sample swabs are directly inserted. Cap closure bathes the sample swabs with buffer. Fluid is mobilized by a syringe-like plunger that is not integrated into the cap. Also detailed in the example is one example of the device work flow as it may be used in the application of MRSA sample testing, where one or more devices may interact with an analyzer.

Methods.

The device illustrated in FIG. 11 and FIG. 12 includes specific instances of modules and parameters of modules described in the detailed description sections above. The example modules described here illustrate only one possible combination that can create a useful embodiment of the device.

The structure of the device (FIG. 12) includes modular components such as the cap, base, channels, reagents, and integrated imaging and growth wells. These modules are fabricated as individual components that are inserted into a plastic base that utilizes elastomeric plastic (thermoplastic polyurethane) living hinges for easy manufacturing assembly. Some modules are combined during fabrication, such as the imaging and growth wells, which are injection molded in one piece, as described above. The flow channels are fabricated as part of the base plastic material and are sealed during closure of living hinges during manufacturing assembly. This device also has device-device alignment features for stacking and device-analyzer alignment features for interaction and alignment with an analyzer, which can be seen in FIG. 11.6.

The sample input module accepts either one or two sample collection nasal swabs (FIG. 11.4) and seals them inside with a cap. The sample input module consists of sample input reservoirs that conform to the shape of the sample collection swabs, minimizing elution volume required (FIG. 12). The sample collection swab handles are cleaved off during cap closure (FIG. 11.5). Upon closure, the cap snaps closed with an audible clicking sound that communicates to the user that the samples are securely sealed inside the device. Cap closure also causes the swabs to be bathed with buffer. This occurs when tabs on the cap (FIG. 12) compress a blister pouch filled with buffer, opening a frangible seal. Once the frangible seal is opened, the buffer flows into the sample input reservoir where it bathes the swabs, keeping bacteria cells in the sample viable until the assay is run.

On-board reagents are dried by lyophilization into the growth and imaging wells. See Example 2—Lyophilization of Reagents for details. Multiple test types are assayed on a single sample in parallel. In this example, the growth wells have three different reagents. One growth well has antibiotic, another has growth media without antibiotic, and the last has neither media nor antibiotic. After growth, the three wells are independently tested with identical assay reagents, which include signaling and selection moieties, to compare rates of bacterial growth. There is also a liquid buffer contained in a blister pouch. This liquid first bathes the sample collection swabs, then elutes the bacterial sample from the swabs, and then is used to chase the sample through the device, mobilizing the sample.

Features for dynamic interaction with an analyzer is not integrated into the cap, but are accessed by a hole in the top of the device (FIG. 12). A linear actuator on the analyzer interacts with this interface to compress a blister pouch which mobilizes fluids in the device. Upon mobilization by the analyzer, the liquid is divided equally along plastic channels with equivalent volumes and resistances to flow. The liquid then fills three growth wells containing dried reagents described above. A gate prevents premature forward flow into the imaging and reaction wells, and keeps dried reagents in those wells dry while growth occurs. The gate illustrated in FIG. 12 has a frangible seal between each well. The frangible seal prevents forward flow until additional pressure is applied to the device-analyzer fluidics interface after the growth stage has been completed. After growth is completed, the device-analyzer fluidics interface is activated, and the sample moves from the growth wells through the gate into the imaging wells where dried assay reagents react and form labeled moieties with target bacterial cells in the sample.

The imaging wells are compatible with selection and imaging from below. It is also compatible with high resolution imaging techniques in the spectral regime characteristic for the signaling moiety. The recessed imaging window protects surface from dust and scratching. Holes in the base material mask off any extraneous background fluorescence and reflected light to ensure optimal signal detection.

Information management modules are added by the user (FIG. 11.2), by application of a barcode. One example of external packaging of the device in shown in FIG. 11.1, where a device kit includes the device and two swabs for nasal sample collection. The package is manufactured in sterile conditions, and includes a desiccant to maintain low humidity inside the package until use.

One general concept for MRSA test work flow using the device is illustrated in FIG. 11. In this example, the user applies a hospital barcode label to a device, inserts the sample into the device, and inserts the device into an analyzer. This involves six discrete user steps. After opening the package (FIG. 11.1) the user applies a barcode (FIG. 11.2). Then the user obtains a sample (FIG. 11.3) and inserts the swab into the device (FIG. 11.4). The ends of the swab are broken off upon closure of the cap (FIG. 11.5), and the device is placed in an analyzer (FIG. 11.6). All other steps, including hospital specific data reporting, occur automatically.

Conclusion.

This shows one device embodiment with integrated modules where a sample collection module can be accepted directly into the device. This device includes reagents with signaling and selection moieties, large area imaging wells compatible with the spectral regime, and features that allow interaction with an analyzer. The work flow is one example that may also occur in different ways and may depend on assay, venue, user, and throughput of samples.

Variations.

There are many potential variations of this device, including those listed in the detailed description of the device above. One embodiment of this device could include a roller as illustrated in FIG. 2 that acts on one or more blisters to mobilize fluids. Activation of the roller could apply pressure a liquid in a deformable chamber, causing one or more frangible seals to rupture. The sample could be divided into as few as two or as many as more than six equal volume aliquots for parallel assay testing. Alternatively, the sample could be analyzed without any sample division or the volumes of the different aliquots could vary. Alternative intermediate modules could be used in place of the growth modules, for assays that may require different pre-assay sample treatments. The work flow could be modified for acceptance of other sample collection devices, such as blood collection where a patient sample is collected from a fingerstick. The device could include an integrated module for a sterile fingerstick, such as a lancet or capillary tube. The work flow in such a case might then be, user opens package, sterilizes the patient finger, engages lancet, blood drawn into a sample collection device such as a capillary tube. The sample collection module would then insert into the device, the patient wound would be bandaged, and then one or more devices would be inserted into an analyzer for assay results determination. Other work flows can be envisioned. Alternative sample types and consistency accepted by the device could include blood, fecal, or environmental samples, to name a few. The device could be modified to accept other sample collection modules, such as a capillary tube of mucous, a syringe of blood, or a pipette bulb with a diluted environmental sample to give a few examples.

Example 8. A Device that Autonomously Processes a Single Sample

Overview.

A device can autonomously accept a single sample through capillary flow and also automatically meter the sample into one or more test wells for processing. The example illustrated in FIG. 5 autonomously takes in, meters, and initiates a reaction with a sample without any further interaction from a user or analyzer. The sample is simply brought in contact with the device, and after a specific period of time, the device is interrogated by an imaging technique.

Methods.

This device (FIG. 5) includes specific instances of modules and parameters of modules described in the detailed description sections above. The modules described here illustrate only one possible combination of modules that can create a useful embodiment of the device.

The structure of the device (FIG. 5C) integrates sample inlet, fluid flow channels, reaction and imaging wells, and venting into a single fabricated component. Some of the modules illustrated are fabricated by rapid prototyping techniques. Parts illustrated in FIG. 5C and FIG. 5D were fabricated using a Polyjet 3D printer, where FIG. 5B utilized a stereo lithographic apparatus (SLA). The benefit of such rapid prototyping techniques is rapid functional testing on various modules geometries such as pictured in FIG. 5D.

The sample input module accepts a sample by capillary action. The device requires a sample come in contact with the sample inlet port, at which point the device automatically draws in the correct volume of sample by differences in surface tension. Changes in geometries and surface treatments change flow rates and even gate flows from continuing in a specific direction. The sample in this device example is whole blood from a finger stick where the initial sample volumes were approximately 10 µL. The devices may or may not have anticoagulant dried down in the channels or wells to effect blood clotting.

On-board reagents are dried by lyophilization into the test wells. See Example 2—Lyophilization of Reagents for details. Multiple tests were assayed on a single sample in parallel. In FIG. 5C for example, six parallel tests were run per sample per assay. In this case, two different sample proteins were assayed against two positive controls and two negative controls.

Sample liquid mobilization occurred automatically in this device. The liquid flow moved through capillary channels and into the test wells, which doubled as imaging wells. The sample was metered automatically by controlling the geometries and surface properties of the materials used to manufacture the device. Channels and wells had equivalent volumes and resistances to flow, which resulted in equivalent filling volumes. Air or trapped gasses were displaced by the sample flow and exit from a capillary vent. The flow channels and wells were sealed by a PSA tape (see above) to both the top and bottom surfaces of the integrated base. Physical features on the device allowed for registration on an imaging analyzer.

The device is compatible with selection and imaging from below or above, but the example illustrated used magnetic selection moieties that necessitated capture at the bottom. The imaging wells were compatible with the fluorescent signaling moiety's spectral regime as well as high resolution imaging techniques.

The device could be packaged in external packaging that include FIG. 15, where multiple devices are included in each package. The external packaging can be stackable and be used as a means to transport multiple devices. The external packaging contains alignment features allowing for devices to be imaged by an analyzer.

Results.

An assay, as described in Example 2 above, used dried reagents lyophilized into spheres (FIG. 5E) to identify target moieties using fluorescence imaging. An image is illustrated in FIG. 5F in which the capture moieties include bound TSH proteins.

Conclusion.

This example shows a device embodiment where all assay steps occur autonomously on-board a device without interaction with a user or an analyzer. The device includes reagents with signaling and selection moieties, large area imaging wells compatible with the spectral regime, and features that provide for interaction with an analyzer.

Variations.

There are many potential variations of this device, including those listed in the detailed description of the device above. The device could include various numbers of reaction or test wells, from one to more than six. The device could accept samples of various types and consistency, from a diluted fecal sample to an eluted nasal swab. The volumes of test wells could vary to include from less than 1 µL, in the case of a droplet of blood from a fingerstick, to more than 1 mL, in the case of a urine sample.

Example 9. A Device that Autonomously Processes a Single Sample Comprising an Integrated Sample Collection Function Overview.

This device embodiment illustrates one way in which a sample collection module can be integrated into the device. Integrating the sample collection module into the device may protect the user from biohazardous components such as sharps, in the case of a lancet for drawing blood. Integrating a sample collection module into the device may simplify the sample assay process for users by removing steps and additional packaging inserts.

Methods.

A sample collection module was integrated into a device that contains all the features and functions described in Example 8. FIG. 5A and FIG. 5B show a device that has an integrated lancet for blood sample collection. The lancet is activated by an integrated button that is built into the base module. After the lancet has been deployed, it automatically retracts into the device by means of a spring mechanism. Once it has been deployed, it does not redeploy. This ensures that the user is protected from the sharp material.

FIG. 6 illustrates a similar concept, where a that cap contains the lancet also includes a sterile alcohol pad. The alcohol pad is included so that the user can disinfect a fingerstick location before the blood sample is collected. Both of these integrated sample collection functions are built into devices similar to the one described in Example 8. The device also includes an integrated information management module, such as a patient identification bracelet (FIG. 6).

Conclusion.

This example shows a device embodiment where a sample collection module is integrated into the device. Integrating the sample collection module into the device may protect the user from biohazardous components, as well as sharp materials, such as a lancet. Integrating the sample collection module into the device may simplify the sample assay process for the user by removing steps and minimizing additional kit or packaging inserts.

Variations.

There are many potential variations of this device, including those listed in the detailed description of the device above. The device could include various numbers of integrated sample collection modules or combinations of sample collection modules, such as capillary tubes or syringes or disposable pipette tips, to name a few. The volumes and types of samples collected could range from whole blood, as described here, to diluted fecal or nasal samples.

The device can be packaged into external packaging (FIG. 14) where one or more devices are included in each package. The external packaging may join together in a modular fashion and may be used as a means to transport multiple devices, or even provide engagement or alignment features for an analyzer to interact with the device.

Example 10. Device with Multiple Reagent Wells

Overview.

This device embodiment (FIG. 13) integrates one or more wells that are fluidically non-contiguous, where fluids are mobilized by the device-analyzer fluidics interface that is a pipette tip. One sample is distributed precisely to sequential processing and imaging wells by a pipette tip. This device does not have flow channels. Liquids are mobilized from one location to another inside the device-analyzer fluidics interface. This is an advantage that can minimize or eliminate cross contamination or backflow between wells.

Methods.

The structure of the device (FIG. 13) includes one or more wells that are physically, but not fluidically connected. Not fluidically connected means that a liquid placed into one well does not engage with other wells or liquids unless it is mobilized by the device-analyzer fluidics interface and physically carried from one location to another. In this example, the device-analyzer fluidics interface is a pipette tip (FIG. 13). Pipette tips are disposed of after each liquid handling step, each assay.

The sample is input into a sample input reservoir manually by a user. The sample is transported to an intermediate processing module where it is mixed with dried signaling moieties in a well. After reacting with signaling moieties, the sample is transported to a different intermediate processing well where it is mixed with magnetic selection moieties. After the sample has reacted with selection moieties, the sample is transferred to an imaging well that is compatible with both selection and imaging by an analyzer. The imaging well complements the characteristic spectral regime of the signaling moieties and is compatible with specific selection. Features for positioning and registration allow selection and imaging by an analyzer.

Conclusion.

This device example shows an example of one or more wells that are fluidically isolated from one another. Liquid is mobilized by a pipette tip which may limit carryover and cross contamination. The device also includes on-board reagents, such as signaling and selection moieties, an imaging well, and registration features compatible with large area imaging by an analyzer.

Variations.

There are many potential variations of this device, including those listed in the detailed description of the device above. One or more reagents or modules could be combined, or more than one parallel test could be assayed. The device may or may not include one or more pipette tips on-board. It may allow for acceptance of pipette tips from an analyzer. One or more of the pipette tips could be disposable or recycled, and they could be integrated into the device or supplied externally by an analyzer. Pipette tips could be recycled after a thorough cleaning step or they could be disposed of after each liquid transfer step. Liquid mobilization may be done with alternative means than a pipette tip, such as a capillary tube or an absorbent pad that is compressed to release a liquid. It could also be manufactured from low cost modules compatible with blow molding, for example.

The sample could be input into a sample input reservoir manually by an analyzer. Zero, one, or more intermediate processing steps can occur in intermediate processing modules. For example, one intermediate module might be used for growth, another for rehydrating cushion, and another for rehydrating dye. Some embodiments may not have any intermediate processing modules.

Example 11. Device that Captures Target in a Pipette Tip

Overview. A device embodiment could integrate a disposable pipette tip with non-contiguous processing wells where the reaction occurs in the pipette tip. This device embodiment is similar to Example 10 (FIG. 13), except that the reaction occurs in the pipette tip.

Methods.

Structural similar to the device illustrated in FIG. 13, one embodiment of the invention exists where the reaction occurs in a pipette tip. Capture molecules are bound to the inner surfaces of a pipette tip, that bind to targets that may be present in a sample when sample is introduced. The pipette tip aspirates the sample. Target, if present in the sample, reacts and binds to the capture molecules on the pipette inner surface, where they are temporarily immobilized. The unbound sample is discarded and is followed by one wash step to dilute and remove unbound sample that may remain in the pipette tip. Next, signaling moieties are introduced which also bind to the temporarily immobilized target, if present. The unreacted signal moieties are discarded and are followed by one wash step to dilute and remove unreacted signal moieties that may remain in the pipette tip. Next, selection moieties are introduced which also bind to the temporarily immobilized target, if present. The unreacted selection moieties are discarded and are followed by one wash step to dilute and remove unreacted signaling moieties that may remain in the pipette tip. Finally, a releasing agent is introduced into the pipette tip which causes the target, if present, to be mobilized in liquid. The liquid with mobilized target bound to both signaling and selection moieties, if present, is dispensed into an imaging well. The sample is then specifically selected for and analyzed by imaging. Device structural details are explained in Example 10.

Conclusion.

This device builds on Example 10 to illustrate one method in which a sample undergoes a number of sequential processing steps inside a pipette tip. The device also includes on-board signaling and selection moieties, intermediate processing reagents, an imaging well, and registration features compatible with large area imaging by an analyzer.

Variations.

There are many potential variations of this device, including those listed in the detailed description of the device above. One or more reagents or modules could be combined, or more than one parallel test could be assayed. The device may or may not include one or more pipette tips on-board. It may allow for acceptance of pipette tips from an analyzer. One or more of the pipette tips could be disposable or recycled, and they could be integrated into the device or supplied externally by an analyzer. Pipette tips could be recycled after a thorough cleaning step or they could be disposed of after each liquid transfer step. Liquid mobilization may be done with alternative means than a pipette tip, such as a capillary tube or an absorbent pad that is compressed to release a liquid. It could also be manufactured from low cost modules compatible with blow molding, for example.

The sample could be input into a sample input reservoir manually by an analyzer. Zero, one, or more intermediate processing steps can occur in intermediate processing modules. For example, one intermediate module might be used for growth, another for rehydrating cushion, and another for rehydrating dye. Some embodiments may not have any intermediate processing modules. More than one or zero washings may occur at any given step above. The capturing moiety may double as either the signaling or selection moiety.

Example 12. Method for an Assay Using a Dye Cushion

Overview.

This example demonstrates how the dye cushion eliminates background signal from free signaling moieties. This aspect of the invention allows sensitive imaging of labeled targets without requiring wash steps.

Method.

A reaction of 10 µL of a 0.007% w/v dilution of anti-hTSH antibody labeled fluorescent particles and 10 µL of a 0.05% w/v dilution of anti-hTSH antibody labeled magnetic particles were mixed with 10 µL 200 mM EPPS (Sigma-Aldrich cat #E9502) buffer, 400 mM 1,3 diaminopropane (Sigma-Aldrich cat #D230807) pH 7.8, 10 µL of 1 mg/mL Alginic acid (Sigma-Aldrich cat #A2158), 2.5% w/v polyvinylpyrrolidone (Sigma-Aldrich cat #PVP40), 0.5 mg/mL bovine gamma globulin (Lampire Laboratories cat #7400805), 1 mg/mL mouse gamma globulin (Jackson Imunno Cat #015-000-002) in 10 mM phosphate, 140 mM sodium chloride, 3 mM potassium chloride (Calbiochem cat #524650) pH 7.4 and 10 µLµL of plasma sample was formed, mixed, and incubated for 10 minutes. In another well, 90 µL of cushion dye reagent 2 mg/mL Chromotrope R2 (Sigma-Aldrich cat #C3143) and 25% v/v Optiprep® (a 60% w/v solution of iodixanol) (Sigma-Aldrich D1556) in 20 mM Tris (JT Baker cat #4109-02), 0.05% w/v Tween 20 (Acros cat #2333600010), 2 mg/mL Bovine serum albumin (Sigma-Aldrich cat #A3059), 0.05% w/v ProClin 300 (Supleco cat #48912-U) was added. At the end of the incubation a 40 µL aliquot of reaction mixture was layered on top of the dye cushion layer and another was placed in a well without a dye cushion layer. The wells were then placed on a bar magnet and the immunocomplexes selected magnetically for 5 minutes and deposited on the bottom of the well. The bar magnet used a configuration of 22×22×100 mm permanent magnets depicted in FIG. 20. The well was then placed in a high throughput analysis automated analyzer (FIG. 19). The wells were then imaged on the analyzer at a 0.1 second exposure time. Individual fluorescent particles were enumerated using software developed at First Light Bioscience.

Results.

FIG. 21 shows the presence of dye in the dye-cushion reagent completely shields the signaling moieties lying above the dye cushion layer.

Conclusions.

The example demonstrates that dye-cushion can dramatically reduce the background from free signaling moieties and non target-signaling moiety complexes. The dye cushion separates these entities from selected target signaling moiety complexes deposited in the detection zone. This example demonstrates an embodiment of the invention which uses a dye-cushion reagent and allows the detection of targets by non-magnified imaging without washing.

Variations.

Alternative embodiments can also incorporate other density agents, including other commonly used density agents such as iodixanol, sodium diatrizaote, sodium, metrizaoate, metrizamide, sucrose, and other sugars, oligosaccharides, synthetic polymers (e.g. Ficoll), and various salts such as cesium chloride, potassium bromide, and others. Alternative embodiments can use other dyes can be used to match the different signaling character and moieties in use. For example the dye Toluidine Blue O could be used with the fluorescent label Texas Red (sulforhodamine).

In these other embodiments different signal characters can be used e.g. fluorescence, chemiluminescence, light absorbing, light scattering, phosphorescence, enzymatic reactivity and Raman scattering. Furthermore these embodiments could use different signaling moieties, e.g. fluorescein diacetate (fluorescent esterase substrate), Sybr Green® (fluorescent DNA stain), Sudan black (lipid staining), enzyme substrates that yield insoluble products, polystyrene particles, polystyrene particles containing fluorescent dyes, colloidal gold and others.

Different category labeling moieties can be used include but are not limited to: Antibodies (including various Immunoglobin types) and other proteins (e.g. lectins, hormone receptors and others), Oligonucleotides and their synthetic analogs (e.g. peptide nucleic acids, aptamers and others), Oligosaccharides (e.g. heparin and others), Organic polymers (e.g. dextran sulfate and others) and Small molecules (e.g. drugs, non-peptide hormones, biotin, dyes and others)

The selection may be specific through selection of a specific target within a category (e.g. selection of human thyroid stimulating hormone from blood or S. aureus cells from nasal samples). The assay may be also specific through selection of a labeled category of targets (e.g. selection of lipoproteins from human plasma). The method described can be used in the selection of targets which can include, but are not limited to cells, viruses, organelles, lipoproteins, and molecules including proteins, oligonucleotides, lipids, oligosaccharides, and small organic and inorganic molecules.

Example 13. Method for Lyophilizing Reagents for Detection of S. Aureus Bacterial Cells in Layers Overview.

Drying reagents within the device can increase stability while maintaining functionality, ultimately improving the shelf-life of the device. A longer shelf-life device can decrease costs to the user by ensuring devices will yield accurate results over longer periods of time. This example demonstrates how reagents can be lyophilized in layers.

Methods.

A similar method to those detailed in Example 2 can be used for stabilizing reagents. Reagents were lyophilized together in layers. In this example, reagents for the detection of S. Aureus bacterial cells are lyophilized in layers. A Dura-Stop lyophilizer was pre-cooled to −45° C. A 65 µL aliquot of dye-cushion reagent: 2 mg/mL Chromotrope R2 (Sigma-Aldrich cat #C3143) and 10% v/v Optiprep® (a 60% w/v solution of iodixanol) (Sigma-Aldrich D1556) 5% w/v trehalose (Sigma-Aldrich cat #T9449) was pipetted into assay wells. The plate was placed in the lyophilizer and the reagent layer allowed to freeze for 1 hour. The assay wells were removed from the lyophilizer and 25 µL of a reagent that contained Sybr Green® (Invitrogen cat #S-7563) diluted 1 part in 2000 parts, 0.005% w/v chicken anti-S. Aureus protein A magnetic particles (manufactured as described in Example 1 with the following modification: chicken anti-protein A (Meridian OEM cat #C5B01-296 antibody was used) in 10 mM phosphate, 140 mM sodium chloride, 3 mM potassium chloride (Calbiochem cat #524650), 0.05% w/v Tween 20 (Acros cat #2333600010), 2 mg/mL bovine serum albumin (Sigma-Aldrich cat #A3059), 0.05% w/v ProClin 300 (Supleco cat #48912-U) pH 7.4 was carefully pipetted on top of the frozen dye cushion reagent. The assay wells were immediately returned to the lyophilizer and frozen for 1 hour. The vacuum was applied, and the wells were lyophilized at −45° C. for 16 hours. Then the temperature was set to −5° C. for 6 hours, followed by 25° C. for 2 hours. Upon completion, the lyophilizer was turned off, and the vacuum was released. The wells were removed and covered with PCR film and stored in a desiccator until use.

Assay Comparing Dried S. Aureus Reagents with Liquid Reagent for the Detection of S. Aureus bacterial cells.

A culture of S. aureus (ATCC strain 29213) was grown in growth media TSB (Tryptic Soy Broth, Acumedia cat #7164A) at 32.5° C. for 2 hours to achieve log-phase growth ($OD_{600}$=0.3). The S. aureus cells were counted in a counting chamber on a Zeiss microscope and cells were diluted to $2\times10^5$ cells/mL in fresh TSB. The reaction occurred in a 96 well polycarbonate PCR plate (Fisher Scientific, Cat. No. 14230237). The reaction mixture (50 µL) contained 25 µL S. aureus cells (5,000 cells) in PBS-TBP or just PBS-TBP (no cells), 20 µL of Sybr Green® 1 dye (diluted 1:2000× in saline) and 5 µL of anti-protein A coated magnetic particles ($2\times10^{10}$ particles/mL) suspended into PBS-TBP solution (10 mM phosphate, 140 mM sodium chloride, 3 mM potassium chloride (Calbiochem cat #524650), 0.05% w/v Tween 20 (Acros cat #2333600010), 2 mg/mL bovine serum albumin (Sigma-Aldrich), 0.05% w/v ProClin 300 (Supleco) adjusted to pH 7.4. The assay reaction was mixed by pipetting and incubated for 15 minutes at ambient temperature in the dark. After incubation, 40 µL of reaction mixture was overlaid on 70 µL of cushion solution (consisted of 15% OptiPrep® Sigma Cat. No. D1556) and 5 mg/mL Chromotrope 2R (Sigma-Aldrich C3143) pre-aliquoted in 96-well half-area diameter clear bottom black plate (Grainer, Cat. No. 675096). During incubation a solution of S. aureus cells (5,000 cells) in 120 µL of a 1:1 mixture of TSB/PBS-TBP or just PBS-TBP (no cells) was added on top of specific wells with lyophilized reagents. In order to select cell-particles complexes at the bottom of the well, the plate was then subjected to magnetic selection by placing it on a bar magnet for 4 minutes. The bar magnet used a configuration of 22×22×100 mm permanent magnets depicted in FIG. 20. The plate was then removed from the magnet and placed in an imaging analyzer. The wells were imaged as described above at a 0.1 second exposure time. Individual fluorescent cells were enumerated using imaging software as described in Example 1.

Results.

Lyophilized S. Aureus reagents were shown to demonstrate equivalent performance between liquid and dried reagents (FIG. 3). FIG. 3A shows data comparing fluorescent objects (Multipath count) for samples with and without S. Aureus cells analyzed per the assay. FIG. 3B shows actual images from samples with and without S. Aureus cells using the assay using lyophilized S. Aureus reagents.

Conclusions.

The results demonstrate that reagents lyophilized together in layers can perform as well as liquid reagents.

Variations.

There are other alternative embodiments of this example. Lyophilization conditions, such as temperatures and times can be adjusted, and various reagents, in addition to those listed above, can undergo similar treatments. Reagents can alternatively be dried by evaporation (FIG. 16) or by vapor deposition. For example, reagents mixed as above, can be placed in an oven at elevated temperature or left at or below room temperature where moisture can be allowed to escape in vapor form due to differences in relative humidity. Alternatively, the reagents can be placed in a desiccating chamber to remove moisture from reagents. A combination of liquids and solids can be used on the device.

Example 14. An Automated Analyzer for Device Processing

Overview.

This example describes a device (FIG. 9) that interacts with an automated analyzer (FIG. 25) to process an assay and image targets, if present, in a sample. The device accepts a sample and interface with the analyzer for processing. The analyzer incorporates a CMOS camera for imaging targets, software for imaging, and hardware for device conveyance. The analyzer can interact with the device to initiate liquid handling. The analyzer also provides incubation, focusing, image analysis, and results reporting. The analyzer has a throughput of up to 40 samples per hour and can be used for high volume clinical laboratory testing applications. It could also be used in food processing and veterinary testing applications.

Method.

The device was prepared by pipetting an eluted nasal swab sample into the sample input reservoir (FIG. 9). The cap was then closed, and the device was inserted into the analyzer input conveyer queue as a single device for automatic processing. When the device was placed in the queue conveyer (FIG. 24), a sensor was tripped which signaled the analyzer to move the device into the analyzer by a conveyor belt. The belt moved the stack to the position where the device was picked up for processing by the analyzer.

A gantry robot system moved the device from the conveyor belt and then through the stations required for processing. These stations included barcode reading, initiation of growth, fixed temperature incubation, initiation of assay reaction, reaction incubation at ambient temperature, magnetic selection, and imaging of the magnetically selected reaction. Once the analyzer finished analyzing the sample, results were saved to the computer. The device was then automatically disposed of in the integrated biohazard waste device. The processing of the device is explained in detail in the sections below.

The analyzer was designed and built with two queues which can accept stacks with varying numbers of devices (FIGS. 24, 25, 11). The queue was designed to accept a stack of between one and eight devices. When a stack is placed at either input queue opening, a photoelectric sensor (Omron photoelectric retro-reflective sensor E3T-SR21) is triggered and signals the control software to activate a stepper motor (Arcus DMAX-KDRV-23) to move the stack into the analyzer for processing.

When the device was ready to be processed in either queue, the analyzer processed the device. The top of the device was found with a photoelectric sensor (Omron photoelectric retro-reflective sensor E3T-SR21) mounted to the gantry robot (FIG. 24). The robot scanned each queue with the sensor starting at the maximum stack height and moved down until a device triggered the sensor. Once found, the gantry robot removed the device.

Movement of the device in the system was accomplished by three motor systems (FIGS. 24 and 25). These systems were called the input system, the main gantry system, and the imager gantry system. Each system is described below. The systems were capable of operating independently, and occasionally required synchronization for specific operations.

The input system included a single conveyor belt powered by a stepper motor (Arcus DMAX-KDRV-23) as mentioned above (FIGS. 24 and 25). This system was used to move stacks in both queues, thus when either side activated the system, both sides were affected. The belt moved the device from the initial entry point to the space designated for gantry robot pickup. When a device was already in the pickup position, the new device moved with the belt until it contacted the device ahead of it. At that point, the belt slid under the devices that were queued for the pickup position.

Three stepper motors (Arcus DMAX-KDRV-17) were present in the gantry system (FIG. 24). Each motor was connected to linear stage (Automation Solutions, DL20DW-XZ) of a different length. The system was assembled such that the longest stage controlled the gantry Y (left and right) directions. This stage was anchored to the base plate. Attached to Y stage platform was the shortest stage which controlled the gantry X (forward and backward) directions. Attached to the X stage platform was the middle stage. This stage was used to control the gantry Z (top and bottom) directions. Attached to the Z stage was a pair of forks. These forks contained features that mate with features (FIG. 9) molded in the device attached to its platform. Also attached to the Z stage platform was the photoelectric sensor (Omron photoelectric retro-reflective sensor E3T-SR21). The sensor was used to measure the stack height, as mentioned previously.

The gantry picked up the device by positioning the forks by adjusting the X and Z stages. Once the device was held by the forks, the X stage would move to the rear most position to allow the Y stage room to move the device to any station for processing without colliding with structures in the analyzer.

The imager gantry system consisted of two stepper motors (Arcus DMAX-KDRV-17) attached to two linear stages (Automation Solutions, DL20DW-XZ). The longer stage was called the imager X stage. This stage controlled the forward and backward motions of the imager gantry. Attached to the imager X stage was the imager Z stage. This stage controlled the imager gantry's top to bottom motion. Attached to the Z stage was a platform. This platform had features on its surface that mated to the features on the bottom of the device (FIG. 9).

The mechanical resolution of the imager Z stage, determined by a fine pitched screw mechanism, is 5 microns and is greater the mechanical resolution obtained with the other motor systems. This difference was required for fine focus adjustment as well as fine control of height for initiating the reaction assay. These features are discussed in detail below.

After the device was picked up from the input position by the main gantry robot, it was taken to a barcode reader (Microscan MS1). The 1D barcode on the device encoded information including lot number, test type, and test parameters. When read, the control program stored the information in a data structure for tracking the device and holding the analysis results.

Two types of incubation occurred in this analyzer. The first was fixed temperature incubation at 35° C. to allow for growth of bacteria in the sample. The second type of incubation was ambient temperature incubation for the assay reaction. After the device barcode was scanned, the initiation of the sample into the growth wells occurred. The main gantry robot moved the device to the imager gantry platform (FIG. 24). After the gantry dropped the device onto the platform, the imager gantry interacted with the device by raising the imaging platform until the plunger cap on the device (FIG. 9) was pressed into the device by a feature at the top of the imager Z stage. By pressing down on the plunger, the liquid sample was forced to move from the sample input reservoir to the growth chambers where growth reagents were lyophilized. Next, the device was placed in the on-board fixed temperature incubator by the main gantry robot (FIG. 24). The devices were incubated at 35° C. for four hours to allow for sample growth.

The incubator had a shelf constructed of machined parts (top, bottom, left, right, back, and front sides). The shelf bottom contained features that mated with the feature on the bottom of the device (FIG. 9). The incubator walls were constructed using insulation foam which divided the incubator into four chambers. The rear wall of the incubator was shaped to fit four machined doors in front of the four chambers. The doors were opened and closed using actuators (Firgelli L12-50-100-12-I). Heating of the incubator used heating strips (OMEGA, SRFG-310/10-P) across the outside top and bottom of the incubator. These heating strips, as well as any exposed outside surface, were then covered in insulation foam with the exception of the rear wall and doors.

Initiation of the assay occurred after the growth incubation was completed. The main gantry robot removed the device from the growth incubator and moved it to the imager gantry platform (FIG. 24). After the gantry dropped the device onto the platform, the imager gantry initiated the assay by moving the platform away from anything that might collide with the platform. Once cleared, the imager platform was raised until the plunger cap on the device (FIG. 9) was pressed into the device by a feature at the top of the imager Z stage. By pressing down on the plunger, the liquid sample was forced to move from the growth chambers into the imaging chambers where the assay reagents were lyophilized. As the liquid entered the imaging chamber, the reagents were rehydrated, and the assay reaction began. The imager gantry returned to the pickup position and the main gantry robot moved the device to the reaction incubation station. This incubation lasted fifteen minutes and occurred at room temperature.

The reaction incubator consisted of a system of fifteen shelves. The individual shelves had a feature on the surface that mated with the feature on the bottom of the device.

After the reaction was complete, selection of the targets occurred by magnetic selection. When reaction incubation was completed, the main gantry robot moved the device from the shelf to the one of the two identical nests in the magnet station (FIGS. 20, 24, and 25). Magnetic selection was performed for five minutes before the main gantry moved the device to the imaging platform. As shown in FIG. 24, the magnetic capture station consisted of two identical magnet assemblies; each has a nest that accepts a device. The assemblies contained rare earth, solid state type magnets (neodymium-iron-boron N50 NdFeB, 22×22×100 mm bars) as shown on the FIG. 20. This allowed for magnetic selection to occur for two devices during overlapping time periods.

After magnetic selection, imaging was performed. The imaging subsystem (FIG. 23) was designed to work with fluorescent signaling moieties that were excited with blue light. The optics had an LED and an optical filter with a band pass centered at a 475 nanometer wavelength and an emission filter with a band pass centered at a 535 nanometer wavelength. The illumination components, detection optics, and camera were all positioned under the device in the imaging assembly (FIG. 15).

After magnetic capture was complete, the main gantry robot moved the device from the magnet station to the imager gantry robot (FIG. 24). The imager gantry robot moved the device over a distance sensor (Keyence LK-G37). The distance to each imaging well was measured and the focus distance was calculated. The imager gantry robot then moved to the CMOS camera (Mightex BCN-B013) which acquired an 8 bit grayscale image of each well. Each well was imaged ten times and summed to result in a higher bit grayscale image for analysis.

Image analysis occurred using software described in Example 1. Once the analysis was completed, the imager gantry robot moved the device to the ejection system. The device was then pushed off the platform and into the biohazard waste container (FIG. 25). Once the data was analyzed, the results, along with the cartridge information, were stored on a computer, printed (Seiko, DPU-30) and displayed on the LCD touchscreen monitor (AEI, ALCDP7WVGATS) (FIG. 25).

The system was designed to be controlled by a single small board computer (Ampro, RB800R) running Ubuntu Linux 2.6. Components were connected to the computer either directly or through controller boards. Components connected directly to the computer included the motor controller (Galil, DMC-2183-DC24-DIN), LCD monitor (AEI, ALCDP7WVGATS), CMOS camera (Mightex, BCN-B013), distance sensor (Keyence LK-G37), and printer (Seiko, DPU-30). The components connected through the motor controller included photoelectric sensors (Omron, E3T-SL22), stepper motors for the main gantry and imager gantry (Arcus, DMAX-KDRV-17), stepper motor for the input bay conveyor (Arcus DMAX-KDRV-23), and LEDs (Lumileds, LXHL-PB09).

Results.

Example 13 describes the methods and results obtained by a device analyzed on this analyzer.

Conclusion.

This analyzer can automatically process sample devices with minimal user interaction. The device interacts with an analyzer that supports on demand processing, sample growth, non-magnified imaging and integrated waste disposal. It allows for detection of individual targets that have been bound to signaling and selection moieties to be analyzed using a standard CMOS camera at low magnification.

Variations.

One variant of analyzer includes a high capacity growth incubator. Such a large incubator would allow the analyzer to process devices at least 40 per hour. With its small footprint it would make an ideal high throughput machine for clinical laboratory, food processing and veterinary testing applications.

The invention claimed is:

1. A testing cartridge comprising:
at least one reservoir operable to receive a sample and fluidically connected to an imaging well comprising a detection area;
a growth well positioned between the at least one reservoir and the imaging well and containing growth media and at least one antibiotic;
signaling moieties and selection moieties stored in the at least one reservoir; and
a dye cushion reagent in the imaging well, the dye cushion reagent having a density agent and a dye that inhibits transmission of light.

2. The testing cartridge of claim 1, wherein the density agent has a density greater than water.

3. The testing cartridge of claim 2, wherein the density agent is selected from the group consisting of sucrose, diatrizoate, iodixanol, NaCl, CsCl, Percoll, metrizamide, and albumin.

4. The testing cartridge of claim 1, wherein the signaling moieties and selection moieties specifically bind a target,
wherein the detection area is transparent at wavelengths corresponding to a signal signature of the signaling moieties, and
wherein the device comprising the imaging well comprises features for alignment or registration of the imaging well with an imagining analyzer.

5. The testing cartridge of claim 1, wherein the longest linear dimension of the detection area is 2 cm, and wherein the depth of the imaging well is less than 2 cm.

6. The testing cartridge of claim 1, wherein the selection moieties are magnetic particles.

7. The testing cartridge of claim 1, wherein the signaling moieties are fluorescent particles.

8. The testing cartridge of claim 1, wherein the signaling moieties are fluorescent or fluorogenic stains.

9. The testing cartridge of claim 1, wherein the signaling moieties or selection moieties are stored in one of the one or more reservoirs in dry form.

10. The testing cartridge of claim 1, wherein the imaging well has a depth of ≥2 mm and the detection area has a shortest linear dimension of ≥1 mm.

11. The testing cartridge of claim 1, wherein the at least one reservoir is disposed above the imaging well.

12. The testing cartridge of claim 1, comprising a second growth well positioned between the at least one reservoir and a second imaging well and containing growth media without antibiotic.

* * * * *